(12) United States Patent
Thompson et al.

(10) Patent No.: US 10,639,281 B2
(45) Date of Patent: *May 5, 2020

(54) EXTRUDED IMMEDIATE RELEASE ABUSE DETERRENT PILL

(71) Applicant: Pharmaceutical Manufacturing Research Services, Inc., Horsham, PA (US)

(72) Inventors: Edwin R. Thompson, Horsham, PA (US); Eric R. Thompson, Chalfont, PA (US); Nicholas R. Myslinski, Bensalem, PA (US); Steven F. Kemeny, Philadelphia, PA (US)

(73) Assignee: Pharmaceutical Manufacturing Research Services, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/210,714

(22) Filed: Dec. 5, 2018

(65) Prior Publication Data

US 2019/0209481 A1 Jul. 11, 2019

Related U.S. Application Data

(62) Division of application No. 14/457,714, filed on Aug. 12, 2014, now Pat. No. 10,195,153.

(60) Provisional application No. 61/980,242, filed on Apr. 16, 2014, provisional application No. 61/864,926, filed on Aug. 12, 2013.

(51) Int. Cl.
| | |
|---|---|
| *A61K 9/20* | (2006.01) |
| *A61K 31/485* | (2006.01) |
| *B29C 48/00* | (2019.01) |
| *B29C 43/48* | (2006.01) |
| *B29K 105/00* | (2006.01) |
| *B29K 71/00* | (2006.01) |
| *B29C 43/46* | (2006.01) |
| *B29C 48/30* | (2019.01) |
| *B29C 48/04* | (2019.01) |
| *B29C 48/06* | (2019.01) |

(52) U.S. Cl.
CPC .......... *A61K 9/2095* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 31/485* (2013.01); *B29C 43/48* (2013.01); *B29C 48/0011* (2019.02); *B29C 48/022* (2019.02); *B29C 48/04* (2019.02); *B29C 48/06* (2019.02); *B29C 48/30* (2019.02); *B29C 48/303* (2019.02); *B29C 2043/463* (2013.01); *B29C 2043/483* (2013.01); *B29K 2071/02* (2013.01); *B29K 2105/0035* (2013.01); *B29K 2105/0038* (2013.01)

(58) Field of Classification Search
CPC .. A61K 9/2095; A61K 31/485; A61K 9/2031; B29K 2105/0038; B29K 2071/02
See application file for complete search history.

(56) References Cited

U.S. PATENT DOCUMENTS

| | | |
|---|---|---|
| 3,439,089 A | 4/1969 | Cherkas |
| 4,450,877 A | 5/1984 | Walker et al. |
| 5,141,961 A | 8/1992 | Coapman |
| 5,202,128 A | 4/1993 | Morella et al. |
| 5,266,331 A | 11/1993 | Oshlack et al. |
| 5,431,916 A | 7/1995 | White |
| 5,458,879 A | 10/1995 | Singh et al. |
| 5,614,218 A | 3/1997 | Olsson et al. |
| 5,616,621 A | 4/1997 | Popli et al. |
| 5,827,852 A | 10/1998 | Russell et al. |
| 5,840,337 A | 11/1998 | Cody et al. |
| 5,840,731 A | 11/1998 | Mayer et al. |
| 5,866,164 A | 2/1999 | Kuczynski et al. |
| 5,914,129 A | 6/1999 | Mauskop |
| 6,024,980 A | 2/2000 | Hoy |
| 6,068,855 A | 5/2000 | Leslie et al. |
| 6,102,254 A | 8/2000 | Ross |
| 6,159,501 A | 12/2000 | Skinhoj |
| 6,160,020 A | 12/2000 | Ohannesian et al. |
| 6,190,591 B1 | 2/2001 | van Lengerich |
| 6,207,674 B1 | 3/2001 | Smith |
| 6,245,357 B1 | 6/2001 | Edgren et al. |

(Continued)

FOREIGN PATENT DOCUMENTS

| | | |
|---|---|---|
| CA | 264736 A | 10/1926 |
| CA | 265145 A | 10/1926 |

(Continued)

OTHER PUBLICATIONS

U.S. Appl. No. 14/457,714, filed Aug. 12, 2014, U.S. Pat. No. 10,195,153, Issued.

(Continued)

*Primary Examiner* — Timothy P Thomas

(74) *Attorney, Agent, or Firm* — McCarter & English, LLP; Yu Lu

(57) ABSTRACT

The present disclosure relates to an oral, immediate release, abuse deterrent pill containing at least one active pharmaceutical ingredient susceptible to abuse which is homogenously spread throughout a carrier matrix used to deter abuse. The pill is prepared using hot melt extrusion and a forming unit through a continuous process. The formed pill is abuse deterrent to parenteral administration due at least to particle size, viscosity, or purity limitations.

20 Claims, 21 Drawing Sheets

(56) References Cited

U.S. PATENT DOCUMENTS

| | | |
|---|---|---|
| 6,251,430 B1 | 6/2001 | Zhang et al. |
| 6,277,384 B1 | 8/2001 | Kaiko et al. |
| 6,309,669 B1 | 10/2001 | Setterstrom et al. |
| 6,432,450 B1 | 8/2002 | Gergely et al. |
| 6,488,963 B1 | 12/2002 | McGinity et al. |
| 6,500,459 B1 | 12/2002 | Chhabra et al. |
| 6,572,891 B1 | 6/2003 | Ugarkovic |
| 6,627,635 B2 | 9/2003 | Palermo et al. |
| 6,706,281 B2 | 3/2004 | Oshlack et al. |
| 6,713,470 B2 | 3/2004 | Jackson |
| 6,740,333 B2 | 5/2004 | Beckett et al. |
| 6,753,009 B2 | 6/2004 | Luber et al. |
| 6,800,668 B1 | 10/2004 | Odidi et al. |
| 6,869,618 B2 | 3/2005 | Kiel et al. |
| 6,905,709 B2 | 6/2005 | Oshlack et al. |
| 6,923,988 B2 | 8/2005 | Patel et al. |
| 7,141,250 B2 | 11/2006 | Oshlack et al. |
| 7,201,920 B2 | 4/2007 | Kumar et al. |
| 7,214,385 B2 | 5/2007 | Gruber |
| 7,316,821 B2 | 1/2008 | Oshlack et al. |
| 7,384,653 B2 | 6/2008 | Wright, IV et al. |
| 7,413,750 B2 | 8/2008 | Kolter et al. |
| 7,514,100 B2 | 4/2009 | Oshlack et al. |
| 7,544,676 B2 | 6/2009 | Dolle et al. |
| 7,655,256 B2 | 2/2010 | Hughes |
| 7,666,337 B2 | 2/2010 | Yang et al. |
| 7,670,612 B2 | 3/2010 | Miller |
| 7,670,627 B2 | 3/2010 | Shefer et al. |
| 7,718,194 B2 | 5/2010 | Chenevier et al. |
| 7,744,916 B2 | 6/2010 | Pauletti et al. |
| 7,754,240 B2 | 7/2010 | Staniforth et al. |
| 7,780,987 B2 | 8/2010 | Zhou et al. |
| 7,790,215 B2 | 9/2010 | Sackler et al. |
| 7,842,307 B2 | 11/2010 | Oshlack et al. |
| 7,846,460 B2 | 12/2010 | Chenevier et al. |
| 7,846,476 B2 | 12/2010 | Oshlack et al. |
| 7,910,128 B2 | 3/2011 | Chang et al. |
| 7,943,173 B2 | 5/2011 | Breder et al. |
| 7,968,119 B2 | 6/2011 | Farrell |
| 8,029,822 B2 | 10/2011 | Faour et al. |
| 8,075,872 B2 | 12/2011 | Arkenau-Maric et al. |
| 8,114,383 B2 | 2/2012 | Bartholomaus et al. |
| 8,124,126 B2 | 2/2012 | Bosse et al. |
| 8,133,507 B2 | 3/2012 | Yum et al. |
| 8,138,169 B2 | 3/2012 | Oronsky et al. |
| 8,143,267 B2 | 3/2012 | Burch et al. |
| 8,188,108 B2 | 5/2012 | Mayo-Alvarez et al. |
| 8,202,542 B1 | 6/2012 | Mehta et al. |
| 8,216,610 B2 | 7/2012 | Roberts et al. |
| 8,263,125 B2 | 9/2012 | Vaya et al. |
| 8,313,757 B2 | 11/2012 | van Lengerich |
| 8,318,105 B2 | 11/2012 | Selinfreund et al. |
| 8,318,641 B2 | 11/2012 | Selinfreund et al. |
| 8,333,989 B2 | 12/2012 | Sukuru |
| 8,337,888 B2 | 12/2012 | Wright et al. |
| 8,362,029 B2 | 1/2013 | Evenstad et al. |
| 8,377,453 B2 | 2/2013 | Han et al. |
| 8,383,152 B2 | 2/2013 | Jans et al. |
| 8,394,813 B2 | 3/2013 | Mickle et al. |
| 8,415,401 B2 | 4/2013 | Yum et al. |
| 8,420,114 B2 | 4/2013 | Zanella et al. |
| 8,426,411 B2 | 4/2013 | Wishart et al. |
| 8,445,023 B2 | 5/2013 | Guimberteau et al. |
| 8,465,776 B2 | 6/2013 | Hoarau |
| 8,481,560 B2 | 7/2013 | Stinchcomb et al. |
| 8,486,448 B2 | 7/2013 | Rahmouni et al. |
| 8,486,449 B2 | 7/2013 | Rahmouni et al. |
| 8,497,303 B2 | 7/2013 | Wurn et al. |
| 8,501,160 B2 | 8/2013 | Cailly-Dufestel et al. |
| 8,518,438 B2 | 8/2013 | Rashid et al. |
| 8,524,267 B2 | 9/2013 | Zanella et al. |
| 8,563,038 B2 | 10/2013 | Andersen et al. |
| 8,575,196 B2 | 11/2013 | Riggs-Sauthier et al. |
| 8,591,947 B2 | 11/2013 | Vergez et al. |
| 8,597,681 B2 | 12/2013 | Park et al. |
| 8,603,514 B2 | 12/2013 | Yang et al. |
| 8,603,525 B2 | 12/2013 | Oury et al. |
| 8,609,143 B2 | 12/2013 | Fischer et al. |
| 8,617,605 B2 | 12/2013 | Fischer et al. |
| 8,623,401 B2 | 1/2014 | Modi |
| 8,623,412 B2 | 1/2014 | Farid et al. |
| 8,652,511 B2 | 2/2014 | Cottrell et al. |
| 8,653,066 B2 | 2/2014 | Bosse |
| 8,658,631 B1 | 2/2014 | Devarakonda et al. |
| 8,685,381 B2 | 4/2014 | Schlessinger et al. |
| 8,709,479 B2 | 4/2014 | Oury et al. |
| 8,722,086 B2 | 5/2014 | Arkenau-Mari et al. |
| 9,035,019 B2 | 5/2015 | Yang et al. |
| 10,195,153 B2 | 2/2019 | Thompson et al. |
| 2001/0031278 A1 | 10/2001 | Oshlack et al. |
| 2001/0044472 A1 | 11/2001 | Upadhyay et al. |
| 2001/0046971 A1 | 11/2001 | Hammerly |
| 2002/0055512 A1 | 5/2002 | Marin et al. |
| 2002/0068718 A1 | 6/2002 | Pierce |
| 2002/0099013 A1 | 7/2002 | Piccariello et al. |
| 2002/0164373 A1 | 11/2002 | Maloney |
| 2003/0049318 A1 | 3/2003 | Davis et al. |
| 2003/0068375 A1 | 4/2003 | Wright et al. |
| 2003/0091635 A1 | 5/2003 | Baichwal et al. |
| 2003/0092724 A1 | 5/2003 | Kao et al. |
| 2003/0117622 A1 | 6/2003 | Sevick-Muraca et al. |
| 2003/0125347 A1 | 7/2003 | Anderson et al. |
| 2003/0180362 A1 | 9/2003 | Park et al. |
| 2003/0185761 A1 | 10/2003 | Dugger |
| 2003/0191147 A1 | 10/2003 | Sherman et al. |
| 2003/0199439 A1 | 10/2003 | Simon |
| 2003/0203027 A1 | 10/2003 | Verreck et al. |
| 2003/0206898 A1 | 11/2003 | Fischkoff et al. |
| 2003/0224051 A1 | 12/2003 | Fink et al. |
| 2003/0235618 A1 | 12/2003 | Moros et al. |
| 2004/0009172 A1 | 1/2004 | Fischkoff et al. |
| 2004/0010000 A1 | 1/2004 | Ayer et al. |
| 2004/0022787 A1 | 2/2004 | Cohen et al. |
| 2004/0029864 A1 | 2/2004 | MacMillan |
| 2004/0043071 A1 | 3/2004 | Pauletti et al. |
| 2004/0062778 A1 | 4/2004 | Shefer et al. |
| 2004/0110781 A1 | 6/2004 | Harmon et al. |
| 2004/0122104 A1 | 6/2004 | Hirsh et al. |
| 2004/0156872 A1 | 8/2004 | Bosch et al. |
| 2004/0157928 A1 | 8/2004 | Kim et al. |
| 2004/0224020 A1 | 11/2004 | Schoenhard |
| 2004/0228802 A1 | 11/2004 | Chang et al. |
| 2004/0259948 A1 | 12/2004 | Tontonoz et al. |
| 2004/0265378 A1 | 12/2004 | Peng et al. |
| 2005/0004098 A1 | 1/2005 | Britten et al. |
| 2005/0013857 A1 | 1/2005 | Fu et al. |
| 2005/0020613 A1 | 1/2005 | Boehm et al. |
| 2005/0026842 A1 | 2/2005 | Simon |
| 2005/0059023 A1 | 3/2005 | Cantor |
| 2005/0106249 A1 | 5/2005 | Hwang et al. |
| 2005/0143471 A1 | 6/2005 | Gao et al. |
| 2005/0152905 A1 | 7/2005 | Omoigui |
| 2005/0169990 A1 | 8/2005 | Kao et al. |
| 2005/0222136 A1 | 10/2005 | Buschmann et al. |
| 2005/0226929 A1 | 10/2005 | Xie et al. |
| 2005/0233459 A1 | 10/2005 | Melker et al. |
| 2005/0245483 A1 | 11/2005 | Brogmann et al. |
| 2005/0265955 A1 | 12/2005 | Raman et al. |
| 2005/0266032 A1 | 12/2005 | Srinivasan et al. |
| 2005/0266072 A1 | 12/2005 | Oshlack et al. |
| 2006/0008527 A1 | 1/2006 | Lagoviyer et al. |
| 2006/0009478 A1 | 1/2006 | Friedmann et al. |
| 2006/0024365 A1 | 2/2006 | Vaya et al. |
| 2006/0024368 A1 | 2/2006 | Fassihi et al. |
| 2006/0039865 A1 | 2/2006 | Preston et al. |
| 2006/0052278 A1 | 3/2006 | Powell |
| 2006/0062734 A1 | 3/2006 | Melker et al. |
| 2006/0067971 A1 | 3/2006 | Story et al. |
| 2006/0073182 A1 | 4/2006 | Wong et al. |
| 2006/0074422 A1 | 4/2006 | Story et al. |
| 2006/0079557 A1 | 4/2006 | Dolle et al. |
| 2006/0093663 A1 | 5/2006 | Suzuki |
| 2006/0099254 A1 | 5/2006 | Desai et al. |
| 2006/0110327 A1 | 5/2006 | Emigh et al. |

(56) References Cited

U.S. PATENT DOCUMENTS

| | | |
|---|---|---|
| 2006/0111307 A1 | 5/2006 | Robbins |
| 2006/0115527 A1 | 6/2006 | Hassan et al. |
| 2006/0153915 A1 | 7/2006 | Park et al. |
| 2006/0165790 A1 | 7/2006 | Walden et al. |
| 2006/0177380 A1 | 8/2006 | Emigh et al. |
| 2006/0177381 A1 | 8/2006 | Brooks-Korn |
| 2006/0205752 A1 | 9/2006 | Whitehead |
| 2006/0210604 A1 | 9/2006 | Dadey et al. |
| 2006/0210631 A1 | 9/2006 | Patel et al. |
| 2006/0240105 A1 | 10/2006 | Devane et al. |
| 2006/0246134 A1 | 11/2006 | Venkatesh |
| 2006/0263429 A1 | 11/2006 | Feng |
| 2006/0292214 A1 | 12/2006 | Jenkins et al. |
| 2007/0003617 A1 | 1/2007 | Fischer et al. |
| 2007/0003622 A1 | 1/2007 | Srinivasan et al. |
| 2007/0009444 A1 | 1/2007 | Yamaguchi |
| 2007/0020339 A1 | 1/2007 | Bear |
| 2007/0027203 A1 | 2/2007 | Chen et al. |
| 2007/0042969 A1 | 2/2007 | Rauschkolb-Loffler et al. |
| 2007/0048228 A1 | 3/2007 | Arkenau-Maric et al. |
| 2007/0048377 A1 | 3/2007 | Rajabi-Siahboomi et al. |
| 2007/0072982 A1 | 3/2007 | Choi et al. |
| 2007/0087977 A1 | 4/2007 | Robbins |
| 2007/0104788 A1 | 5/2007 | Mulligan |
| 2007/0134493 A1 | 6/2007 | Meghpara |
| 2007/0140983 A1 | 6/2007 | Hall et al. |
| 2007/0148239 A1 | 6/2007 | Hall et al. |
| 2007/0167438 A1 | 7/2007 | Rosenzweig-Lipson |
| 2007/0190142 A1 | 8/2007 | Breitenbach et al. |
| 2007/0196491 A1 | 8/2007 | Venkatesh |
| 2007/0197661 A1 | 8/2007 | Bubnis et al. |
| 2007/0207200 A1 | 9/2007 | Plachetka et al. |
| 2007/0207222 A1 | 9/2007 | Yu et al. |
| 2007/0212417 A1 | 9/2007 | Cherukuri |
| 2007/0213717 A1 | 9/2007 | Trieu et al. |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0215511 A1 | 9/2007 | Mehta et al. |
| 2007/0231268 A1 | 10/2007 | Emigh et al. |
| 2007/0232529 A1 | 10/2007 | Mickle et al. |
| 2007/0244093 A1 | 10/2007 | Boehm et al. |
| 2007/0249566 A1 | 10/2007 | Martin et al. |
| 2007/0254027 A1 | 11/2007 | Martin et al. |
| 2007/0281016 A1 | 12/2007 | Kao et al. |
| 2007/0281017 A1 | 12/2007 | Kao et al. |
| 2007/0281018 A1 | 12/2007 | Qiu et al. |
| 2007/0292461 A1 | 12/2007 | Tamarkin et al. |
| 2007/0292508 A1 | 12/2007 | Szamosi et al. |
| 2007/0292510 A1 | 12/2007 | Huang |
| 2007/0298103 A1 | 12/2007 | Hayes |
| 2008/0014228 A1 | 1/2008 | Darmuzey et al. |
| 2008/0014274 A1 | 1/2008 | Bubnis et al. |
| 2008/0020032 A1 | 1/2008 | Crowley et al. |
| 2008/0020039 A1 | 1/2008 | Parikh et al. |
| 2008/0026040 A1 | 1/2008 | Farr et al. |
| 2008/0026062 A1 | 1/2008 | Farr et al. |
| 2008/0031901 A1 | 2/2008 | Qiu et al. |
| 2008/0057122 A1 | 3/2008 | Toney-Parker et al. |
| 2008/0063725 A1 | 3/2008 | Guimberteau et al. |
| 2008/0069871 A1 | 3/2008 | Vaughn et al. |
| 2008/0069878 A1 | 3/2008 | Venkatesh et al. |
| 2008/0069889 A1 | 3/2008 | Cherukuri |
| 2008/0081071 A1 | 4/2008 | Sanghvi et al. |
| 2008/0085304 A1 | 4/2008 | Baichwal et al. |
| 2008/0085312 A1 | 4/2008 | Wilson et al. |
| 2008/0102113 A1 | 5/2008 | Rosenberg |
| 2008/0102123 A1 | 5/2008 | Schachter et al. |
| 2008/0103206 A1 | 5/2008 | Swann et al. |
| 2008/0132751 A1 | 6/2008 | Keller et al. |
| 2008/0152595 A1 | 6/2008 | Emigh et al. |
| 2008/0152704 A1 | 6/2008 | Bonadeo et al. |
| 2008/0171083 A1 | 7/2008 | Staniforth et al. |
| 2008/0175897 A1 | 7/2008 | Plachetka et al. |
| 2008/0193540 A1 | 8/2008 | Soula et al. |
| 2008/0207669 A1 | 8/2008 | Perez et al. |
| 2008/0226702 A1 | 9/2008 | Goldberg |
| 2008/0234237 A1 | 9/2008 | Maddaford et al. |
| 2008/0260815 A1 | 10/2008 | Hayes et al. |
| 2008/0260837 A1 | 10/2008 | Namburi et al. |
| 2008/0260844 A1 | 10/2008 | Soula et al. |
| 2008/0286343 A1 | 11/2008 | Cengic et al. |
| 2008/0286344 A1 | 11/2008 | Darmuzey et al. |
| 2008/0292683 A1 | 11/2008 | Sanghvi et al. |
| 2008/0293695 A1 | 11/2008 | Bristol et al. |
| 2008/0311162 A1 | 12/2008 | Darmuzey et al. |
| 2009/0004267 A1 | 1/2009 | Arkenau-Maric et al. |
| 2009/0004281 A1 | 1/2009 | Nghiem et al. |
| 2009/0004285 A1 | 1/2009 | Yu et al. |
| 2009/0022798 A1 | 1/2009 | Rosenberg et al. |
| 2009/0028873 A1 | 1/2009 | Gant et al. |
| 2009/0035315 A1 | 2/2009 | Christgau et al. |
| 2009/0041838 A1 | 2/2009 | Guimberteau et al. |
| 2009/0061011 A1 | 3/2009 | Talton |
| 2009/0068247 A1 | 3/2009 | Jay |
| 2009/0074866 A1 | 3/2009 | Chen |
| 2009/0081290 A1 | 3/2009 | McKenna et al. |
| 2009/0082466 A1 | 3/2009 | Babul |
| 2009/0087483 A1 | 4/2009 | Sison |
| 2009/0110724 A1 | 4/2009 | Giordano |
| 2009/0124697 A1 | 5/2009 | Cloutier et al. |
| 2009/0143761 A1 | 6/2009 | Cantor et al. |
| 2009/0155193 A1 | 6/2009 | Joabsson et al. |
| 2009/0169626 A1 | 7/2009 | Fleischer et al. |
| 2009/0175939 A1 | 7/2009 | Bosse et al. |
| 2009/0198248 A1 | 8/2009 | Yeung et al. |
| 2009/0220611 A1 | 9/2009 | Dargelas et al. |
| 2009/0220613 A1 | 9/2009 | Odidi et al. |
| 2009/0232887 A1 | 9/2009 | Odidi et al. |
| 2009/0238873 A1 | 9/2009 | Chattaraj et al. |
| 2009/0246257 A1 | 10/2009 | Modi |
| 2009/0258947 A1 | 10/2009 | Jain et al. |
| 2009/0317355 A1 | 12/2009 | Roth et al. |
| 2010/0003322 A1 | 1/2010 | Lai et al. |
| 2010/0003332 A1 | 1/2010 | Bae et al. |
| 2010/0010030 A1 | 1/2010 | Jain et al. |
| 2010/0021543 A1 | 1/2010 | Schierstedt |
| 2010/0041759 A1 | 2/2010 | Wilson et al. |
| 2010/0048602 A1 | 2/2010 | Riggs-Sauthier et al. |
| 2010/0051801 A1 | 3/2010 | Erfurth et al. |
| 2010/0076074 A1 | 3/2010 | Gant et al. |
| 2010/0080829 A1 | 4/2010 | Dulieu et al. |
| 2010/0098746 A1 | 4/2010 | King |
| 2010/0099696 A1 | 4/2010 | Soscia et al. |
| 2010/0111830 A1 | 5/2010 | Boyden et al. |
| 2010/0143449 A1 | 6/2010 | Kolesnikov |
| 2010/0152299 A1 | 6/2010 | Vasanthavada et al. |
| 2010/0172989 A1 | 7/2010 | Roth et al. |
| 2010/0196471 A1 | 8/2010 | Jain et al. |
| 2010/0196474 A1 | 8/2010 | Han et al. |
| 2010/0204259 A1 | 8/2010 | Tygesen et al. |
| 2010/0215737 A1 | 8/2010 | Coulter |
| 2010/0226943 A1 | 9/2010 | Brennan et al. |
| 2010/0226978 A1 | 9/2010 | Petereit et al. |
| 2010/0239667 A1 | 9/2010 | Hemmingsen et al. |
| 2010/0249045 A1 | 9/2010 | Babul |
| 2010/0260858 A1 | 10/2010 | Ruddy et al. |
| 2010/0266682 A1 | 10/2010 | Davar et al. |
| 2010/0286100 A1 | 11/2010 | First et al. |
| 2010/0291201 A1 | 11/2010 | Shah et al. |
| 2010/0291205 A1 | 11/2010 | Downie et al. |
| 2010/0304998 A1 | 12/2010 | Sem |
| 2011/0003005 A1 | 1/2011 | Venkatesh et al. |
| 2011/0003006 A1 | 1/2011 | Venkatesh et al. |
| 2011/0008424 A1 | 1/2011 | Chang et al. |
| 2011/0020440 A1 | 1/2011 | Modi et al. |
| 2011/0020451 A1 | 1/2011 | Bartholomaus et al. |
| 2011/0020776 A1 | 1/2011 | Nielsen et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0091537 A1 | 4/2011 | Castan et al. |
| 2011/0091563 A1 | 4/2011 | Kurasawa et al. |

(56) References Cited

U.S. PATENT DOCUMENTS

| | | |
|---|---|---|
| 2011/0104214 A1 | 5/2011 | Oshlack et al. |
| 2011/0104272 A1 | 5/2011 | Hou |
| 2011/0118189 A1 | 5/2011 | Farr et al. |
| 2011/0129530 A1 | 6/2011 | Venkatesh et al. |
| 2011/0142905 A1 | 6/2011 | Bar-Shalom et al. |
| 2011/0142943 A1 | 6/2011 | Rariy et al. |
| 2011/0150989 A1 | 6/2011 | Park et al. |
| 2011/0159048 A1 | 6/2011 | Crain et al. |
| 2011/0159100 A1 | 6/2011 | Andersen et al. |
| 2011/0160239 A1 | 6/2011 | Brodbeck et al. |
| 2011/0165248 A1 | 7/2011 | Machonis |
| 2011/0182987 A1 | 7/2011 | Bawa et al. |
| 2011/0195116 A1 | 8/2011 | Hobbs et al. |
| 2011/0195520 A1 | 8/2011 | Leider et al. |
| 2011/0195989 A1 | 8/2011 | Rudnic et al. |
| 2011/0207761 A1 | 8/2011 | Losev et al. |
| 2011/0218209 A1 | 9/2011 | Yered |
| 2011/0229562 A1 | 9/2011 | Bar et al. |
| 2011/0230816 A1 | 9/2011 | Copp-Howland |
| 2011/0237614 A1 | 9/2011 | Jude-Fishburn et al. |
| 2011/0239745 A1 | 10/2011 | Satcher, Jr. et al. |
| 2011/0245208 A1 | 10/2011 | Diatchenko et al. |
| 2011/0262539 A1 | 10/2011 | Bosse et al. |
| 2011/0287095 A1 | 11/2011 | Park et al. |
| 2011/0311626 A1 | 12/2011 | Venkatesh et al. |
| 2011/0311628 A1 | 12/2011 | Muthusamy et al. |
| 2011/0311631 A1 | 12/2011 | Baer et al. |
| 2012/0009129 A1 | 1/2012 | Brzeczko |
| 2012/0010157 A1 | 1/2012 | Polvino et al. |
| 2012/0015007 A1 | 1/2012 | Bredenberg et al. |
| 2012/0015031 A1 | 1/2012 | Sesha |
| 2012/0021370 A1 | 1/2012 | Drapeau et al. |
| 2012/0022009 A1 | 1/2012 | Bryant |
| 2012/0034306 A1 | 2/2012 | Pollock et al. |
| 2012/0039957 A1 | 2/2012 | Brzeczko et al. |
| 2012/0045506 A1 | 2/2012 | Baer et al. |
| 2012/0059065 A1 | 3/2012 | Barnscheid et al. |
| 2012/0063996 A1 | 3/2012 | Bosch et al. |
| 2012/0064159 A1 | 3/2012 | Chauhan et al. |
| 2012/0065220 A1 | 3/2012 | Barnscheid et al. |
| 2012/0083506 A1 | 4/2012 | Herry et al. |
| 2012/0088786 A1 | 4/2012 | Dadagher et al. |
| 2012/0093929 A1 | 4/2012 | Oksche et al. |
| 2012/0100183 A1 | 4/2012 | Schlessinger et al. |
| 2012/0107400 A1 | 5/2012 | Muthusamy et al. |
| 2012/0121594 A1 | 5/2012 | Smith |
| 2012/0121724 A1 | 5/2012 | Maibach |
| 2012/0135075 A1 | 5/2012 | Mohammad |
| 2012/0135077 A1 | 5/2012 | Mehta et al. |
| 2012/0141554 A1 | 6/2012 | Dill |
| 2012/0164209 A1 | 6/2012 | Shah et al. |
| 2012/0164220 A1 | 6/2012 | Huang |
| 2012/0202838 A1 | 8/2012 | Ghosh et al. |
| 2012/0205532 A1 | 8/2012 | Mazza |
| 2012/0207825 A1 | 8/2012 | Roy et al. |
| 2012/0237556 A1 | 9/2012 | Schlessinger et al. |
| 2012/0245156 A1 | 9/2012 | Nguyen |
| 2012/0251590 A1 | 10/2012 | Cruz et al. |
| 2012/0282335 A1 | 11/2012 | Venkatesh et al. |
| 2012/0289534 A1 | 11/2012 | Pergolizzi et al. |
| 2012/0321674 A1 | 12/2012 | Vachon et al. |
| 2013/0004415 A1 | 1/2013 | Moudgil et al. |
| 2013/0011479 A1 | 1/2013 | Angeli et al. |
| 2013/0017262 A1 | 1/2013 | Mullen et al. |
| 2013/0022646 A1 | 1/2013 | Rudnic et al. |
| 2013/0022676 A1 | 1/2013 | Mullen et al. |
| 2013/0022677 A1 | 1/2013 | Mullen et al. |
| 2013/0023553 A1 | 1/2013 | Jude-Fishburn et al. |
| 2013/0028955 A1 | 1/2013 | Tolia |
| 2013/0028970 A1 | 1/2013 | Schwier et al. |
| 2013/0028972 A1 | 1/2013 | Schwier et al. |
| 2013/0030360 A1 | 1/2013 | Stopek et al. |
| 2013/0059010 A1 | 3/2013 | Herry et al. |
| 2013/0102959 A1 | 4/2013 | Stopek et al. |
| 2013/0115249 A1 | 5/2013 | Vergez et al. |
| 2013/0122098 A1 | 5/2013 | First et al. |
| 2013/0122101 A1 | 5/2013 | Habib et al. |
| 2013/0123294 A1 | 5/2013 | Lebon et al. |
| 2013/0129825 A1 | 5/2013 | Billoet |
| 2013/0129826 A1 | 5/2013 | Gei Ler et al. |
| 2013/0129828 A1 | 5/2013 | Talton |
| 2013/0136792 A1 | 5/2013 | Draper et al. |
| 2013/0156853 A1 | 6/2013 | Zhang et al. |
| 2013/0165467 A1 | 6/2013 | Hayes et al. |
| 2013/0168321 A1 | 7/2013 | Cannon et al. |
| 2013/0197021 A1 | 8/2013 | Mohammad et al. |
| 2013/0209557 A1 | 8/2013 | Barnscheid |
| 2013/0209561 A1 | 8/2013 | Kao et al. |
| 2013/0217777 A1 | 8/2013 | Kirkorian |
| 2013/0225412 A1 | 8/2013 | Sardari Lodriche et al. |
| 2013/0225625 A1 | 8/2013 | Barnscheid et al. |
| 2013/0225697 A1 | 8/2013 | Barnscheid et al. |
| 2013/0230587 A1 | 9/2013 | Pilgaonkar et al. |
| 2013/0237559 A1 | 9/2013 | Ortiz et al. |
| 2013/0245054 A1 | 9/2013 | Prater et al. |
| 2013/0259941 A1 | 10/2013 | O'Donnell |
| 2013/0273153 A1 | 10/2013 | Park et al. |
| 2013/0273162 A1 | 10/2013 | Li |
| 2013/0280176 A1 | 10/2013 | Diezi et al. |
| 2013/0280177 A1* | 10/2013 | Raman ............... A61K 9/0007 424/44 |
| 2013/0280338 A1 | 10/2013 | Wening et al. |
| 2013/0303623 A1 | 11/2013 | Barnscheid et al. |
| 2013/0330409 A1 | 12/2013 | Mohammad |
| 2013/0345250 A1 | 12/2013 | Fleming |
| 2014/0010873 A1 | 1/2014 | Tygesen et al. |
| 2014/0010874 A1 | 1/2014 | Sackler |
| 2014/0017310 A1 | 1/2014 | Gower et al. |
| 2014/0031734 A1 | 1/2014 | Saxena et al. |
| 2014/0045801 A1 | 2/2014 | Rossi |
| 2014/0050787 A1 | 2/2014 | Tygesen et al. |
| 2014/0056979 A1 | 2/2014 | Huang |
| 2014/0066516 A1 | 3/2014 | Clarke et al. |
| 2014/0094438 A1 | 4/2014 | Mitchell |
| 2014/0105977 A1 | 4/2014 | Devarakonda et al. |
| 2014/0105987 A1 | 4/2014 | Rariy et al. |
| 2014/0112984 A1 | 4/2014 | Arkenau-Maric et al. |
| 2014/0112989 A1 | 4/2014 | Bartholomaus et al. |
| 2014/0127300 A1 | 5/2014 | Tengler et al. |
| 2014/0171481 A1 | 6/2014 | Liepold et al. |
| 2015/0283087 A1 | 10/2015 | Vamvakas et al. |

FOREIGN PATENT DOCUMENTS

| | | |
|---|---|---|
| CA | 265559 A | 11/1926 |
| CA | 2319353 A1 | 8/1999 |
| CA | 2408106 A1 | 11/2001 |
| CA | 2386794 A1 | 1/2002 |
| CA | 2544404 A1 | 6/2005 |
| CA | 2573583 A1 | 2/2006 |
| CA | 2649265 A1 | 8/2007 |
| CA | 2690829 A1 | 1/2009 |
| CA | 2737307 A1 | 4/2010 |
| CA | 2750400 A1 | 7/2010 |
| CA | 2766179 A1 | 12/2010 |
| CA | 2847613 A1 | 3/2013 |
| CN | 101824144 A | 9/2010 |
| CN | 101987081 A | 3/2011 |
| CN | 102344534 A | 2/2012 |
| CN | 102389423 A | 3/2012 |
| CN | 102648985 A | 8/2012 |
| CN | 103040829 A | 4/2013 |
| CN | 103070840 A | 5/2013 |
| CN | 103637987 A | 3/2014 |
| CN | 103637998 A | 3/2014 |
| DE | 2326141 A1 | 12/1973 |
| DE | 2705051 A1 | 8/1977 |
| DE | 10215067 A1 | 10/2003 |
| DE | 10215131 A1 | 10/2003 |
| DE | 202006014131 U1 | 1/2007 |
| DE | 102007021549 A1 | 11/2008 |
| EP | 103991 A2 | 3/1984 |
| EP | 0152292 A2 | 8/1985 |
| EP | 459387 A2 | 12/1991 |

(56) References Cited

FOREIGN PATENT DOCUMENTS

| | | | |
|---|---|---|---|
| EP | 1663229 A2 | 6/2006 |
| EP | 1980245 A1 | 10/2008 |
| EP | 2007360 A1 | 12/2008 |
| EP | 2067471 A1 | 6/2009 |
| EP | 2106799 A1 | 10/2009 |
| EP | 2123626 A1 | 11/2009 |
| EP | 2343071 A1 | 7/2011 |
| EP | 2359812 A1 | 8/2011 |
| EP | 2444064 A1 | 4/2012 |
| EP | 2457900 A1 | 5/2012 |
| EP | 2548863 A1 | 1/2013 |
| EP | 2548876 A1 | 1/2013 |
| EP | 2586607 A1 | 5/2013 |
| EP | 2626358 A1 | 8/2013 |
| FR | 2850576 A1 | 8/2004 |
| FR | 2878158 A1 | 5/2006 |
| FR | 2878161 A1 | 5/2006 |
| FR | 2892937 A1 | 5/2007 |
| FR | 2960775 A1 | 12/2011 |
| GB | 135381 A | 12/1919 |
| HU | 9903375 A2 | 2/2000 |
| IN | 2005MU01013 | 6/2007 |
| IN | 2006KO00351 | 7/2007 |
| IN | 2005MU01012 | 8/2007 |
| IN | 2009DE00453 | 4/2013 |
| JP | 55084166 | 6/1980 |
| JP | 60092214 | 5/1985 |
| JP | 11033084 | 2/1999 |
| JP | 2009256214 A | 11/2009 |
| JP | 2010053078 A | 3/2010 |
| JP | 2010173976 A | 8/2010 |
| JP | 2011256115 A | 12/2011 |
| JP | 2013249458 A | 12/2013 |
| KR | 2008026754 | 3/2008 |
| KR | 1203186 | 11/2012 |
| PL | 133984 B2 | 7/1985 |
| WO | WO-1985/03439 A1 | 8/1985 |
| WO | WO-1991/07950 A1 | 6/1991 |
| WO | WO-1993/24154 A1 | 12/1993 |
| WO | WO-1994/08551 A2 | 4/1994 |
| WO | WO-1994/18970 A1 | 9/1994 |
| WO | WO-1994/25009 A1 | 11/1994 |
| WO | WO-1994/26731 A1 | 11/1994 |
| WO | WO-1995/23591 A1 | 9/1995 |
| WO | WO-1996/14059 A1 | 5/1996 |
| WO | WO-1996/23486 A1 | 8/1996 |
| WO | WO-1997/04780 A2 | 2/1997 |
| WO | WO-1997/20556 A1 | 6/1997 |
| WO | WO-1997/20561 A1 | 6/1997 |
| WO | WO-1997/33566 A2 | 9/1997 |
| WO | WO-1997/49384 A1 | 12/1997 |
| WO | WO-1998/03179 A1 | 1/1998 |
| WO | WO-1998/18610 A1 | 5/1998 |
| WO | WO-1998/25613 A2 | 6/1998 |
| WO | WO-1998/32427 A1 | 7/1998 |
| WO | WO-1998/50044 A1 | 11/1998 |
| WO | WO-1998/50075 A1 | 11/1998 |
| WO | WO-1999/07413 A1 | 2/1999 |
| WO | WO-1999/44591 A1 | 9/1999 |
| WO | WO-1999/53922 A1 | 10/1999 |
| WO | WO-1999/66919 A1 | 12/1999 |
| WO | WO-2000/21504 A1 | 4/2000 |
| WO | WO-2000/29022 A1 | 5/2000 |
| WO | WO-2000/29023 A1 | 5/2000 |
| WO | WO-2000/38649 A1 | 7/2000 |
| WO | WO-2000/61537 A2 | 10/2000 |
| WO | WO-2000/61541 A2 | 10/2000 |
| WO | WO-2001/08662 A1 | 2/2001 |
| WO | WO-2001/12584 A2 | 2/2001 |
| WO | WO-2001/15667 A1 | 3/2001 |
| WO | WO-2001/32101 A1 | 5/2001 |
| WO | WO-2001/32928 A2 | 5/2001 |
| WO | WO-2001/76576 A2 | 10/2001 |
| WO | WO-2001/85150 A2 | 11/2001 |
| WO | WO-2001/85257 A2 | 11/2001 |
| WO | WO-2001/91736 A2 | 12/2001 |
| WO | WO-2002/05647 A1 | 1/2002 |
| WO | WO-2002/32395 A2 | 4/2002 |
| WO | WO-2002/34237 A1 | 5/2002 |
| WO | WO-2002/051432 A1 | 7/2002 |
| WO | WO-2002/056861 A2 | 7/2002 |
| WO | WO-2002/100351 A1 | 12/2002 |
| WO | WO-2003/004009 A1 | 1/2003 |
| WO | WO-2003/013481 A1 | 2/2003 |
| WO | WO-2003/020200 A2 | 3/2003 |
| WO | WO-2003/024430 A1 | 3/2003 |
| WO | WO-2003/032990 A2 | 4/2003 |
| WO | WO-2003/034991 A2 | 5/2003 |
| WO | WO-2003/051878 A1 | 6/2003 |
| WO | WO-2003/063834 A1 | 8/2003 |
| WO | WO-2003/065988 A2 | 8/2003 |
| WO | WO-2003/066029 A2 | 8/2003 |
| WO | WO-2003/066030 A2 | 8/2003 |
| WO | WO-2003/068197 A1 | 8/2003 |
| WO | WO-2003/079972 A2 | 10/2003 |
| WO | WO-2003/088991 A1 | 10/2003 |
| WO | WO-2003/092648 A1 | 11/2003 |
| WO | WO-2003/101476 A1 | 12/2003 |
| WO | WO-2004/026256 A2 | 4/2004 |
| WO | WO-2004/039320 A2 | 5/2004 |
| WO | WO-2004/045551 A2 | 6/2004 |
| WO | WO-2004/054542 A2 | 7/2004 |
| WO | WO-2004/064832 A2 | 8/2004 |
| WO | WO-2004/069135 A2 | 8/2004 |
| WO | WO-2004/075832 A2 | 9/2004 |
| WO | WO-2004/082588 A2 | 9/2004 |
| WO | WO-2004/082719 A1 | 9/2004 |
| WO | WO-2004/084868 A1 | 10/2004 |
| WO | WO-2004/108163 A2 | 12/2004 |
| WO | WO-2005/000310 A1 | 1/2005 |
| WO | WO-2005/000331 A2 | 1/2005 |
| WO | WO-2005/002597 A1 | 1/2005 |
| WO | WO-2005/004989 A2 | 1/2005 |
| WO | WO-2005/009409 A2 | 2/2005 |
| WO | WO-2005/028539 A2 | 3/2005 |
| WO | WO-2005/030181 A1 | 4/2005 |
| WO | WO-2005/030182 A1 | 4/2005 |
| WO | WO-2005/032474 A2 | 4/2005 |
| WO | WO-2005/032555 A1 | 4/2005 |
| WO | WO-2005/038049 A2 | 4/2005 |
| WO | WO-2005/046727 A2 | 5/2005 |
| WO | WO-2005/051356 A1 | 6/2005 |
| WO | WO-2005/058303 A1 | 6/2005 |
| WO | WO-2005/063206 A1 | 7/2005 |
| WO | WO-2005/063219 A2 | 7/2005 |
| WO | WO-2005/070465 A2 | 8/2005 |
| WO | WO-2005/079760 A1 | 9/2005 |
| WO | WO-2005/092306 A1 | 10/2005 |
| WO | WO-2005/102338 A1 | 11/2005 |
| WO | WO-2005/103070 A1 | 11/2005 |
| WO | WO-2005/107467 A2 | 11/2005 |
| WO | WO-2005/107726 A2 | 11/2005 |
| WO | WO-2005/123192 A2 | 12/2005 |
| WO | WO-2005/123193 A2 | 12/2005 |
| WO | WO-2006/014967 A1 | 2/2006 |
| WO | WO-2006/020930 A2 | 2/2006 |
| WO | WO-2006/024018 A2 | 3/2006 |
| WO | WO-2006/024881 A2 | 3/2006 |
| WO | WO-2006/030402 A2 | 3/2006 |
| WO | WO-2006/046114 A2 | 5/2006 |
| WO | WO-2006/050165 A2 | 5/2006 |
| WO | WO-2006/069030 A1 | 6/2006 |
| WO | WO-2006/069202 A2 | 6/2006 |
| WO | WO-2006/075123 A1 | 7/2006 |
| WO | WO-2006/085101 A2 | 8/2006 |
| WO | WO-2006/092691 A1 | 9/2006 |
| WO | WO-2006/099541 A2 | 9/2006 |
| WO | WO-2006/103418 A1 | 10/2006 |
| WO | WO-2006/103551 A1 | 10/2006 |
| WO | WO-2006/105205 A1 | 10/2006 |
| WO | WO-2006/116148 A2 | 11/2006 |
| WO | WO-2006/133733 A1 | 12/2006 |
| WO | WO-2006/138278 A1 | 12/2006 |
| WO | WO-2007/021970 A2 | 2/2007 |

(56) References Cited

FOREIGN PATENT DOCUMENTS

| | | |
|---|---|---|
| WO | WO-2007/036671 A2 | 4/2007 |
| WO | WO-2007/050631 A2 | 5/2007 |
| WO | WO-2007/056142 A2 | 5/2007 |
| WO | WO-2007/058960 A1 | 5/2007 |
| WO | WO-2007/070632 A2 | 6/2007 |
| WO | WO-2007/072503 A2 | 6/2007 |
| WO | WO-2007/087452 A2 | 8/2007 |
| WO | WO-2007/089328 A2 | 8/2007 |
| WO | WO-2007/094694 A1 | 8/2007 |
| WO | WO-2007/106550 A2 | 9/2007 |
| WO | WO-2007/128349 A1 | 11/2007 |
| WO | WO-2007/128884 A1 | 11/2007 |
| WO | WO-2007/131357 A1 | 11/2007 |
| WO | WO-2007/133583 A2 | 11/2007 |
| WO | WO-2007/135193 A2 | 11/2007 |
| WO | WO-2007/141328 A1 | 12/2007 |
| WO | WO-2007/149438 A2 | 12/2007 |
| WO | WO-2008/001341 A1 | 1/2008 |
| WO | WO-2008/007152 A2 | 1/2008 |
| WO | WO-2008/008364 A2 | 1/2008 |
| WO | WO-2008/011169 A2 | 1/2008 |
| WO | WO-2008/013710 A2 | 1/2008 |
| WO | WO-2008/021394 A2 | 2/2008 |
| WO | WO-2008/023261 A1 | 2/2008 |
| WO | WO-2008/027350 A2 | 3/2008 |
| WO | WO-2008/027442 A2 | 3/2008 |
| WO | WO-2008/033351 A2 | 3/2008 |
| WO | WO-2008/033523 A1 | 3/2008 |
| WO | WO-2008/057579 A2 | 5/2008 |
| WO | WO-2008/057608 A2 | 5/2008 |
| WO | WO-2008/060552 A2 | 5/2008 |
| WO | WO-2008/063625 A2 | 5/2008 |
| WO | WO-2008/067222 A1 | 6/2008 |
| WO | WO-2008/068471 A1 | 6/2008 |
| WO | WO-2008/070268 A2 | 6/2008 |
| WO | WO-2008/086804 A2 | 7/2008 |
| WO | WO-2008/097976 A1 | 8/2008 |
| WO | WO-2008/100977 A2 | 8/2008 |
| WO | WO-2008/106429 A2 | 9/2008 |
| WO | WO-2008/107410 A1 | 9/2008 |
| WO | WO-2008/108957 A2 | 9/2008 |
| WO | WO-2008/108958 A2 | 9/2008 |
| WO | WO-2008/108986 A2 | 9/2008 |
| WO | WO-2008/131056 A2 | 10/2008 |
| WO | WO-2008/131057 A2 | 10/2008 |
| WO | WO-2008/132712 A2 | 11/2008 |
| WO | WO-2008/133928 A2 | 11/2008 |
| WO | WO-2008/134600 A1 | 11/2008 |
| WO | WO-2008/135283 A1 | 11/2008 |
| WO | WO-2008/140459 A1 | 11/2008 |
| WO | WO-2008/140460 A1 | 11/2008 |
| WO | WO-2008/140461 A1 | 11/2008 |
| WO | WO-2008/141189 A1 | 11/2008 |
| WO | WO-2008/148798 A2 | 12/2008 |
| WO | WO-2008/155620 A1 | 12/2008 |
| WO | WO-2008/157308 A2 | 12/2008 |
| WO | WO-2009/002299 A1 | 12/2008 |
| WO | WO-2009/005613 A2 | 1/2009 |
| WO | WO-2009/005803 A1 | 1/2009 |
| WO | WO-2009/014534 A1 | 1/2009 |
| WO | WO-2009/021055 A1 | 2/2009 |
| WO | WO-2009/023672 A2 | 2/2009 |
| WO | WO-2009/026241 A1 | 2/2009 |
| WO | WO-2009/042960 A1 | 4/2009 |
| WO | WO-2009/047175 A2 | 4/2009 |
| WO | WO-2009/073686 A1 | 6/2009 |
| WO | WO-2009/076361 A1 | 6/2009 |
| WO | WO-2009/076764 A1 | 6/2009 |
| WO | WO-2009/089134 A1 | 7/2009 |
| WO | WO-2009/100118 A1 | 8/2009 |
| WO | WO-2009/104838 A1 | 8/2009 |
| WO | WO-2009/109911 A1 | 9/2009 |
| WO | WO-2009/114648 A1 | 9/2009 |
| WO | WO-2009/118764 A1 | 10/2009 |
| WO | WO-2009/120889 A2 | 10/2009 |
| WO | WO-2009/121496 A2 | 10/2009 |
| WO | WO-2009/124755 A1 | 10/2009 |
| WO | WO-2009/126931 A2 | 10/2009 |
| WO | WO-2009/134336 A1 | 11/2009 |
| WO | WO-2009/137086 A1 | 11/2009 |
| WO | WO-2009/143295 A1 | 11/2009 |
| WO | WO-2009/143299 A1 | 11/2009 |
| WO | WO-2009/152133 A1 | 12/2009 |
| WO | WO-2010/000073 A1 | 1/2010 |
| WO | WO-2010/017821 A1 | 2/2010 |
| WO | WO-2010/032128 A1 | 3/2010 |
| WO | WO-2010/033195 A1 | 3/2010 |
| WO | WO-2010/068789 A1 | 6/2010 |
| WO | WO-2010/069050 A1 | 6/2010 |
| WO | WO-2010/083894 A1 | 7/2010 |
| WO | WO-2010/089132 A1 | 8/2010 |
| WO | WO-2010/096045 A1 | 8/2010 |
| WO | WO-2010/103365 A2 | 9/2010 |
| WO | WO-2010/103367 A1 | 9/2010 |
| WO | WO-2010/123999 A2 | 10/2010 |
| WO | WO-2010/124089 A2 | 10/2010 |
| WO | WO-2010/127345 A2 | 11/2010 |
| WO | WO-2010/127346 A1 | 11/2010 |
| WO | WO-2010/132095 A1 | 11/2010 |
| WO | WO-2010/135340 A2 | 11/2010 |
| WO | WO-2010/140007 A2 | 12/2010 |
| WO | WO-2010/141505 A1 | 12/2010 |
| WO | WO-2010/150930 A1 | 12/2010 |
| WO | WO-2010/151020 A2 | 12/2010 |
| WO | WO-2010/151823 A1 | 12/2010 |
| WO | WO-2011/005671 A1 | 1/2011 |
| WO | WO-2011/006012 A1 | 1/2011 |
| WO | WO-2011/008298 A2 | 1/2011 |
| WO | WO-2011/009603 A1 | 1/2011 |
| WO | WO-2011/009604 A1 | 1/2011 |
| WO | WO-2011/011060 A1 | 1/2011 |
| WO | WO-2011/011199 A1 | 1/2011 |
| WO | WO-2011/011543 A1 | 1/2011 |
| WO | WO-2011/012715 A1 | 2/2011 |
| WO | WO-2011/039768 A2 | 4/2011 |
| WO | WO-2011/045769 A2 | 4/2011 |
| WO | WO-2011/057199 A1 | 5/2011 |
| WO | WO-2011/066287 A1 | 6/2011 |
| WO | WO-2011/066980 A2 | 6/2011 |
| WO | WO-2011/068723 A1 | 6/2011 |
| WO | WO-2011/068881 A1 | 6/2011 |
| WO | WO-2011/084593 A2 | 7/2011 |
| WO | WO-2011/086193 A1 | 7/2011 |
| WO | WO-2011/088140 A1 | 7/2011 |
| WO | WO-2011/106076 A1 | 9/2011 |
| WO | WO-2011/107750 A2 | 9/2011 |
| WO | WO-2011/107855 A2 | 9/2011 |
| WO | WO-2011/120084 A1 | 10/2011 |
| WO | WO-2011/123719 A2 | 10/2011 |
| WO | WO-2011/123866 A1 | 10/2011 |
| WO | WO-2011/127467 A1 | 10/2011 |
| WO | WO-2011/139595 A2 | 11/2011 |
| WO | WO-2012/007159 A2 | 1/2012 |
| WO | WO-2012/011917 A1 | 1/2012 |
| WO | WO-2012/016569 A1 | 2/2012 |
| WO | WO-2012/020097 A2 | 2/2012 |
| WO | WO-2012/021819 A2 | 2/2012 |
| WO | WO-2012/028317 A1 | 3/2012 |
| WO | WO-2012/028319 A1 | 3/2012 |
| WO | WO-2012/037457 A1 | 3/2012 |
| WO | WO-2012/052955 A1 | 4/2012 |
| WO | WO-2012/054071 A1 | 4/2012 |
| WO | WO-2012/054831 A2 | 4/2012 |
| WO | WO-2012/061779 A1 | 5/2012 |
| WO | WO-2012/063257 A2 | 5/2012 |
| WO | WO-2012/069175 A1 | 5/2012 |
| WO | WO-2012/076907 A2 | 6/2012 |
| WO | WO-2012/077110 A2 | 6/2012 |
| WO | WO-2012/085236 A1 | 6/2012 |
| WO | WO-2012/085656 A2 | 6/2012 |
| WO | WO-2012/085657 A2 | 6/2012 |
| WO | WO-2012/087377 A1 | 6/2012 |
| WO | WO-2012/098281 A2 | 7/2012 |
| WO | WO-2012/106343 A2 | 8/2012 |

(56) References Cited

FOREIGN PATENT DOCUMENTS

| WO | WO-2012/112933 A1 | 8/2012 |
| WO | WO-2012/112952 A1 | 8/2012 |
| WO | WO-2012/116278 A1 | 8/2012 |
| WO | WO-2012/116279 A1 | 8/2012 |
| WO | WO-2012/121461 A1 | 9/2012 |
| WO | WO-2012/127506 A1 | 9/2012 |
| WO | WO-2012/131463 A2 | 10/2012 |
| WO | WO-2012/139191 A1 | 10/2012 |
| WO | WO-2012/177986 A2 | 12/2012 |
| WO | WO-2013/000578 A1 | 1/2013 |
| WO | WO-2013/003845 A1 | 1/2013 |
| WO | WO-2013/010880 A1 | 1/2013 |
| WO | WO-2013/010881 A1 | 1/2013 |
| WO | WO-2013/015545 A1 | 1/2013 |
| WO | WO-2013/017234 A1 | 2/2013 |
| WO | WO-2013/038267 A1 | 3/2013 |
| WO | WO-2013/038268 A1 | 3/2013 |
| WO | WO-2013/050539 A2 | 4/2013 |
| WO | WO-2013/057570 A2 | 4/2013 |
| WO | WO-2013/058496 A1 | 4/2013 |
| WO | WO-2013/059805 A1 | 4/2013 |
| WO | WO-2013/061161 A2 | 5/2013 |
| WO | WO-2013/070617 A1 | 5/2013 |
| WO | WO-2013/072395 A1 | 5/2013 |
| WO | WO-2013/077851 A1 | 5/2013 |
| WO | WO-2013/082308 A1 | 6/2013 |
| WO | WO-2013/083710 A1 | 6/2013 |
| WO | WO-2013/084059 A1 | 6/2013 |
| WO | WO-2013/093877 A2 | 6/2013 |
| WO | WO-2013/103537 A1 | 7/2013 |
| WO | WO-2013/119231 A1 | 8/2013 |
| WO | WO-2013/128276 A2 | 9/2013 |
| WO | WO-2013/128447 A1 | 9/2013 |
| WO | WO-2013/136078 A1 | 9/2013 |
| WO | WO-2013/138118 A1 | 9/2013 |
| WO | WO-2013/151638 A1 | 10/2013 |
| WO | WO-2013/155430 A1 | 10/2013 |
| WO | WO-2013/158810 A1 | 10/2013 |
| WO | WO-2013/158814 A1 | 10/2013 |
| WO | WO-2013/170052 A1 | 11/2013 |
| WO | WO-2013/171146 A1 | 11/2013 |
| WO | WO-2013/175511 A1 | 11/2013 |
| WO | WO-2014/001268 A1 | 1/2014 |
| WO | WO-2014/001904 A1 | 1/2014 |
| WO | WO-2014/001905 A1 | 1/2014 |
| WO | WO-2014/006004 A1 | 1/2014 |
| WO | WO-2014/011830 A1 | 1/2014 |
| WO | WO-2014/025638 A1 | 2/2014 |
| WO | WO-2014/045305 A1 | 3/2014 |
| WO | WO-2014/047731 A1 | 4/2014 |
| WO | WO-2014/059512 A1 | 4/2014 |

OTHER PUBLICATIONS

Ashland, Klucel hydroxypropylcellulose, Physical and chemical properties. http://www.ashland.com/Ashland/Static/Documents/ASI/PC_11229_Klucel_HPC.pdf. 24 pages. (2012).
Bartholomaus et al., New Abuse Deterrent Formulation (ADF) Technology for Immediate-Release Opioids. Drug Development & Delivery. 2013;13(8):76-81.
BASF, Technical Bulletin, Pluronic Block Copolymer NF Grades (Poloxamer NF Grades). BASF Corporation, 2 pages, (2004).
Benziger et al., Differential effects of food on the bioavailability of controlled-release oxycodone tablets and immediate-release oxycodone solution. J Pharm Sci. Apr. 1996;85(4):407-10.
Borini et al., Hot melt granulation of coarse pharmaceutical powders in a spouted bed. Powder Technology. 2009;189(3):520-527.
Dahl et al., Mechanisms to control drug release from pellets coated with a silicone elastomer aqueous dispersion. Pharm Res. Mar. 1992;9(3):398-405.
Djuris et al., Application of quality by design concepts in the development of fluidized bed granulation and tableting processes. J Pharm Sci. Jun. 2013;102(6):1869-1882.
Dow, Polyox, Water-Soluble Resins. Unique Resins for Binding, Lubricity, Adhesion and Emollient Performance. www.polyox.com. 24 pages, Mar. 2002.
Gazzaniga et al., A novel injection-molded capsular device for oral pulsatile delivery based on swellable/erodible polymers. AAPS PharmSciTech. 2011;12(1):295-303.
Gohel et al., Fabrication and Evaluation of Bi-layer Tablet Containing Conventional Paracetamol and Modified Release Diclofenac Sodium. Indian J Pharm Sci. Mar. 2010;72(2):191-6.
Gosai et al., Bioequivalence of oxycodone hydrochoride extended release tablets to marketed reference products OxyContin® in Canada and US. Int J Clin Pharmacol Ther. Nov. 2013;51(11):895-907.
Harris et al., Abuse potential, pharmacokinetics, pharmacodynamics, and safety of intranasally administered crushed oxycodone HCl abuse-deterrent controlled-release tablets in recreational opioid users. J Clin Pharmacol. Apr. 2014;54(4):468-77.
King, Tablets, Capsules, and Pills. Remington's Pharmaceutical Science, Mack Publishing Company, Pennsylvania, 15th Edition, Alfonso R. Gennaro (Ed.). Chapter 89, pp. 1576-1607, (1975).
MP Biomedicals. Lecithin Melting Point Properties. Retrieved online at: http://www.mpbio.com/product.php?pid=02151540&country=223. 2 pages, (2010).
Sako et al., Influence of water soluble fillers in hydroxypropylmethylcellulose matrices on in vitro and in vivo drug release. J Control Release. May 17, 2002;81(1-2):165-72.
Sako et al., Relationship between gelation rate of controlled-release acetaminophen tablets containing polyethylene bride and colonic drug release in dogs. Pharmaceutical Research 1996;13(4):594-598.
Shah et al., Polyox (Polyethylene Oxide)—Applications in Pharma Industry. Pharmainfo.net. 15 pages, (2016).
Sigma-Aldrich, Kolliphor P 407, oxyethylene 7135-74.9%. http://www.sigmaaldrich.com/catalog/product/sigma/62035?lang=en&region=US#. 3 pages. Assessed May 6, 2015.
Soininen et al., Dissolution rate of different kinds of granulated micronized paracetamol with adjuvant incorporated either inter- or intragranularly. Acta Pharmaceutica Fennica. 1981;90(2):153-162.
Soininen et al., Effect of polyethylene glycol 20000 on bioavailability of micronized and crystalline paracetamol. Acta Pharmaceutica Fennica. 1981;90(4):381-386.
Stambaugh et al., Double-blind, randomized comparison of the analgesic and pharmacokinetic profiles of controlled- and immediate-release oral oxycodone in cancer pain patients. J Clin Pharmacol. May 2001;41(5):500-6.
Sunshine et al., Analgesic efficacy of controlled-release oxycodone in postoperative pain. J Clin Pharmacol. Jul. 1996;36(7):595-603.
Third Party Observation for Application No. PCT/US2014/050737, dated Sep. 8, 2015, 3 pages.
Treffer et al., Pellet Production by Hot Melt Extrusion and Die Face Pelletising. Pharmaceutical Solid State Research Cluster, May 7, 2013, 5 pages.
Upadhye et al., Polyethylene Oxide and Ethylcellulose for Tamper Resistance and Controlled Drug Delivery. Melt Extrusion, AAPS Advanceds in the Pharmaceutical Sciences Series 9, Chapter 6. Oct. 11, 2013;pp. 145-158.
US Pharmacopeia, 711 Dissolution. The United States Pharmacopeial Convention. 8 pages, Dec. 1, 2011.
Wikipedia, Poloxamer. Retrieved online at: https://en.wikipedia.org/wiki/Poloxamer. 4 Pages, May 15, 2016.
International Search Report and Written Opinion for Application No. PCT/US2014/070949, dated Apr. 15, 2015, 10 Pages.
International Search Report and Written Opinion for Application No. PCT/US2014/70942, dated Mar. 18, 2015, 10 Pages.
International Search Report for Application No. PCT/US2015/039336, dated Oct. 7, 2015, 2 pages.
International Search Report for Application No. PCT/US2014/050737, dated Jan. 22, 2015, 5 pages.

* cited by examiner

FIG. 9
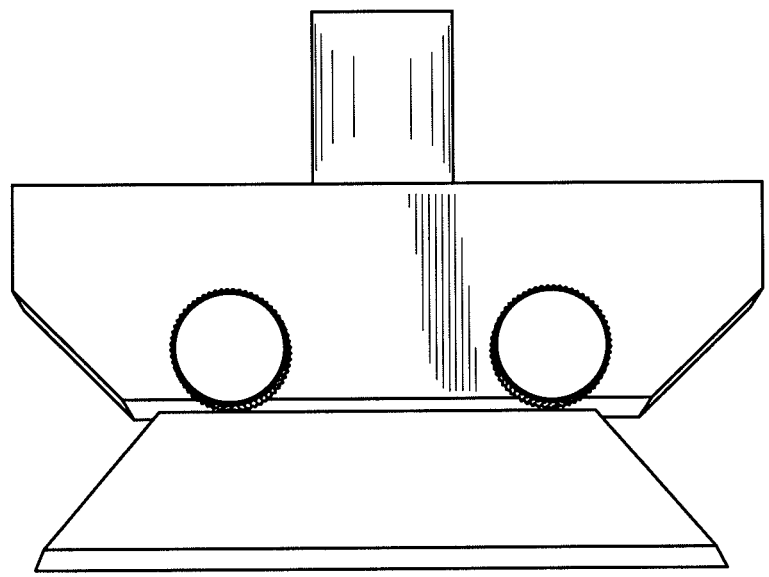
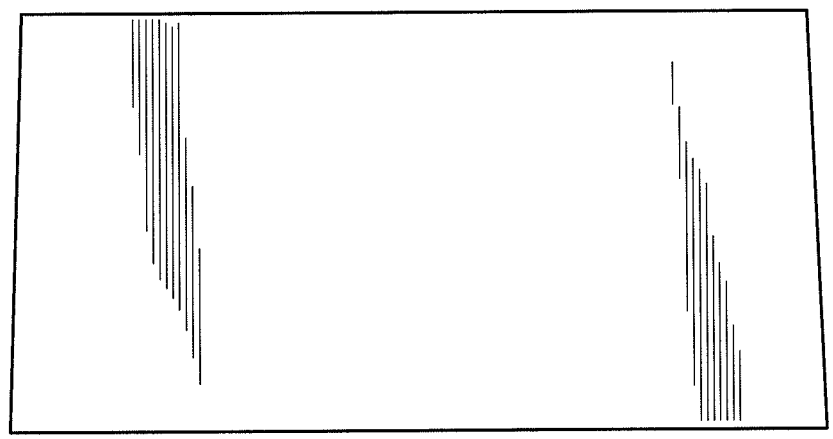

FIG. 10A

Cutting Force - Razor Blade

| Replicate | Roxicodone 15mg | PMRS IR 5mg ADF | PMRS IR 30mg ADF | PMRS ER 10mg ADF | PMRS ER 80mg ADF | Opana ER 5mg | Opana ER 40mg | Oxycontin 10mg | Oxycontin 40mg | Oxycontin 60mg | Oxycontin 80mg |
|---|---|---|---|---|---|---|---|---|---|---|---|
| 1 | 12 | 37 | 41 | 77 | 90 | 133 | 118 | 59 | 37 | 46 | 46 |
| 2 | 9 | 44 | 46 | 79 | 86 | 135 | 120 | 50 | 52 | 47 | 49 |
| 3 | 11 | 43 | 54 | 85 | 87 | 133 | 136 | 42 | 40 | 45 | 52 |
| 4 | 10 | 40 | 49 | 64 | 86 | 119 | 127 | 42 | 44 | 43 | 46 |
| 5 | 10 | 49 | 46 | 85 | 76 | 133 | 138 | 43 | 43 | 44 | 53 |
| 6 | 12 | 59 | 50 | 83 | 90 | 131 | 129 | 44 | 43 | 45 | 45 |
| 7 | 10 | 42 | 36 | 80 | 93 | 129 | 141 | 47 | 44 | 46 | 45 |
| 8 | 11 | 38 | 44 | 79 | 81 | 127 | 142 | 46 | 39 | 45 | 48 |
| 9 | 11 | 36 | 54 | 82 | 89 | 116 | 135 | 40 | 44 | 42 | 48 |
| 10 | 10 | 51 | 49 | 81 | 89 | 117 | 125 | 41 | 43 | 53 | 47 |
| Minimum | 9 | 36 | 36 | 64 | 76 | 116 | 118 | 40 | 37 | 42 | 45 |
| Maximum | 12 | 59 | 54 | 85 | 93 | 135 | 142 | 59 | 52 | 53 | 53 |
| Average | 10 | 44 | 47 | 79 | 87 | 127 | 131 | 45 | 43 | 46 | 48 |
| %RSD | 9.3 | 16.5 | 11.9 | 7.7 | 5.7 | 5.7 | 6.6 | 12.2 | 9.4 | 6.9 | 5.7 |

FIG. 10B

| | | | | Cutting Force - Fracture Wedge Set | | | | | | | |
|---|---|---|---|---|---|---|---|---|---|---|---|
| | | | | Sample Name | | | | | | | |
| Replicate | Roxicodone 15mg | PMRS IR 5mg ADF | PMRS IR 30mg ADF | PMRS ER 10mg ADF | PMRS ER 80mg ADF | Opana ER 5mg | Opana ER 40mg | Oxycontin 10mg | Oxycontin 40mg | Oxycontin 60mg | Oxycontin 80mg |
| 1 | 18 | 60 | 59 | 110 | 127 | 156 | 132 | 144 | 92 | 108 | 97 |
| 2 | 21 | 66 | 64 | 109 | 114 | 156 | 142 | 153 | 94 | 103 | 97 |
| 3 | 22 | 66 | 68 | 115 | 108 | 155 | 143 | 156 | 85 | 104 | 99 |
| 4 | 18 | 72 | 63 | 110 | 124 | 145 | 138 | 157 | 92 | 102 | 96 |
| 5 | 18 | 65 | 64 | 104 | 112 | 161 | 142 | 160 | 98 | 111 | 91 |
| 6 | 19 | 67 | 63 | 105 | 110 | 151 | 137 | 154 | 92 | 107 | 97 |
| 7 | 20 | 68 | 62 | 110 | 113 | 156 | 143 | 154 | 100 | 100 | 90 |
| 8 | 19 | 74 | 62 | 96 | 112 | 158 | 144 | 140 | 95 | 104 | 92 |
| 9 | 16 | 69 | 64 | 101 | 118 | 163 | 150 | 148 | 93 | 102 | 91 |
| 10 | 20 | 64 | 64 | 92 | 108 | 158 | 144 | 127 | 91 | 104 | 98 |
| Minimum | 16 | 60 | 59 | 92 | 108 | 145 | 132 | 127 | 85 | 100 | 90 |
| Maximum | 22 | 74 | 68 | 115 | 127 | 163 | 150 | 160 | 100 | 111 | 99 |
| Average | 19 | 67 | 63 | 105 | 115 | 156 | 141 | 149 | 93 | 104 | 95 |
| %RSD | 9.0 | 6.1 | 3.6 | 6.7 | 5.7 | 3.3 | 3.5 | 6.6 | 4.4 | 3.2 | 3.4 |

FIG. 11A

Particle Size Analysis - TE96

| Location | Replicate | Roxicodone 15mg | PMRS IR 5mg ADF | PMRS IR 30mg ADF | PMRS ER 10mg ADF | PMRS ER 80mg ADF | Opana ER 5mg | Opana ER 40mg | Oxycontin 10mg | Oxycontin 40mg | Oxycontin 60mg | Oxycontin 80mg |
|---|---|---|---|---|---|---|---|---|---|---|---|---|
| Pan (<500μm) % | 1 | 80.684 | 7.616 | 10.491 | 5.116 | 7.283 | -1.728 | 3.479 | 23.075 | 11.918 | 21.636 | 25.919 |
| | 2 | 80.408 | 26.246 | 7.367 | 5.430 | 9.525 | 8.614 | 3.376 | 6.997 | 13.963 | 18.173 | 24.828 |
| | 3 | 76.990 | 22.213 | 16.391 | -5.914 | 7.401 | 0.000 | 3.320 | 18.485 | 23.140 | 17.785 | 23.150 |
| | Minimum | 76.990 | 7.616 | 7.367 | -5.914 | 7.283 | -1.728 | 3.320 | 6.997 | 11.918 | 17.785 | 23.150 |
| | Maximum | 80.684 | 26.246 | 16.391 | 5.430 | 9.525 | 8.614 | 3.479 | 23.075 | 23.140 | 21.636 | 25.919 |
| | Average | 79.361 | 18.692 | 11.416 | 1.544 | 8.070 | 2.295 | 3.392 | 16.185 | 16.340 | 19.198 | 24.632 |
| | %RSD | 2.593 | 52.436 | 40.141 | 418.385 | 15.633 | 241.364 | 2.375 | 51.168 | 36.578 | 11.043 | 5.662 |
| 35 Mesh (≥500μm) % | 1 | 19.316 | 92.384 | 89.509 | 94.884 | 92.717 | 101.728 | 96.521 | 76.925 | 88.082 | 78.364 | 74.081 |
| | 2 | 19.592 | 73.754 | 92.633 | 94.570 | 90.475 | 91.386 | 96.624 | 93.003 | 86.037 | 81.827 | 75.172 |
| | 3 | 23.010 | 77.787 | 83.609 | 105.914 | 92.599 | 100.000 | 96.680 | 81.515 | 76.860 | 82.215 | 76.850 |
| | Minimum | 19.316 | 73.754 | 83.609 | 94.570 | 90.475 | 91.386 | 96.521 | 76.925 | 76.860 | 78.364 | 74.081 |
| | Maximum | 23.010 | 92.384 | 92.633 | 105.914 | 92.717 | 101.728 | 96.680 | 93.003 | 88.082 | 82.215 | 76.850 |
| | Average | 20.639 | 81.308 | 88.584 | 98.456 | 91.930 | 97.705 | 96.608 | 83.815 | 83.660 | 80.802 | 75.368 |
| | %RSD | 9.970 | 12.054 | 5.173 | 6.562 | 1.372 | 5.670 | 0.083 | 9.881 | 7.144 | 2.624 | 1.851 |

FIG. 11B

Particle Size Analysis - Mr. Coffee Grinder

| Location | Replicate | Sample Name | | | | | | | | | | |
|---|---|---|---|---|---|---|---|---|---|---|---|---|
| | | Roxicodone 15mg | PMRS IR 5mg ADF | PMRS IR 30mg ADF | PMRS ER 10mg ADF | PMRS ER 80mg ADF | Opana ER 5mg | Opana ER 40mg | Oxycontin 10mg | Oxycontin 40mg | Oxycontin 60mg | Oxycontin 80mg |
| Pan (<500µm) % | 1 | 89.619 | 39.831 | 43.776 | 16.536 | 21.551 | 15.289 | 3.092 | 19.223 | 38.264 | 40.970 | 44.932 |
| | 2 | 93.162 | 34.900 | 47.189 | 17.891 | 26.499 | 11.785 | 15.311 | 22.266 | 41.150 | 37.439 | 45.045 |
| | 3 | 89.064 | 11.813 | 31.352 | 5.243 | 16.439 | 4.725 | 14.196 | 29.219 | 36.318 | 47.452 | 35.878 |
| | Minimum | 89.064 | 11.813 | 31.352 | 5.243 | 16.439 | 4.725 | 3.092 | 19.223 | 36.318 | 37.439 | 35.878 |
| | Maximum | 93.162 | 39.831 | 47.189 | 17.891 | 26.499 | 15.289 | 15.311 | 29.219 | 41.150 | 47.452 | 45.045 |
| | Average | 90.615 | 28.848 | 40.773 | 13.223 | 21.496 | 10.599 | 10.867 | 23.569 | 38.577 | 41.954 | 41.952 |
| | %RSD | 2.453 | 51.849 | 20.442 | 52.518 | 23.401 | 50.765 | 62.171 | 21.739 | 6.303 | 12.106 | 12.538 |
| 35 Mesh (≥500µm) % | 1 | 10.381 | 60.169 | 56.224 | 83.464 | 78.449 | 84.711 | 96.908 | 80.777 | 61.736 | 59.030 | 55.068 |
| | 2 | 6.838 | 65.100 | 52.811 | 82.109 | 73.501 | 88.215 | 84.689 | 77.734 | 58.850 | 62.561 | 54.955 |
| | 3 | 10.936 | 88.187 | 68.648 | 94.757 | 83.561 | 95.275 | 85.804 | 70.781 | 63.682 | 52.548 | 64.122 |
| | Minimum | 6.838 | 60.169 | 52.811 | 82.109 | 73.501 | 84.711 | 84.689 | 70.781 | 58.850 | 52.548 | 54.955 |
| | Maximum | 10.936 | 88.187 | 68.648 | 94.757 | 83.561 | 95.275 | 96.908 | 80.777 | 63.682 | 62.561 | 64.122 |
| | Average | 9.385 | 71.152 | 59.227 | 86.777 | 78.504 | 89.401 | 89.133 | 76.431 | 61.423 | 58.046 | 58.048 |
| | %RSD | 23.686 | 21.022 | 14.072 | 8.003 | 6.408 | 6.019 | 7.580 | 6.704 | 3.959 | 8.750 | 9.061 |

FIG. 12A

| Product | % Loss - Grinding | % Loss - Sifting to Grinding | Total % Loss |
|---|---|---|---|
| Roxicodone 15mg - 1 | 16.52 | -21.93 | -1.79 |
| Roxicodone 15mg - 2 | 12.18 | -8.18 | 4.99 |
| Roxicodone 15mg - 3 | 33.74 | 2.70 | 35.53 |

| Product | % Loss - Grinding | % Loss - Sifting to Grinding | Total % Loss |
|---|---|---|---|
| PMRS IR 5mg ADF - 1 | 1.92 | 9.63 | 11.37 |
| PMRS IR 5mg ADF - 2 | 11.36 | -11.45 | 1.22 |
| PMRS IR 5mg ADF - 3 | 0.78 | -6.58 | -5.75 |

| Product | % Loss - Grinding | % Loss - Sifting to Grinding | Total % Loss |
|---|---|---|---|
| PMRS IR 30mg ADF - 1 | -0.33 | 5.27 | 4.96 |
| PMRS IR 30mg ADF - 2 | 3.59 | 5.72 | 9.11 |
| PMRS IR 30mg ADF - 3 | -0.17 | 20.47 | 20.33 |

| Product | % Loss - Grinding | % Loss - Sifting to Grinding | Total % Loss |
|---|---|---|---|
| PMRS ER 10mg ADF - 1 | 1.38 | 3.46 | 4.79 |
| PMRS ER 10mg ADF - 2 | 5.13 | 5.76 | 10.59 |
| PMRS ER 10mg ADF - 3 | 4.24 | 13.55 | 17.22 |

FIG. 12B

| Product | % Loss - Grinding | % Loss - Sifting to Grinding | Total % Loss |
|---|---|---|---|
| PMRS ER 80mg ADF - 1 | -0.11 | 4.42 | 4.31 |
| PMRS ER 80mg ADF - 2 | 0.74 | -0.73 | 0.01 |
| PMRS ER 80mg ADF - 3 | 0.99 | 4.83 | 5.78 |

| Product | % Loss - Grinding | % Loss - Sifting to Grinding | Total % Loss |
|---|---|---|---|
| Opana ER 5mg - 1 | 7.03 | 5.89 | 12.50 |
| Opana ER 5mg - 2 | 15.59 | -5.85 | 10.65 |
| Opana ER 5mg - 3 | 9.05 | 5.30 | 13.87 |

| Product | % Loss - Grinding | % Loss - Sifting to Grinding | Total % Loss |
|---|---|---|---|
| Opana ER 40mg - 1 | 9.75 | 4.54 | 13.84 |
| Opana ER 40mg - 2 | 8.05 | 2.61 | 10.45 |
| Opana ER 40mg - 3 | 6.91 | 2.28 | 9.03 |

| Product | % Loss - Grinding | % Loss - Sifting to Grinding | Total % Loss |
|---|---|---|---|
| Oxycontin 10mg - 1 | 3.59 | -15.55 | -11.41 |
| Oxycontin 10mg - 2 | 3.62 | 5.32 | 8.74 |
| Oxycontin 10mg - 3 | 2.81 | -6.29 | -3.30 |

FIG. 12C

| Product | % Loss - Grinding | % Loss - Sifting to Grinding | Total % Loss |
|---|---|---|---|
| Oxycontin 40mg - 1 | 5.39 | 4.89 | 10.01 |
| Oxycontin 40mg - 2 | 7.16 | 1.96 | 8.98 |
| Oxycontin 40mg - 3 | 8.01 | -8.78 | -0.07 |

| Product | % Loss - Grinding | % Loss - Sifting to Grinding | Total % Loss |
|---|---|---|---|
| Oxycontin 60mg - 1 | 4.99 | -4.67 | 0.55 |
| Oxycontin 60mg - 2 | 5.88 | -0.96 | 4.98 |
| Oxycontin 60mg - 3 | 5.09 | -1.87 | 3.31 |

| Product | % Loss - Grinding | % Loss - Sifting to Grinding | Total % Loss |
|---|---|---|---|
| Oxycontin 80mg - 1 | 8.01 | -8.72 | -0.01 |
| Oxycontin 80mg - 2 | 6.85 | -6.64 | 0.66 |
| Oxycontin 80mg - 3 | 5.99 | -5.43 | 0.89 |

FIG. 12D

| Product | % Loss - Grinding | % Loss - Sifting to Grinding | Total % Loss |
|---|---|---|---|
| Roxicodone 15mg - 1 | 27.59 | 9.64 | 34.57 |
| Roxicodone 15mg - 2 | 19.43 | 12.40 | 29.42 |
| Roxicodone 15mg - 3 | 12.05 | 2.71 | 14.43 |

| Product | % Loss - Grinding | % Loss - Sifting to Grinding | Total % Loss |
|---|---|---|---|
| PMRS IR 5mg ADF - 1 | -1.37 | -23.09 | -24.77 |
| PMRS IR 5mg ADF - 2 | 0.11 | -1.14 | -1.03 |
| PMRS IR 5mg ADF - 3 | -1.53 | 17.35 | 16.08 |

| Product | % Loss - Grinding | % Loss - Sifting to Grinding | Total % Loss |
|---|---|---|---|
| PMRS IR 30mg ADF - 1 | 1.77 | -15.06 | -13.02 |
| PMRS IR 30mg ADF - 2 | 3.34 | -9.79 | -6.13 |
| PMRS IR 30mg ADF - 3 | 3.03 | 1.91 | 4.87 |

| Product | % Loss - Grinding | % Loss - Sifting to Grinding | Total % Loss |
|---|---|---|---|
| PMRS ER 10mg ADF - 1 | -6.94 | 1.43 | -5.42 |
| PMRS ER 10mg ADF - 2 | 1.10 | -0.65 | 0.46 |
| PMRS ER 10mg ADF - 3 | 2.03 | 5.59 | 7.51 |

FIG. 12E

| Product | % Loss - Grinding | % Loss - Sifting to Grinding | Total % Loss |
|---|---|---|---|
| PMRS ER 80mg ADF - 1 | 0.53 | -1.19 | -0.66 |
| PMRS ER 80mg ADF - 2 | 0.82 | -7.15 | -6.27 |
| PMRS ER 80mg ADF - 3 | 1.21 | 0.88 | 2.07 |

| Product | % Loss - Grinding | % Loss - Sifting to Grinding | Total % Loss |
|---|---|---|---|
| Opana ER 5mg - 1 | 3.21 | -13.76 | -10.11 |
| Opana ER 5mg - 2 | 0.38 | -2.63 | -2.25 |
| Opana ER 5mg - 3 | 6.95 | -1.69 | 5.38 |

| Product | % Loss - Grinding | % Loss - Sifting to Grinding | Total % Loss |
|---|---|---|---|
| Opana ER 40mg - 1 | 1.49 | 4.09 | 5.52 |
| Opana ER 40mg - 2 | -0.64 | -10.24 | -10.95 |
| Opana ER 40mg - 3 | 2.75 | -9.35 | -6.34 |

| Product | % Loss - Grinding | % Loss - Sifting to Grinding | Total % Loss |
|---|---|---|---|
| Oxycontin 10mg - 1 | 2.26 | -2.50 | -0.18 |
| Oxycontin 10mg - 2 | -7.47 | -6.27 | -14.21 |
| Oxycontin 10mg - 3 | 4.99 | -0.17 | 4.83 |

FIG. 12F

| Product | % Loss - Grinding | % Loss - Sifting to Grinding | Total % Loss |
|---|---|---|---|
| Oxycontin 40mg - 1 | 9.44 | -4.29 | 5.55 |
| Oxycontin 40mg - 2 | 5.45 | -5.20 | 0.53 |
| Oxycontin 40mg - 3 | 3.21 | -3.61 | -0.28 |

| Product | % Loss - Grinding | % Loss - Sifting to Grinding | Total % Loss |
|---|---|---|---|
| Oxycontin 60mg - 1 | 4.24 | 3.03 | 7.14 |
| Oxycontin 60mg - 2 | 2.56 | 5.45 | 7.87 |
| Oxycontin 60mg - 3 | 3.57 | -5.04 | -1.29 |

| Product | % Loss - Grinding | % Loss - Sifting to Grinding | Total % Loss |
|---|---|---|---|
| Oxycontin 80mg - 1 | 7.57 | -5.50 | 2.49 |
| Oxycontin 80mg - 2 | 3.32 | -6.40 | -2.87 |
| Oxycontin 80mg - 3 | -8.30 | 10.94 | 3.55 |

FIG. 13

PMRS IR 30mg Oxycodone HCl (100mg Pill Weight) Testing Summary

| Sample | Acetate | | Dissolution (% Dissolved in 45 minutes)* | %LC (Assay) | %LC (Purity) | | | Dye | | |
|---|---|---|---|---|---|---|---|---|---|---|
| | Type | % w/w | | | EtOH Extraction | H₂O Extraction | % w/w | Color following Nylon Filtration in EtOH** | Color following Nylon Filtration in H₂O** | |
| 1 | None | N/A | 92 | 98 | 61 | 32 | 0.1 | 0 | 0 | |
| 2 | Calcium | 10 | 84 | 98 | 49 | 28 | 1.0 | 0 | 0 | |
| 3 | Calcium | 10 | 93 | 97 | 32 | 29 | 4.0 | 1 | 5 | |

* Q ≥70% (Specification = Q + 5% (75%)) dissolved in 45 minutes

** Color scale designation: 0 = no color, 5 = dark, significant color

* Roxicodone® batch % particles ≥ 500μm is statiscally different (lower) than PMRS ADF IR batches.

* Oxycontin® batch % particles ≥ 500μm is statiscally different (lower) than PMRS ADF ER batches and Opana® batches when combining all dosages tested by each manufacturer.

EXTRUDED IMMEDIATE RELEASE ABUSE DETERRENT PILL

CROSS-REFERENCE TO RELATED APPLICATIONS

This application is a divisional application of U.S. patent application Ser. No. 14/457,714, filed on Aug. 12, 2014, which claims priority under 35 U.S.C. § 119(e) to U.S. Provisional Application No. 61/864,926, filed on Aug. 12, 2013, and 61/980,242, filed on Apr. 16, 2014, the entire contents of each of the above-referenced applications are incorporated herein by reference.

FIELD OF THE TECHNOLOGY

The present disclosure relates to an oral immediate release, abuse deterrent pill prepared using a hot melt extrusion process and a forming unit. The pill contains at least one abuse deterrent mechanism to reduce abuse by non-oral administration routes, e.g. intranasal and/or intravenous. The extrusion process and forming unit are designed to efficiently prepare the abuse deterrent pill under conditions that reduce, or substantially eliminate, degradation of the active substance.

BACKGROUND OF THE INVENTION

FDA-approved drugs are provided in many different forms based on the type of active substance, the indication treated and the preferred route of administration. These forms include enteral formulations (e.g., tablets, capsules or pills), parenteral formulations (e.g., injectable formulations such as intravenous, subcutaneous, intramuscular and intraarticular), liquid formulations (e.g., elixirs), lyophilized formulations and topical formulations. A majority of the FDA-approved drugs are currently available in enteral form, as either a tablet or capsule.

The production of pharmaceutical drugs in pill form by hot melt extrusion is relatively uncommon. While the idea of dissolving drugs in polymers and using extrusion to produce a pill has been known for decades, only a handful of FDA-approved drugs are extruded. Recently, extrusion techniques have been investigated for preparing abuse deterrent formulations. For example, U.S. Pat. No. 8,075,872 (assigned to Grunenthal GmbH) is directed to a thermoshaped abuse deterrent dosage form prepared with the assistance of an extruder. The extrudate may be shaped by the assistance of contra-rotating calendar rolls, and singulated by conventional means such as chopping. U.S. Pat. No. 8,383,152 (assigned to Grunenthal GmbH) is directed to a controlled release pharmaceutical dosage form that may also be prepared by extrusion and shaped by a calendaring process. U.S. 2007/0190142 (assigned to Abbott GmbH) is directed to a sustained release abuse deterrent dosage form prepared by extrusion and shaping the extrudate into a dosage form without a milling or multi-particulating step.

SUMMARY OF THE INVENTION

The present disclosure relates to an abuse deterrent pill prepared using a hot melt extrusion process and a forming unit. The formulation contains an active substance susceptible to abuse and at least one abuse deterrent mechanism to reduce abuse by non-oral administration routes (e.g., intranasal and/or intravenous). The abuse deterrent pill is designed for immediate release of the active substance upon oral administration. The method of preparing the pill utilizes a hot melt extrusion process coupled with an in-line forming unit which eliminates the need for traditional extrusion processing steps, such as chopping the extrudate and molding the cut extrudate into a final form. The hot melt extrusion process and forming unit are operated under conditions that reduce, or substantially eliminate degradation of the active substance.

In one embodiment, the present disclosure relates to a directly-formed oral, extruded, immediate release, abuse deterrent pill comprising an active substance susceptible to abuse, a matrix agent and a plasticizer, wherein the pill is directly formed from a hot melt extrusion process, preferably without further processing (e.g., a cutting step). The extrudate may be re-sized or re-shaped, without cutting, prior to forming (e.g., rope sizer).

In another embodiment, the present disclosure relates to an oral, immediate release, abuse deterrent pill comprising an active substance susceptible to abuse, a matrix agent and a plasticizer, wherein the active substance susceptible to abuse has an immediate release profile, and wherein the composition includes a physical barrier to reduce abuse. In some embodiments, the physical barrier can reduce abuse by techniques such as pulverizing and swallowing, pulverizing and snorting, or pulverizing and injecting. In other embodiments, the physical barrier can reduce abuse by forming a hydrogel upon exposure to an aqueous or semi-aqueous solution. In some embodiments, the semi-aqueous solution is a 95% ethanol/5% water solution.

In another embodiment, the present disclosure relates to a process for the production of an oral, immediate release, abuse deterrent pill containing at least one active substance susceptible to abuse comprising processing a uniform blend of the at least one active substance susceptible to abuse, a matrix agent and a plasticizer by hot melt extrusion to form an extrudate. The extrudate may therein be formed into the pill using a forming unit.

In another embodiment, the present disclosure relates to a process for the production of an oral, immediate release, abuse deterrent pill containing at least one active substance susceptible to abuse comprising one or more of the following steps: combining the at least one active substance susceptible to abuse, a matrix agent and a plasticizer in a hopper to form a mixture; blending the mixture in the hopper until a uniform blend is achieved; monitoring the mixture during blending using a process analytical technique to determine when a uniform blend is achieved; feeding the uniform blend into an extruder; processing the uniform blend by hot melt extrusion to produce an extrudate; transferring the extrudate to a forming unit using a transfer unit capable of controlling the temperature, pressure, environment and/or shape of the extrudate; forming the extrudate using the forming unit into the pill; and determining the quality, volume and weight of the pill using an optical inspection technique.

In another embodiment, the present disclosure relates to a method of treating pain comprising administering to an individual in need thereof a therapeutically effective amount of an abuse deterrent formulation prepared using a hot melt extrusion process and a forming unit as described herein.

BRIEF DESCRIPTION OF THE DRAWINGS

FIG. 9 shows equipment capable of executing a "cutting force" analysis including a razor blade attachment.

FIGS. 10A and 10B show cutting force data tables for the razor blade and the fracture wedge attachments.

FIGS. 11A and 11B show particle size analyses for exemplary formulations described in the present disclosure.

FIGS. 12A, 12B, 12C, 12D, 12E and 12F show grinding results for exemplary formulations described in the present disclosure.

FIG. 13 shows the results of the dissolution, purity and dye evaluation tests on exemplary formulations.

DETAILED DESCRIPTION

Figure 1:
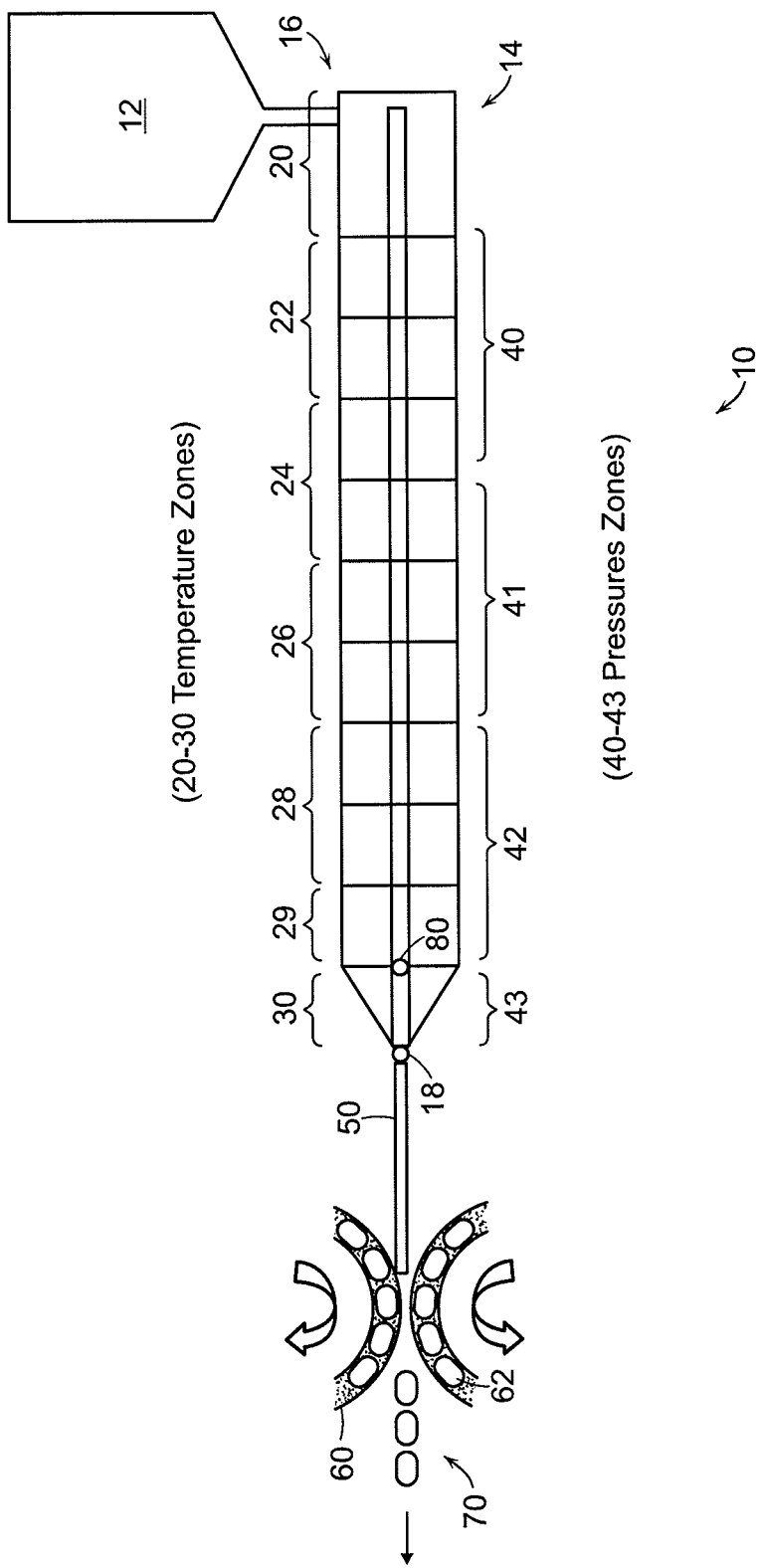
FIG. 1 shows an embodiment of the extruder (14) and forming unit (60). The extruder has multiple temperature zones (e.g., 20-30) and pressure zones (e.g., 20, 40-43) to control the formation of a uniform extrudate under conditions that reduce, or substantially eliminate, degradation of the active substance.

Abuse of prescription drugs, particularly opioids, is a serious and growing public health concern. To address this concern, new formulations are being developed that contain abuse-deterrent properties. Abuse deterrent properties include properties that make product manipulation more difficult or make abuse of the manipulated product less attractive or rewarding.

Recently the FDA issued a draft guidance for industry related to formulations having abuse deterrent properties. *Guidance for Industry: Abuse Deterrent Opioids—Evaluation and Labeling*, U.S. Department of Health and Human Services, FDA, CDER, January 2013, the entire contents of which are incorporated herein by reference. These guidelines separate abuse deterrent formulations into six categories, including: physical/chemical barriers, agonist/antagonist combinations, aversion, delivery system, prodrug, or a combination of the aforementioned. As described by the FDA guidance, the categories are:

Physical/Chemical barriers—Physical barriers can prevent chewing, pulverizing, cutting, grating, or grinding. Chemical barriers can resist extraction of the opioid using common solvents like water, alcohol, or other organic solvents. Physical and chemical barriers can change the physical form of an oral drug rendering it less amenable to abuse.

Agonist/Antagonist combinations—An opioid antagonist can be added to interfere with, reduce, or defeat the euphoria associated with abuse. The antagonist can be sequestered and released only upon manipulation of the product. For example, a drug product may be formulated such that the substance that acts as an antagonist is not clinically active when the product is swallowed but becomes active if the product is crushed and injected or snorted.

Aversion—Substances can be combined to produce an unpleasant effect if the dosage form is manipulated prior to ingestion or a higher dosage than directed is used.

Delivery System (including depot injectable formulations and implants)—Certain drug release designs or the method of drug delivery can offer resistance to abuse. For example, a sustained-release depot injectable formulation that is administered intramuscularly or a subcutaneous implant can be more difficult to manipulate.

Prodrug—A prodrug that lacks opioid activity until transformed in the gastrointestinal tract can be unattractive for intravenous injection or intranasal routes of abuse.

Combination—Two or more of the above methods can be combined to deter abuse.

An opioid analgesic submitted for abuse deterrent formulation (ADF) labeling must show conformance to one or more of these categories. The present disclosure relates to an abuse deterrent pill for oral administration, which provides immediate release of an active pharmaceutical substance and conforms to one or more of these categories. In one embodiment, the abuse deterrent formulation of the present disclosure conforms to at least one of the six FDA categories. In another embodiment, the abuse deterrent formulation of the present disclosure conforms to at least two of the six FDA categories. In another embodiment, the abuse deterrent formulation of the present disclosure conforms to at least three of the six FDA categories. In another embodiment, the abuse deterrent formulation of the present disclosure conforms to at least four of the six FDA categories. In another embodiment, the abuse deterrent formulation of the present disclosure conforms to at least five of the six FDA categories.

For example, an abuse deterrent pill of the present disclosure can reduce abuse by the incorporation of at least one physical barrier. The physical barrier is designed to prevent abuse based on chewing, pulverizing, cutting, grating or grinding. Preferably, the physical barrier prevents or reduces the effectiveness of these methods. As used herein, the phrase "abuse deterrent" means that the active substance cannot readily be separated from the formulation in a form suitable for abuse by such means as, for example, grinding. The abuse deterrent pill of the present disclosure cannot be easily ground, extracted from, or both. Abuse deterrent measures render it difficult to transform the pill into a powder or extract for non-oral administration, such as intranasal or intravenous.

In one embodiment, the present disclosure relates to a directly-formed, extruded, oral, immediate release, abuse deterrent pill. The pill includes an active substance susceptible to abuse, a matrix agent and a plasticizer. After extrusion, the extrudate is directly formed into the pill without further processing, such as the use of a cutting step.

As used herein, the term "active substance" or "active substance susceptible to abuse" means an opioid or opioid related compound subject to potential abuse. The active substance may include, without limitation, alfentanil, allylprodine, alphaprodine, amphetamine, anileridine, benzylmorphine, bezitramide, buprenorphine, butorphanol, clonitazene, codeine, cyclazocine, desomorphine, dextroamphetamine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, and tramadol, and pharmaceutically acceptable salts and mixtures thereof. Preferably, the active substance is either oxycodone or hydrocodone. In one embodiment, the formulation of the present disclosure excludes oxymorphone. For example, the formulation of the present disclosure contains at least one active substance susceptible to abuse, provided the active substance is not oxymorphone.

The amount of active substance in the formulation may vary depending on the active substance, stability, release profile and bioavailability. The amount of active substance in the formulation may range from about 0.50 Wt % to about 15 Wt %. Particularly, the amount of active substance in the formulation may range from about 0.75 Wt % to about 14 Wt %, or from about 1.0 Wt % to about 13 Wt %, or from about 2.0 Wt % to about 12 Wt %, or from about 3.0 Wt % to about 11 Wt %, or from about 5.0 Wt % to about 10 Wt %. For example, the formulation may be a 100 mg pill having about 5 mg or about 10 mg of active substance (e.g., oxycodone HCl or hydrocodone bitartrate).

In another embodiment, the amount of active substance in the formulation may range from about 0.50 Wt % to about 40 Wt %. Particularly, the amount of active substance in the formulation may range from about 0.75 Wt % to about 37.5 Wt %, or from about 1.0 Wt % to about 35 Wt %, or from about 2.0 Wt % to about 34 Wt %, or from about 3.0 Wt % to about 32.5 Wt %, or from about 5.0 Wt % to about 30 Wt %. For example, the formulation may be a 100 mg pill having about 5 mg or about 30 mg of active substance (e.g., oxycodone HCl or hydrocodone bitartrate).

Formulations of the present disclosure may also include an additional active ingredient. Additional active ingredients include other analgesics, such as acetaminophen, ibuprofen, acetylsalicylic acid and/or naproxen. For example, the formulation may include an oxycodone HCl/acetaminophen combination, or a hydrocodone bitartrate/acetaminophen combination.

In one embodiment, the formulation includes at least one active substance, e.g. hydrocodone bitartrate, and at least one additional ingredient, e.g. acetaminophen. The amount of the at least one active substance and the additional ingredient in the formulation may vary depending on the active substance or the additional ingredient, their stability, their release profile and their bioavailability. In addition to the ranges provided above for the amount of active substance in the formulation, the amount of active substance in the formulation may also range from about 0.10 Wt % to about 10.0 Wt %. Particularly, the amount of active substance in the formulation may range from about 0.20 Wt % to about 8.0 Wt %, or from about 0.3 Wt % to about 6.0 Wt %, or from about 0.4 Wt % to about 4.0 Wt %, or from about 0.5 Wt % to about 2.0 Wt %. The amount of additional ingredient in the formulation may range from about 15 Wt % to about 80 Wt %. Particularly, the amount of additional substance in the formulation may range from about 20 Wt % to about 75 Wt %, or from about 25 Wt % to about 70 Wt %, or from about 30 Wt % to about 65 Wt %. For example, the formulation may be a 500 mg or 1,000 mg pill having about 5 mg or about 10 mg of active substance (e.g., oxycodone HCl or hydrocodone bitartrate) and about 300 mg or about 325 mg of additional analgesic (e.g. acetaminophen).

The dosage form of the present disclosure can be rendered abuse deterrent by incorporating at least one matrix agent in the formulation to increase the strength of the tablet beyond that of conventional dosage forms. The matrix agent increases the dosage form's resistance to physical or mechanical forces, such as pulverizing or grinding. By selecting the appropriate molecular weight grade and the quantity present within a formulation, the strength characteristics of the dosage form can be manipulated in a way to create a wide array of abuse deterrent pills have immediate release profiles.

The matrix agent may also render the dosage form abuse deterrent by acting as a gelling or viscosity increasing agent. Upon contact with a solvent (e.g., aqueous or semi-aqueous solution), the dosage form is capable of absorbing the solvent and swelling to form a viscous or semi-viscous substance. The formation of a viscous or semi-viscous substance significantly reduces and/or minimizes the amount of free solvent which can contain an amount of active substance, and which can be drawn into a syringe. The matrix agent can also reduce the overall amount of active substance extractable with the solvent by entrapping the active substance in a gel matrix. Typical matrix agents include pharmaceutically acceptable polymers, typically hydrophilic polymers, such as those that form hydrogels. These properties allow for an oral drug delivery system that satisfies at least one of the categories in the FDA guidance (e.g., "physical and chemical barriers can change the physical form of an oral drug rendering it less amenable to abuse").

The matrix agent may exhibit a high degree of viscosity upon contact with a suitable solvent. The high viscosity can enhance the formation of highly viscous gels when attempts are made to crush and dissolve the contents of a formulation in an aqueous or semi-aqueous vehicle and inject it intravenously. For example, when an abuser crushes and dissolves the formulation in a solvent, a viscous or semi-viscous gel is formed. The increase in the viscosity of the solution discourages the abuser from injecting the gel intravenously or intramuscularly by preventing the abuser from transferring sufficient amounts of the solution to a syringe.

Suitable matrix agents are natural or synthetic polymers capable of providing increased resistance to pulverizing or grinding. The matrix agent may be selected from the group consisting of agar, alamic acid, alginic acid, carmellose, carboxymethylcellulose sodium, chitosan, copovidone, dextrin, gelatin, hydroxyethyl cellulose, hydroxypropyl cellulose, hypromellose (HPMC), methylcellulose derivatives, microcrystalline cellulose, polyacrylic acid, polyalkalene oxide (e.g., polymethylene oxide, polyethylene oxide and polypropylene oxide), polyvinyl acetate, polyvinyl alcohol, povidone, propylene glycol alginate, polyvinylcaprolactam—polyvinyl acetate—polyethylene glycol graft copolymer, pullulan, silicon dioxide, sodium alginate, starch, and vinylpyrrolidone-vinyl acetate copolymers. In one embodiment, the matrix agent is a polyethylene oxide. Polyethylene oxide is a non-ionic, water soluble polymer that is readily available in a wide range of molecular weight grades.

The matrix agent should be capable of both ensuring the formation of a solid dosage form by extrusion and allowing immediate release of the active substance. The formulation of the present disclosure may accomplish both capabilities by using a matrix agent having an appropriate molecular weight (or appropriate average molecular weight), such as between about 50K Daltons and about 300K Daltons.

In one embodiment, the matrix agent has a molecular weight between about 100K and about 300K Daltons. Particularly, the matrix agent has a molecular weight between about 150K and about 250K Daltons, or about 180K and about 220K Daltons, or about 190K and about 210K Daltons, or about 195K and about 205K Daltons.

In another embodiment, the matrix agent has a molecular weight between about 100K and about 200K Daltons. Particularly, the matrix agent has a molecular weight between about 120K and about 180K Daltons, or about 130K and about 170K Daltons, or about 140K and about 160K Daltons, or about 145K and about 155K Daltons.

In another embodiment, the matrix agent has a molecular weight between about 50K and about 150K Daltons. Particularly, the matrix agent has a molecular weight between about 80K and about 120K Daltons, or about 85K and about 115K Daltons, or about 90K and about 110K Daltons, or about 95K and about 105K Daltons.

In another embodiment, the matrix agent has a molecular weight between about 50K and about 100K Daltons. Particularly, the matrix agent has a molecular weight between about 55K and about 95K Daltons, or about 60K and about 90K Daltons, or about 65K and about 85K Daltons, or about 70K and about 80K Daltons.

The performance of the matrix agent and the formulation is also dependent on the amount of matrix agent present in the formulation. The formulation, or final dosage form, may contain about 10 Wt % to about 90 Wt % matrix agent.

In one embodiment, the formulation contains between about 40 Wt % and 60 Wt % matrix agent. Particularly, the formulation contains between about 45 Wt % and about 55 Wt % matrix agent, or about 48 Wt % and about 52 Wt % matrix agent.

In another embodiment, the formulation contains between about 35 Wt % and 55 Wt % matrix agent. Particularly, the formulation contains between about 40 Wt % and about 50 Wt % matrix agent, or about 43 Wt % and about 47 Wt % matrix agent.

In another embodiment, the formulation contains between about 30 Wt % and 50 Wt % matrix agent. Particularly, the formulation contains between about 35 Wt % and about 45 Wt % matrix agent, or about 38 Wt % and about 42 Wt % matrix agent.

In another embodiment, the formulation contains between about 25 Wt % and 45 Wt % matrix agent. Particularly, the formulation contains between about 30 Wt % and about 40 Wt % matrix agent, or about 33 Wt % and about 37 Wt % matrix agent.

In another embodiment, the formulation contains between about 20 Wt % and 40 Wt % matrix agent. Particularly, the formulation contains between about 25 Wt % and about 35 Wt % matrix agent, or about 28 Wt % and about 32 Wt % matrix agent.

In another embodiment, the formulation contains between about 15 Wt % and 35 Wt % matrix agent. Particularly, the formulation contains between about 20 Wt % and about 30 Wt % matrix agent, or about 23 Wt % and about 27 Wt % matrix agent.

The dosage form of the present disclosure can also be rendered abuse deterrent by incorporating at least one plasticizer in the formulation. The plasticizer may provide the dosage form with a waxiness upon exposure to physical or mechanical forces, such as pulverizing or grinding. Suitable plasticizers may be selected from the group consisting of polyalkalene glycols (e.g., polyethylene glycol and polyethylene glycol monomethyl ether), acetyltributyl citrate, acetyltriethyl citrate, castor oil, diacetylated monoglycerides, dibutyl sebacate, diethyl phthalate, glycerin, propylene glycol, pullulan, sorbitol sorbitan solution, triacetin, tributyl citrate and triethyl citrate. In one embodiment, the plasticizer is polyethylene glycol.

The performance of the plasticizer is dependent on the size and the amount of plasticizer present in the formulation. In one embodiment, the plasticizer cannot be filtered and/or separated from a resulting solution of water and/or alcohol. The formulation of the present disclosure may include a plasticizer having a molecular weight between about 1K Daltons and about 15K Daltons. Particularly, the molecular weight is between about 2K Daltons and about 14K, about 3K and about 13K Daltons, about 5K and about 10K Daltons, or about 7K and about 9K Daltons.

The formulation, or final dosage form, may contain between about 5.0 Wt % and about 60 Wt % plasticizer. In one embodiment, the formulation contains between about 20 Wt % and about 60 Wt % plasticizer. Particularly, the formulation contains between about 30 Wt % and about 50 Wt % plasticizer, or about 35 Wt % and about 45 Wt % plasticizer. In another embodiment, the formulation contains between about 15 Wt % and about 30 Wt % plasticizer. Particularly, the formulation contains between about 20 Wt % and about 28 Wt % plasticizer, or about 23 Wt % and about 27 Wt % plasticizer. In another embodiment, the formulation contains between about 5.0 Wt % and about 20 Wt % plasticizer. Particularly, the formulation contains between about 8.0 Wt % and about 17 Wt % plasticizer, or about 10 Wt % and about 15 Wt % plasticizer.

The dosage form of the present disclosure may also contain a filler/binder excipient (herein "filler"). A filler may be added to provide or increase the consistency of the extrudate for processing into a final dosage form. The filler may also help with hardness and dissolution of the dosage form. The filler may be a known excipient for use in pharmaceutical formulations that, upon extrusion, is capable of producing an extrudate that holds its shape. In some embodiments, the filler may have a melting temperature above the extrusion process temperatures, such as a melting temperature above about 80° C., 90° C., 100° C., 110° C., 120° C., or 130° C. The filler may also be a material that exhibits excellent flow and compression properties, wherein such flow and compression properties are measured by traditional methods known to persons skilled in the art of pharmaceutical formulations.

The filler may be selected from the group consisting of microcrystalline cellulose, silicified microcrystalline cellulose, powdered cellulose, maize starch, modified maize starch, potato starch, lactose monohydrate, lactose anhydrous, mannitol, dibasic calcium phosphate dihydrate, anhydrous dibasic calcium phosphate, magnesium carbonate, erythritol, trehalose and mixtures thereof. In one embodiment, the filler is microcrystalline cellulose and/or lactose monohydrate.

In some embodiments, the filler may also be useful as a disintegrant. For example, the inclusion of 10% or more of a filler, e.g., microcrystalline cellulose, also acts as a disintegrant.

The performance of the filler and the formulation is also dependent on the amount of filler present in the formulation. The formulation, or final dosage form, may contain between about 0 Wt % and about 40 Wt % filler. In one embodiment, the formulation contains between about 10 Wt % and about 40 Wt % filler. Particularly, the formulation contains between about 20 Wt % and about 40 Wt % filler, about 30 Wt % and about 40 Wt % filler, about 32 Wt % and about 38 Wt % filler, or about 34 Wt % and about 36 Wt % filler. In another embodiment, the formulation contains between about 25 Wt % and about 35 Wt % filler. Particularly, the formulation contains between about 27 Wt % and about 33 Wt % filler, or about 29 Wt % and about 31 Wt % filler. In another embodiment, the formulation contains between about 20 Wt % and about 30 Wt % filler. Particularly, the formulation contains between about 22 Wt % and about 28 Wt % filler, or about 24 Wt % and about 26 Wt % filler. In another embodiment, the formulation contains between about 10 Wt % and about 20 Wt % filler. Particularly, the formulation contains between about 12 Wt % and about 18 Wt % filler, or about 14 Wt % and about 16 Wt % filler. In another embodiment, the formulation of the present disclosure excludes a filler.

In one embodiment, the formulation includes a disintegrant. A disintegrant promotes disintegration of the pill, and dissolution of the active substance, after administration and upon contact with water. The disintegrant may be selected from sodium starch glycolate, cross-linked polyvinylpyrrolidone, sodium bicarbonate/citric acid, alginic acid or combinations thereof. The formulation, or final dosage form, may contain between about 1.0 Wt % and about 20 Wt % of disintegrant. Particularly, the formulation contains between about 1.0 Wt % and about 10 Wt % disintegrant. In another embodiment, the formulation of the present disclosure excludes a disintegrant.

In another embodiment, the formulation includes a dye. A dye is useful to distinguish or identify the pill of the present disclosure from other drug products. The dye may be selected from known dyes suitable for use in pharmaceutical formulations or approved by the FDA for such use. For example, the dye may be FD&C Blue No. 2 or a 50/50 Wt % blend of FD&C Blue No. 2 in polyethylene glycol. In one embodiment, the dye and polyethylene glycol blend cannot be substantially filtered and/or separated from a resulting solution of water and/or alcohol. The formulation, or final dosage form, may contain between about 0.10 Wt % and about 15 Wt % dye. Particularly, the formulation may contain between about 0.20 Wt % and about 12.5 Wt % dye, or about 0.50 Wt % and about 10 Wt % dye. In some embodiments, the formulation contains at least 0.1%, 0.2%, 0.3%, 0.5%, 0.8%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, and 20% dye. These values can also be used to define a range of dye present in the formulations, e.g., about 3.0% to about 5.0%. In another embodiment, the formulation of the present disclosure excludes a dye.

In another embodiment, the formulation includes a preservative or antioxidant. The preservative or antioxidant reduces or limits the degradation or deterioration of the abuse deterrent dosage form. For example, the components of the oral drug delivery system (e.g., active substances, matrix agents) may undergo degradation (e.g., oxidative reduction, chain cleavage) due to oxidation. Preventing degradation is essential to maintaining a proper release profile. For instance, the molecular weight of polyethylene oxide in the formulation affects the release profile of the active substance. The addition of a preservative or antioxidant in the formulation that reduces or eliminates the degradation of the molecular weight of polyethylene oxide is useful to maintain the release profile of the active substance.

The preservative or antioxidant may be selected from preservatives or antioxidants known to one skilled in the art for use in pharmaceutical formulations, such as citric acid, ascorbic acid, ascorbyl palmitate, butylated hydroxyanisole (BHA), butylated hydroxytoluene (BHT), erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide and tocopherols. The formulation, or final dosage form, may contain between about 0.1 Wt % and about 2.0 Wt %, or about 0.25 Wt % and about 0.75 Wt % of preservative or antioxidant. In another embodiment, the formulation of the present disclosure excludes a preservative or antioxidant.

In some embodiments, the dosage form includes one or more agents that decrease the purity of the active substance in an alcohol solution or extraction product. The alcohol purity decreasing agent can reduce or limit the potential for abuse by decreasing the total weight percent of active substance found in the alcohol solution or alcohol based extraction by increasing the amount of other substances also found in the solution or extraction. For example, a common form of abuse involves extraction of active substance using ethanol, or ethanol solutions (e.g., 1%-99% ethanol), resulting in a very pure powder. When introduced to an alcohol solution, components of the oral drug delivery system containing an alcohol purity decreasing agent (e.g., active substances, excipients) may become dissolved in the solution, creating a homogenous liquid which prevents extraction and subsequent alcohol evaporation to a very pure active substance. In one embodiment, the alcohol purity decreasing agent substantially decreases the purity of a resulting alcohol and/or water solution or powder. In another embodiment, the alcohol purity decreasing agent is not soluble in water. The dosage form may contain between about 0.1 wt % to 40 wt % alcohol purity decreasing agent. In some embodiments, the formulation contains at least 0.1%, 0.25%, 0.5%, 1.0%, 2.0%, 3.0%, 4.0%, 5.0%, 6.0%, 7.0%, 8.0%, 9.0%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% alcohol purity decreasing agent. These values can also be used to define a range of agent present in the formulations, e.g., about 5.0% to about 15.0%. In another embodiment, the dosage form of the present disclosure excludes an alcohol purity decreasing agent.

The alcohol purity decreasing agent may be selected from excipients known to one skilled in the art for use in pharmaceutical formulations, such as alginic acid, calcium acetate, carbomers, carboxymethylcellulose, ethylcellulose, gelatin, hydroxyethylcellulose, hydroxypropyl cellulose, methylcellulose, poloxamers, polyvinyl alcohol, polyvinyl acetate, polyvinylpyrrolidone, and sodium alginate. In a specific embodiment, the agent is calcium acetate.

In some embodiments, the alcohol purity decreasing agent reducing the purity of a resulting alcohol and/or water solution or powder by at least 10%, 11%, 12%, 13%, 14%, 15%, 16%, 17%, 18%, 19%, 20%, 25%, 30%, 35%, 40%, 45%, 50%, 60%, 70%, 80%, 90% or 95%. These values can also be used to define a range of purity reduction, e.g., about 10% to about 30%.

The formulation may additionally include at least one additive independently selected from surfactants, bulking agents, lubricants, flavorings or combination thereof.

The abuse deterrent pill of the present disclosure is capable of immediate release of the active substance. The dosage form may be manufactured to provide a composition exhibiting an immediate release profile of at least one active substance. As used herein, "immediate release" refers to a dosage form that releases the active substance or a pharmaceutically acceptable salt thereof, substantially completely into the gastrointestinal tract of the user within a period of less than an hour, and often less than about 45 minutes from ingestion. In one embodiment, the amount of active substance released from the dosage form, e.g. oxycodone HCl, by exposure to a deairated water within 45 minutes is greater than or equal to 75%. In another embodiment, the amount of active substance released from the dosage form, e.g. hydrocodone bitartrate/acetaminophen, by exposure to a 0.1 N hydrochloric acid solution within 30 minutes is great than or equal to 90%.

In one embodiment, the formulation of the present disclosure releases greater than or equal to about 75% of the active substance within 45 minutes after administration or via dissolution testing. Particularly, the formulation releases greater than or equal to about 80%, about 85%, about 90%, or about 95% of the active substance within 45 minutes after administration or via dissolution testing.

In other embodiments, the formulation of the present disclosure releases greater than or equal to about 90% of the active substance within 30 minutes after administration or via dissolution testing. Particularly, the formulation releases greater than or equal to about 92%, about 94%, about 96%, or about 98% of the active substance within 30 minutes after administration or via dissolution testing.

The formulation of the present disclosure is abuse deterrent and does not rapidly release the active substance within a relatively short time after administration or dissolution testing begins. In some embodiments, the formulation of the present disclosure releases less than about 95% of the active substance within 20 minutes after administration or via dissolution testing. Particularly, the formulation releases less than about 90% of the active substance, less than about 85%, less than about 80%, less than about 75%, less than about 70%, less than about 65%, or less than about 60% within 20 minutes after administration or via dissolution testing.

In other embodiments, the formulation of the present disclosure releases less than about 95% of the active substance within 15 minutes after administration or via dissolution testing. Particularly, the formulation releases less than about 90% of the active substance, less than about 85%, less than about 80%, less than about 75%, less than about 70%, less than about 65%, or less than about 60% within 15 minutes after administration or via dissolution testing.

In one embodiment, the present disclosure relates to an oral, immediate release, abuse deterrent dosage form comprising an active substance susceptible to abuse, wherein less than about 95% of the active substance is released from the dosage form within 20 minutes following administration, and wherein greater than or equal to 75% of the active substance is released from the dosage form within 45 minutes following administration. In another embodiment, the present disclosure relates to an oral, immediate release, abuse deterrent dosage form comprising an active substance susceptible to abuse, wherein less than about 95% of the active substance is released from the dosage form within 15 minutes following administration, and wherein greater than or equal to 90% of the active substance is released from the dosage form within 30 minutes following administration.

The formulation, or abuse deterrent pill, may also include at least one physical barrier to reduce abuse. The physical barrier may be the inability of the pill to be abused by pulverizing and swallowing, pulverizing and snorting, pulverizing and injecting, or combinations thereof. For example, the abuse deterrent pill of the present disclosure may be incapable of being significantly pulverizing by physical or mechanical force.

One of the most common means of abuse of an orally administered opioid analgesic involves the manipulation of the oral dosage form in order to cause rapid delivery to the bloodstream via nasal insufflation. In order for insufflation to be used as an effective means of abuse, the original dosage form must be manipulated so as to decrease the particle size of the ingested drug to about 0.5 mm or less. A particle size of about 0.5 mm or less is necessary for effective intranasal absorption to occur. By limiting the quantity of particles under about 0.5 mm that an abuser can obtain by reasonable methods, one can render insufflation ineffective as a means of abuse. One way this physical barrier may be created is by capturing the active substance susceptible to abuse in a plastic matrix which is resistant to being physically broken down to produce particles smaller than about 0.5 mm.

The dosage form of the present disclosure can inhibit manipulation by grinding or pulverizing using common equipment, such as a coffee grinder. For example, the formulation deters abuse by limiting the particle size to which the formulation may be ground. The formulation prevents the pill, or at least substantial portions of the pill, from being ground in particles having a particle size of about 0.5 mm or less that may pass through the membrane of the nasal cavity. The dosage form can also significantly limit the extraction of the active substance by common solvents (e.g., cold water or distilled aqueous ethanol) from the formulation. For example, the formulation deters abuse by limiting the ability of persons to extract the active substance from the formulation (either intentionally or unintentionally), such that the active substance cannot easily be concentrated for parenteral administration. The abuse deterrent formulation may also include, but does not require, the incorporation of other deterrents such as antagonists or irritants.

In one embodiment, the abuse deterrent pill of the present disclosure may be incapable of being crushed by grinding into a form that may be abused. In a coffee grinder assay as described in Example 1 (e.g., grinding in a coffee grinder at about 20,000+ rpm and for about 30-60 seconds) the pill remains in a form that may not be abused. The coffee grinder assay may be performed using a commercial coffee grinder, or equivalent, capable of grinding abuse deterrent pills. The pills tested using the coffee grinder assay have a substantial portion of the resulting particles with a particle size which is not able to be abused, i.e. intranasal administered. Abuse deterrent pills having a substantial amount of such particles reduce the incentive or cost-effectiveness of persons to abuse the formulations. For example, a potential abuser who can only access for intranasal administration less than about 50% of the active substance will be deterred from abusing the formulation.

Upon exposure to a grinding force (e.g., the coffee grinder assay or equivalent), the abuse deterrent pill may be grinded into particles wherein at least about 50 Wt % of the grinded particles have a particle size greater than about 0.5 mm. Particularly, upon exposure to a grinding force, the abuse deterrent pill may be grinded into particles wherein at least about 55 Wt % of the grinded particles, 60 Wt % of the grinded particles, 65 Wt % of the grinded particles, 70 Wt % of the grinded particles, 75 Wt % of the grinded particles, 80 Wt % of the grinded particles, 85 Wt % of the grinded particles, 90 Wt % of the grinded particles, or 95 Wt % of the grinded particles have a particle size greater than about 0.5 mm.

In another embodiment, the abuse deterrent pill of the present disclosure may be capable of forming a hydrogel upon exposure to an aqueous or semi-aqueous solution. The formation of the hydrogel deters abuse by limiting the ability of persons to extract the active substance from the formulation, such that the active substance cannot easily be concentrated for parenteral administration.

In some embodiments, the abuse deterrent pill of the present disclosure is capable of releasing its dye upon introduction to an aqueous or semi-aqueous solution. The dye provides a visual deterrent to abuse via parenteral administration by giving the solution a turbid and/or deep color. In some embodiments, the dye is not capable of being separated from the solution via nylon, PTFE, coffee or other readily available filters or filtering techniques.

In another embodiment, the present disclosure relates to a process for the production of an oral, immediate release, abuse deterrent pill containing at least one active substance susceptible to abuse comprising processing a uniform blend of the at least one active substance susceptible to abuse, a matrix agent and a plasticizer by hot melt extrusion to produce an extrudate. The extrudate may therein be formed using a forming unit into the pill.

Hot melt extrusion is a processing technique used to make the formulations and compositions of the present disclosure because it allows for the creation of homogeneous polymer matrices with specific abuse deterrent properties. For example, by varying the formulation and the processing parameters specific properties such as dissolution time, pulverization resistance, material processability, and stability can be selectively modified. Formulations that include polymer matrix agents (e.g., polyethylene oxide) can provide a unique advantage as they allow for formulations in which release characteristics can be controlled while also creating a physical barrier that prevents abuse (e.g., through means of nasal inhalation or intravenous injection). Furthermore, in a hot melt extrusion process, process analytic data can be provided in real time. The process may also be adapted for continuous process manufacturing procedure as opposed to traditional batch to batch processing.

The abuse deterrent pill of the present disclosure may be formed by hot melt extrusion using commercially available extruders, such as a twin screw extruder. Several factors of the extrusion process may affect the final extrudate including: screw design (sheer rating), screw speed, temperature profile, feed rate, dwell time, die pressure and die size. These factors may be varied to obtain an extrudate with desired processing capabilities such that the extrudate is uniform, holds its shape, and is capable of being formed into pills by a forming unit.

An exemplary extruder and forming unit system (10) is shown in FIG. 1. The extruder (14) includes a hopper or feeding unit (12) wherein a uniform blend of the formulation is made or transferred to. The uniform blend is fed into the inlet (16) of the extruder (14) by starve feeding via a gravimetric or volumetric dosing unit. The formulation of the present disclosure is preferably uniformly blended prior to introduction to the extrusion process. Insufficient blending of the components may produce a non-uniform extrudate and non-uniform abuse deterrent pills having inconsistent amounts of active substance. Over-blending may produce a poorly performing formulation. The blending process may be monitored using a process analytical technique to determine when a uniform blend is achieved. In one embodiment, the mixing bin or hopper (12) may be equipped with a near-infrared (NIR) monitoring system for in-line, continuous monitoring of the blend.

In one embodiment, monitoring of the blending process by NIR involves preparing a NIR standard spectrum for each formulation. The NIR standard spectra may be prepared empirically by monitoring the blending of different batches of the formulation. The blending conditions and/or extrusion process may be correlated with NIR spectra to determine a NIR standard spectrum for a given dosage form. Once the optimum NIR monitoring spectrum and conditions are determined, the formulation is blended until the NIR standard is achieved. One of ordinary skill in the art armed with the present disclosure can implement a near-infrared monitoring system for in-line, continuous monitoring of the blend.

The extruder (14) then processes the blend into a melt and passes the extrudate (50) out of the extruder (14) through a die section (30) and through a die outlet (18). The extruder (14) may have temperature zones (20-30) and pressure zone (40-43). These zones may include components to heat and pressurize the extruder (14) or may include sensors to measure the temperature and/or pressure of each particular zone.

As used herein the term melt temperature refers to the temperature at which an excipient changes from solid to liquid state. As used herein the term softening temperature refers to the temperature at which an excipient changes from solid form into a malleable, dynamic solid.

The temperature profile of the extruder (14) is important to obtain a uniform extrudate (50) with little to no degradation products. Heat may be applied to soften, and in some embodiments to melt, the excipients (e.g., matrix agent, plasticizer) to form a homogenous matrix to encapsulate the active substance. The extruder temperature profile, or the temperatures in the extruder zones (20-30), is preferably kept below the melting point, and often the degradation point, of the active substance.

For example, the melting temperature of polyethylene oxide is about 67° C. and of polyethylene glycol is about 63° C. Common active substances begin to melt at temperatures much higher than this. For example, the melt temperature of oxycodone HCl is about 219° C. and of hydrocodone bitartrate is about 147° C. Preferably, the temperature of one or more of the zones (20-30) is kept at or below the melting point of the active pharmaceutical ingredients. In particular, the temperature of one or more of the zones (20-30) is kept below about 120° C., 110° C., 100° C., 90° C., 80° C., 75° C., 70° C., 65° C., or 60° C.

In one embodiment, the temperature of at least one of the extruder zones (20-30) is kept at or below the melting point of the active pharmaceutical ingredients. Particularly, the temperature of at least one of the zones is kept below about 120° C., about 110° C., about 100° C., about 90° C., about 80° C., about 75° C., about 70° C., about 65° C., or about 60° C.

In another embodiment, the temperature of at least two of the extruder zones (20-30) is kept at or below the melting point of the active pharmaceutical ingredients. Particularly, the temperature of at least two of the zones is kept below about 120° C., about 110° C., about 100° C., about 90° C., about 80° C., about 75° C., about 70° C., about 65° C., or about 60° C.

In another embodiment, the temperature of at least three of the extruder zones (20-30) is kept at or below the melting point of the active pharmaceutical ingredients. Particularly, the temperature of at least three of the zones is kept below about 120° C., about 110° C., about 100° C., about 90° C., about 80° C., about 75° C., about 70° C., about 65° C., or about 60° C.

In another embodiment, the temperature of at least four of the extruder zones (20-30) is kept at or below the melting point of the active pharmaceutical ingredients. Particularly, the temperature of at least four of the zones is kept below about 120° C., about 110° C., about 100° C., about 90° C., about 80° C., about 75° C., about 70° C., about 65° C., or about 60° C.

In another embodiment, the temperature of at least five of the extruder zones (20-30) is kept at or below the melting point of the active pharmaceutical ingredients. Particularly, the temperature of at least five of the zones is kept below about 120° C., about 110° C., about 100° C., about 90° C., about 80° C., about 75° C., about 70° C., about 65° C., or about 60° C.

In another embodiment, the temperature of at least six of the extruder zones (20-30) is kept at or below the melting point of the active pharmaceutical ingredients. Particularly, the temperature of at least six of the zones is kept below about 120° C., about 110° C., about 100° C., about 90° C., about 80° C., about 75° C., about 70° C., about 65° C., or about 60° C.

In another embodiment, the temperature of all of the extruder zones (20-30) is kept at or below the melting point of the active pharmaceutical ingredients, with the optional exception of the die zone. Particularly, the temperature of all of the zones is kept below about 120° C., about 110° C., about 100° C., about 90° C., about 80° C., about 75° C., about 70° C., about 65° C., or about 60° C., with the optional exception of the die zone.

The temperature of the die (18, 30) may be maintained at a slightly higher temperature than the temperature of one or more of the other zones. In some embodiments, the die temperature (18, 30) is held at or slightly above the melting point of the extrudate, or the matrix and plasticizer, to ensure a uniform extrudate (50) exiting the die outlet (18).

The extruder (14) also has a pressure profile. Pressure is important to melt the excipients to make mixing more efficient and to force the extrudate (50) through the die outlet (18) to exit the extruder (14) in a consistent manner. Particularly, the pressures in the zones and also the pressure at the die outlet (18), is kept at or above about 5 bar, about 10 bar, about 15 bar, about 20 bar, about 30 bar, about 40 bar, about 50 bar, about 60 bar, about 70 bar, about 80 bar, about 90 bar, about 100 bar or about 110 bar.

In one embodiment, the pressure of one or more of the pressure zones (40-43) in the extruder (14) is kept at a high enough pressure to achieve melting, compression, and mixing of the matrix and plasticizing agents with non-melting excipients (e.g., API, filler, disintegrants, and antioxidant) while the temperature of one or more of the temperature zones (20-30) is at or slightly below the melting point at standard pressure of these agents. The increased pressure allows for more efficient mixing due to compaction and shearing forces without having to dramatically increase temperature. These lower temperatures reduce, or substantially eliminate, the formation of degradation products from the active substances. In one embodiment, the pressure produced on the die (43) of the extruder (14) is kept sufficiently high enough to reduce pulsating flow and ensure a uniform extrudate (50) is delivered though the die outlet (18). A sufficiently high pressure assists in compacting the homogenous melt into a processable strand of desired diameter.

In one embodiment, the pressure of at least one of the pressure zones (40-43) is kept at a high enough pressure to achieve melting, compression, and mixing of the matrix and plasticizing agents with the active substance and any non-melting excipients. Particularly, the pressure of at least one of the zones is kept at or above about 5 bar, about 10 bar, about 15 bar, about 20 bar, about 30 bar, about 40 bar, about 50 bar, about 60 bar, about 70 bar, about 80 bar, about 90 bar, about 100 bar or about 110 bar In another embodiment, the pressure of at least two of the pressure zones (40-43) is kept at a high enough pressure to achieve melting, compression, and mixing of the matrix and plasticizing agents with the active substance and any non-melting excipients. Particularly, the pressure of at least two of the zones is kept at or above about 5 bar, about 10 bar, about 15 bar, about 20 bar, about 30 bar, about 40 bar, about 50 bar, about 60 bar, about 70 bar, about 80 bar, about 90 bar, about 100 bar or about 110 bar In another embodiment, the pressure of at least three of the pressure zones (40-43) is kept at a high enough pressure to achieve melting, compression, and mixing of the matrix and plasticizing agents with the active substance and any non-melting excipients. Particularly, the pressure of at least three of the zones is kept at or above about 5 bar, about 10 bar, about 15 bar, about 20 bar, about 30 bar, about 40 bar, about 50 bar, about 60 bar, about 70 bar, about 80 bar, about 90 bar, about 100 bar or about 110 bar In another embodiment, the pressure of all of the pressure zones (40-43) is kept at a high enough pressure to achieve melting, compression, and mixing of the matrix and plasticizing agents with the active substance and any non-melting excipients. Particularly, the pressure of all of the zones is kept at or above about 5 bar, about 10 bar, about 15 bar, about 20 bar, about 30 bar, about 40 bar, about 50 bar, about 60 bar, about 70 bar, about 80 bar, about 90 bar, about 100 bar or about 110 bar The melt extrudate may be optionally analyzed within the extruder (14) using near-infrared technology. NIR spectroscopy can be used as a non-invasive alternative to high performance liquid chromatography techniques. A NIR probe (80) may be included within the extruder (14). The wavelengths and intensities at which raw organic materials of the melt extrudate absorb light energy can be plotted to produce spectra to compare against a standard. With the spectrum of the API known, it can be used to determine and monitor the % wt of the active pharmaceutical ingredient present in the extrudate in real time.

The extrudate from an extruder is directly formed into a pill using a forming unit, provided that the size or shape of the extrudate may be adjusted prior to introduction to the forming unit (e.g., via a rope sizer). In some embodiments, the extrudate is directly formed into a dosage form without a further processing step, such as a cutting or milling step. The forming unit may be a unit capable of forming the pill without cutting or milling the extrudate. The forming unit may be a calendar, rotary, or a chain forming machine. As shown in FIG. 1, the extrudate (50) may be shaped into the abuse deterrent form (70) by a forming unit (60). In one embodiment, the extrudate (50) is shaped into the abuse deterrent form (70) by a calendaring process.

The forming unit (60) may comprise two rotating components each having molds (62) inset in the rotating components and aligned such that the molds (62) overlap with each other as the rotating components interface. When the extrudate (50) is guided between the rotating components of the forming unit (60), the offset and aligned molds (62) (or cavities) accept the extrudate and form the extrudate into the dosage form as provided by the shape of the molds (62), provided a sufficient amount of extrudate is guided between and supplied to the rotating components.

Figure 2:
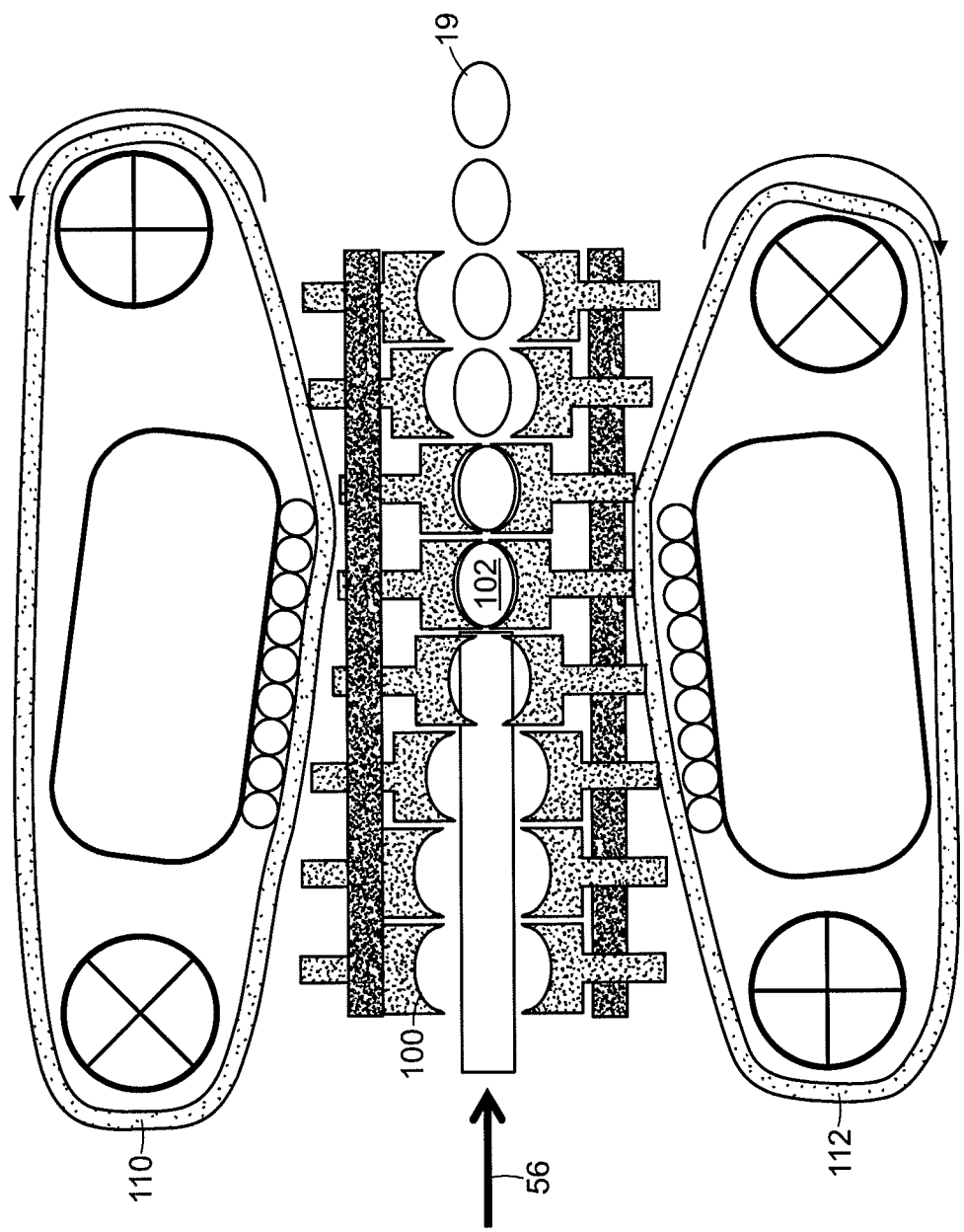
FIG. 2 shows an embodiment of a chain forming unit. The chain forming unit includes an upper and lower chain system (110 and 112) and tooling (100) to form the incoming extrudate (56) into formed pills (19).

In another embodiment, the forming unit may also comprise of a rotating set of punch dies with accompanying pinching ring, e.g. a chain die forming unit. FIG. 2 shows an embodiment of a chain forming unit. The chain forming unit includes an upper and lower chain system (110 and 112) and tooling (100) to form an incoming extrudate (56) into formed pills (19). When the extrudate (56) is fed into the chain die forming unit, the ring tooling (100) pinches the extrudate (56) to the exact weight of the finished pill and simultaneously presses it into a final form by the punches via a cam track. In one embodiment, the centripetal forces produced by the rotation of the machine aid in the ejection of the final pill form (19).

The extruder/forming unit system (10) may also be equipped with an additional component or transfer unit to assist the transfer of the extrudate (50) from the extruder (14) to the forming unit (60). The transfer unit may be capable of controlling the temperature, pressure, environment and/or shape of the extrudate. For example, the transfer unit may include heated/cooled sizing rollers which process the extrudate (50) into a consistent size (e.g., diameter) before entering the forming unit, cooling air jets, and extrudate diameter monitoring. The transfer unit may also be capable of guiding the extrudate into and between the rotating components of the forming unit (60).

Figure 3:
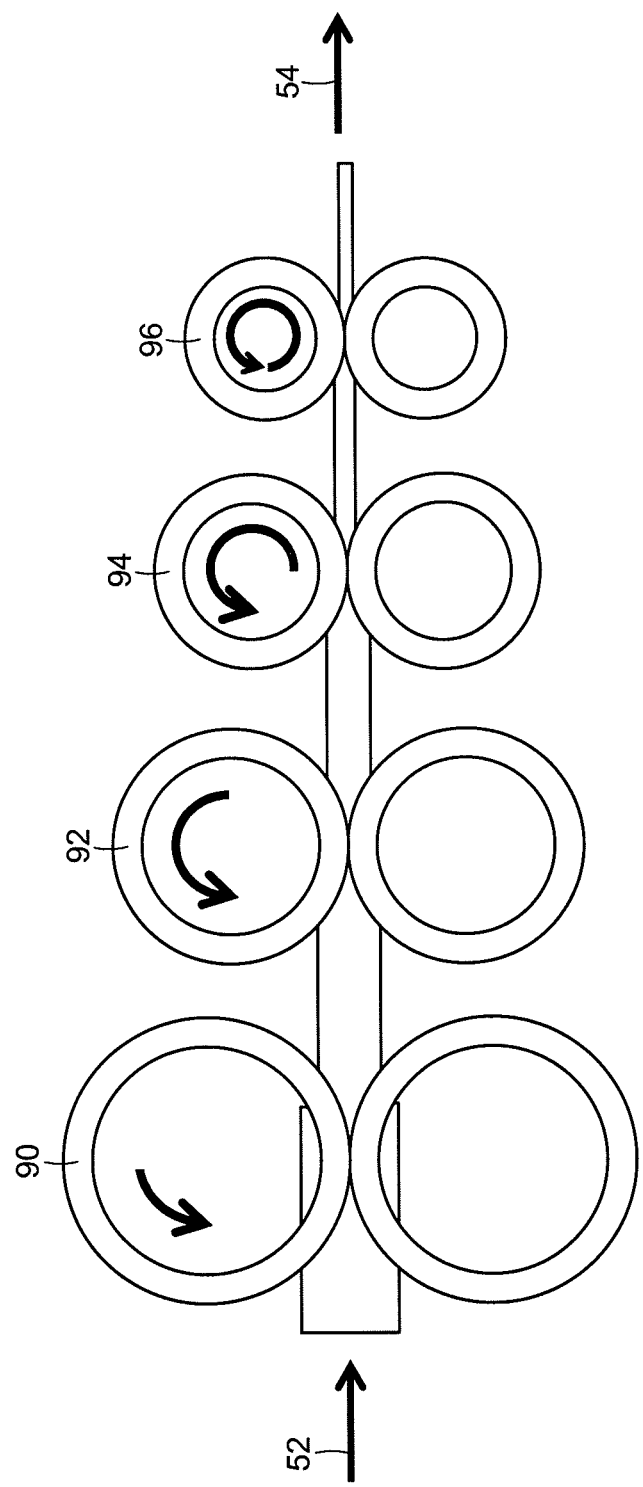
FIG. 3 shows an embodiment of an extrudate sizing apparatus (e.g., rope sizer). The rope sizer includes consecutive rollers (90-96) rotating at consecutively faster speeds for accepting an incoming extrudate (52) and expelling a faster moving, re-sized (smaller diameter) extrudate (54).

For example, the extrudate may be adjusted by an apparatus that re-sizes the extrudate, re-shapes the extrudate, or both. FIG. 3 shows an embodiment of an extrudate sizing apparatus (e.g., rope sizer). The rope sizer includes a number of consecutive rollers (90-96) to re-size or re-shape an incoming extrudate (52), either from the extruder (14) or from another step. The number, shape and orientation of the rollers (90-96) may vary depending on the degree of re-sizing and/or re-shaping desired. In some embodiments, the extrudate will be re-sized into a smaller diameter extrudate. In these embodiments, the rotating rollers will rotate at consecutively faster speeds. As such, the re-sized and/or re-shaped extrudate having a smaller diameter will be moving at a faster speed exiting the rope sizer.

The size and shape of the extrudate (50) may be designed to efficiently interact with different shaped molds (62). For example, an oval shaped extrudate may be formed to interact with a wide and shallow set of molds (62). Also, the speed and mass (or volume) of the extrudate (50) may be designed to efficiently interact with the size and speed of the forming unit. The speed and mass (or volume) of the extrudate (50) guided between the rotating components of the forming unit (60) should be sufficient to fill each set of molds completely with no voids.

The size and shape, and the speed and mass (or volume) of the extrudate (50) as well as size and shape of the molds (62) and the speed of the forming unit may be matched to reduce the amount of excess extrudate that is not formed into the dosage form (e.g., reduce waste). The two processes may be synchronized by attaching both to the same drive system.

Preferably, the forming unit is capable of forming abuse deterrent pills from the extrudate wherein more than about 90% of the extrudate is utilized (e.g., formed into the dosage form). More preferably, the forming unit utilizes more than about 95% of the extrudate. Even more preferably, the forming unit utilizes more than about 99% of the extrudate.

The molds (62) may optionally be formed with a non-uniform bottom or lower surface to allow for easy removal of the pill after formation. The molds (62) may also have markings in the bottom or lower surface to provide marking on the abuse deterrent pills upon formation.

After formation, the quality, volume and weight of each pill may be determined using an automated optical inspection technique. The optional inspection technique combines a weight determination step and a visual inspection step into a single step. For example, the visualization step may include taking multiple pictures of each pill. From these pictures, an estimated volume is determined. The estimated volume and the pre-determined density of the composition of the formulation may provide an estimated weight for each pill. Those pills that satisfy certain quality, volume and weight criteria will pass the optical inspection.

In another embodiment, the present disclosure relates to an process for the production of an oral, immediate release, abuse deterrent pill containing at least one active substance susceptible to abuse comprising combining the at least one active substance susceptible to abuse, a matrix agent, and a plasticizer in a hopper to form a mixture; blending the mixture in the hopper until a uniform blend is achieved; monitoring the mixture during blending using a process analytical technique to determine when a uniform blend is achieved; feeding the uniform blend into an extruder; processing the uniform blend by hot melt extrusion to produce an extrudate; optionally monitoring of the extrudate at the die head via PAT NIR probe; transferring the extrudate to a forming unit using a transfer line capable of controlling the temperature, pressure, environment, and/or shape of the extrudate; forming the extrudate using the forming unit into the pill; and determining the quality, volume and weight of the pill using an optical inspection technique.

In another embodiment, the present disclosure relates to a method of treating pain comprising administering to an individual in need thereof a therapeutically effective amount of a dosage form as described herein. The dosage form provides rapid onset of analgesia for the treatment of moderate to severe pain.

The disclosures of all cited references including publications, patents, and patent applications are expressly incorporated herein by reference in their entirety. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Abuse deterrent formulations were prepared containing acetaminophen. Acetaminophen was utilized as a tracer in place of oxycodone HCl due to its availability, cost, similar particle size, and solubility profile. Tables 1-3 show the exemplary ranges of components for the abuse deterrent formulations.

TABLE 1

Exemplary Abuse Deterrent Formulation Ranges

| Components | Wt % |
|---|---|
| Active Substance | 0.1-30.0 |
| Matrix Agent (50 K to 300 K Daltons) | 10.0-90.0 |
| Plasticizer (1 K to 15 K Daltons) | 5.0-60.0 |
| Filler | 0.0-40.0 |
| Disintegrant | 0.0-10.0 |
| Antioxidant(s) | 0.0-2.0 |
| Dye | 0.0-20.0 |
| Alcohol Purity Decreasing Agent | 0.0-30.0 |

TABLE 2

Exemplary Abuse Deterrent Formulation Ranges

| Components | Wt % |
|---|---|
| Active Substance | 0.1-15.0 |
| Polyethylene Oxide (50 K to 300 K Daltons) | 10.0-90.0 |
| Polyethylene Glycol (1 K to 15 K Daltons) | 5.0-60.0 |
| Microcrystalline Cellulose | 20.0-40.0 |
| Crospovidone (Disintegrant) | 0.0-10.0 |
| Citric Acid (Antioxidant 1) | 0.0-1.0 |
| Butylated hydroxytoluene (Antioxidant 2) | 0.0-1.0 |
| Calcium Acetate | 0.0-10.0 |

TABLE 3

Exemplary Abuse Deterrent Formulation Ranges

| Components | Wt % |
|---|---|
| Active Substance | 5.0-10.0 |
| Polyethylene Oxide (50 K to 300 K Daltons) | 30.0-50.0 |
| Polyethylene Glycol (1 K to 15 K Daltons) | 15.0-30.0 |
| Lactose Monohydrate | 5.0-15.0 |
| Disintegrant | 2.5-7.5 |
| Antioxidants | 0.5-1.5 |
| Dye | 0.5-1.5 |
| Alcohol Purity Decreasing Agent | 0.0-30.0 |

Immediate release abuse deterrent pills containing acetaminophen were manufactured according to the formulation provided in Table 1.

The formulation was blended prior to extrusion. Extrusion was performed by means of a twin screw extruder of type Coperion ZSK26. To achieve a uniform extrudate with good processing capabilities a medium sheer screw design was used at a relatively slow screw speed (120 RPM). The temperature profile was designed to immediately melt the matrix and plasticizer agents (e.g., the polyethylene oxide and polyethylene glycol). Thereafter, the temperature was adjusted to be at or slightly below the melting temperature of the extrudate at standard pressure to achieve mixing. Adequate mixing was achieved by maintaining high pressures in the extruder.

At times, the die was heated to a temperature above the general melting temperature of the extrudate. It was found that at die temperatures at the melting temperature of the extrudate, the portion of the extrudate in contact with the inside die surface sheared off due to friction. An increase in die temperature allowed the outside surface of the extrudate to melt and slide along the die producing a uniform extrudate. Operating temperatures and pressures are provided in Table 5. The temperature and pressure zones in Table 5 correspond to the zones shown in FIG. 1.

TABLE 4

Extrusion Temperature and Pressure

| | Temp | Pressure |
|---|---|---|
| Zone 1 | 63-67° C. | |
| Zone 2 | 58-62° C. | |
| Zone 3 | 58-62° C. | |
| Zone 4 | 57-61° C. | |
| Zone 5 | 57-61° C. | |
| Zone 6 | 57-61° C. | |
| Zone 7 | 57-61° C. | |
| Zone 8 | 57-61° C. | |
| Zone 9 | 57-61° C. | |
| Zone 10 | 57-61° C. | |
| Die | 67-71° C. | |
| Melt Pressure | | 20-100 bar |

The temperature profile, feed rate, and die size all have an effect on the pressure produced on the die head. A die size of 3-5 mm was used. The temperature profile was kept relatively static. The feed rate was adjusted to maintain a consistent and high pressure on the die head of about 50 bar. A pressure maintained at the die head of about 50 bar or more produced uniform extrudates.

A Carver Press was then used to form the extrudate into pills. A Carver Press is a manual hand press which utilizes a free standing set of Natoli upper and lower punches that meet at the die. Dedicated tooling was made for the experiment in order to produce an embossed, 100 mg pill.

The extrudate was hand cut, based on weight (100 mg). The die was placed on top of the bottom punch, the cut extrudate was placed in the die cavity, and the top punch placed through the top section of the die. The cut extrudate was formed into a pill at no more than 1 metric ton of force using the Carver Press and Natoli die set.

Dissolution Testing

The abuse deterrent pills prepared were tested for dissolution. Dissolution testing was performed with reference to USP Monograph on Oxycodone HCl Tablets. These tests were performed on a dissolution apparatus utilizing UPS <711> Apparatus II (Paddles), with 500 mL de-aerated water as media and a paddle speed of 50 rpm. Japanese Sinker Baskets (Part Number PSCUSBSK-JPMAG) were utilized. A 1 mL sample was pulled at 20 and 45 minutes and submitted for HPLC analysis. HPLC conditions were taken from the USP Monograph in order to observe the release of acetaminophen. The HPLC conditions are as follows: Injection Volume: 20 µL; Flow Rate 1.5 mL/min; Detection: UV at 295 nm; Column Temp: 25° C.; Autosampler Temperature: ambient; Gradient: Isocratic; and Runtime: 5 minutes. The specification for this dissolution testing was NLT 75% (Q=70%) at 45 minutes.

The weight percent of matrix agent (e.g., polyethylene oxide) in the formulation has a direct correlation with both the release profile and ADF properties. The effect of varying the weight percent of the matrix agent (e.g., polyethylene oxide) in the formulation on the release properties and ADF was tested. Two different molecular weight polyethylene oxides were used, namely 300K Daltons and 600K Daltons. The general formulation was tested for dissolution using the two different polyethylene oxides (i.e., 300K Daltons and 600K Daltons). For these experiments, polyethylene glycol was used to offset the differing weight percentages of PEO.

Figure 4:
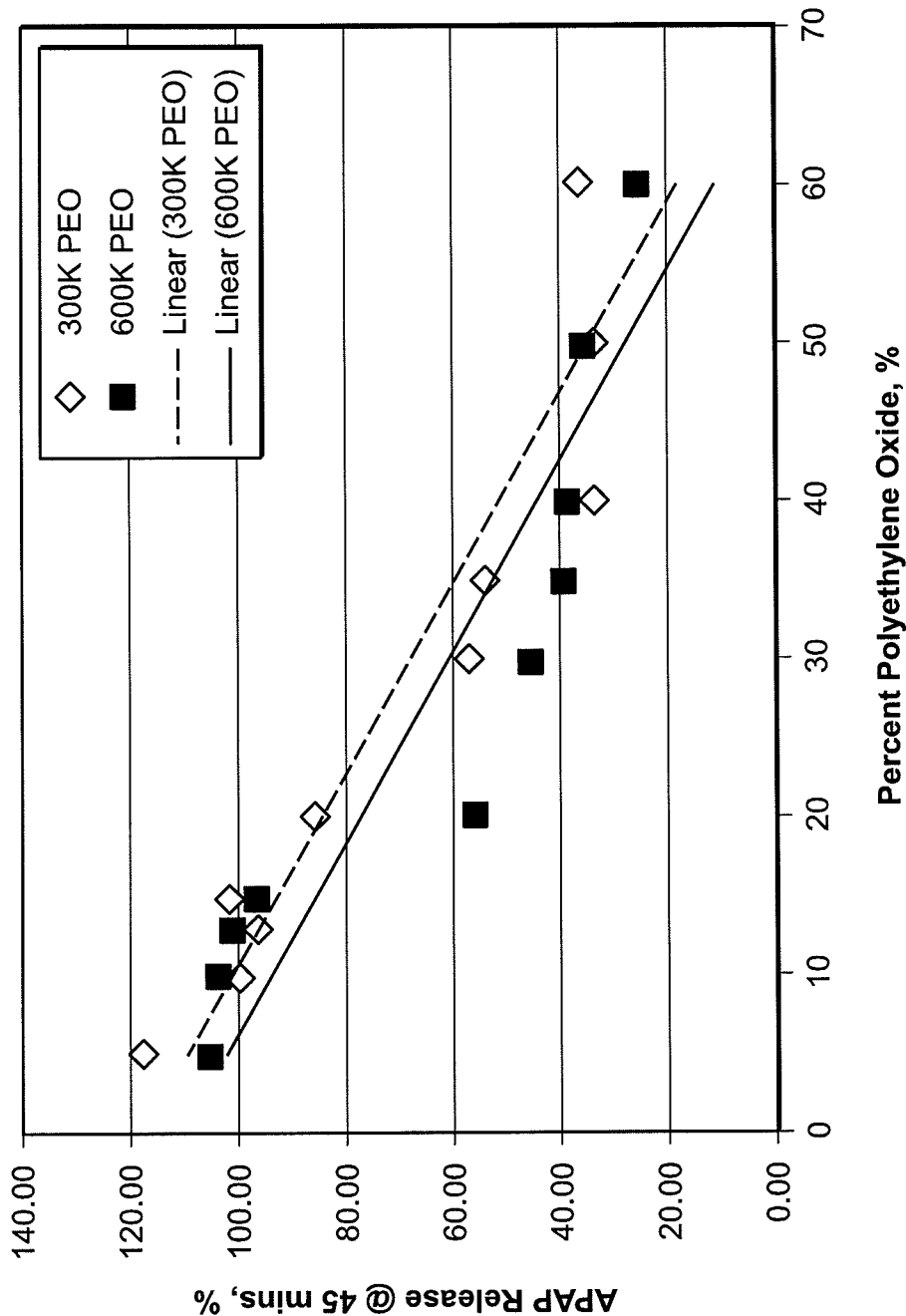
FIG. 4 shows the percent release of the active substance (i.e., acetaminophen dissolution in 45 minutes) versus the weight percent of the matrix agent (e.g., polyethylene oxide or PEO) for two similar abuse deterrent pill formulations having different molecular weight matrix agents (e.g., 300K Daltons PEO vs. 600K Daltons PEO).

FIG. 4 shows the percent release of the active substance (i.e., acetaminophen dissolution in 45 minutes) versus the weight percent of the matrix agent (e.g., polyethylene oxide or PEO) for two similar abuse deterrent pill formulations having different molecular weight matrix agents (e.g., 300K Daltons PEO vs. 600K Daltons PEO). Based on FIG. 4, the more polyethylene oxide present in the formulation the lower the percent release of active after 45 minutes.

Abuse Deterrent Testing—Coffee Grinder Assay

Figure 5:
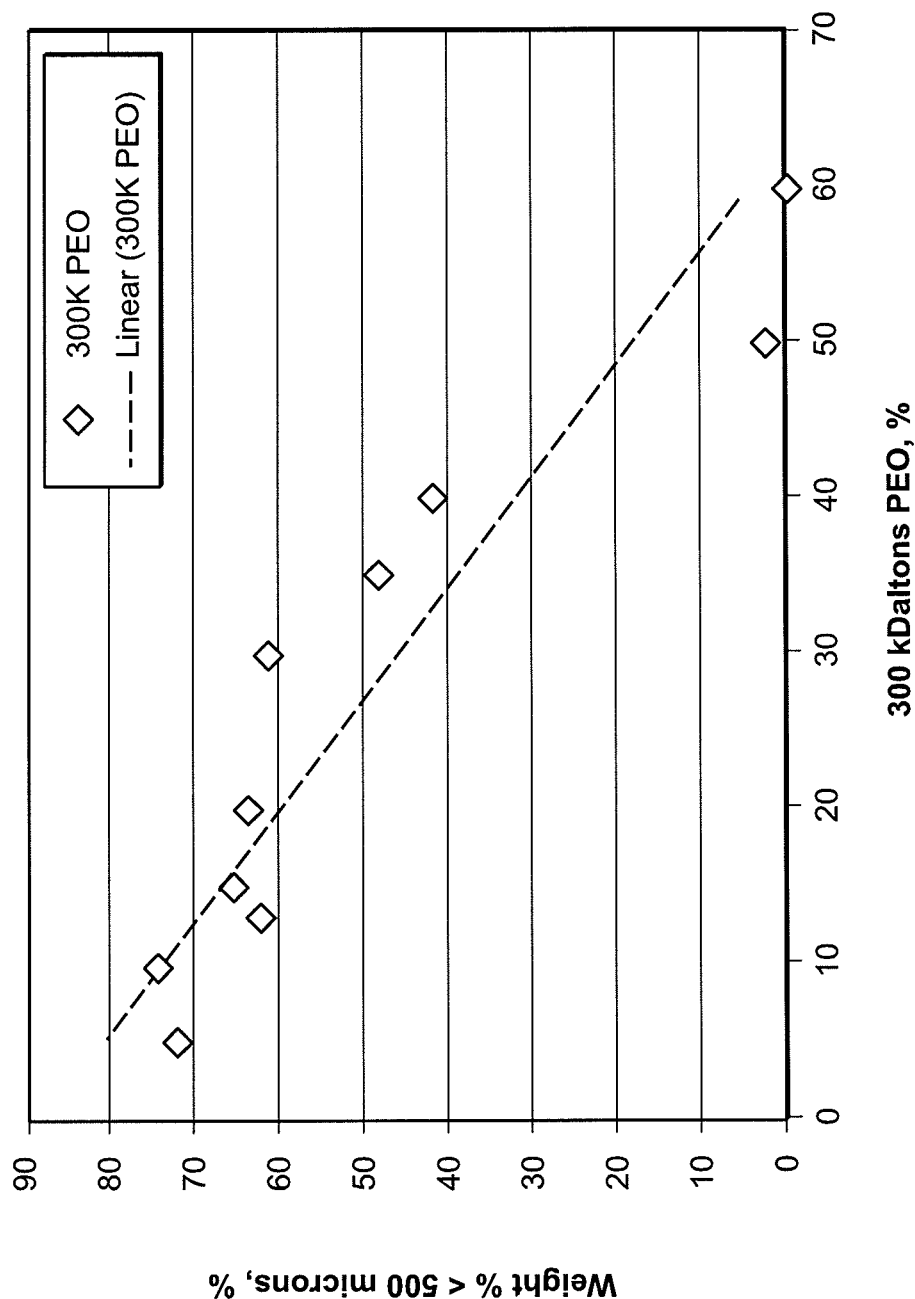
FIG. 5 shows the weight percent of particles formed by grinding which have a particle size less than 0.5 mm versus the weight percent of matrix agent (e.g., PEO). The particles are formed by grinding the formulation in a commercial coffee grinder for at least 30 seconds.

The abuse deterrent pills were also tested for resistance to pulverizing/grinding using a coffee grinder assay. The tested formulations contained only 300K Dalton polyethylene oxide. The Wt % of the polyethylene oxide was varied. Polyethylene glycol was again used to offset the differing weight percentages of PEO. Three (3) pills for each specific Wt % of polyethylene oxide were selected and placed in a commercially available coffee grinder (Mr. Coffee®, model number IDS55). The coffee grinder was run for 30 seconds with occasional pulsing. The grinded pills were tested for particle size analysis using a sonic sifter (screen size 35 Mesh) for 2 minutes. The 35 Mesh corresponds to a sieve size of 0.5 mm. The amount of particles below 0.5 mm for each formulation is shown in FIG. 5. FIG. 5 shows that with increasing weight percent of polyethylene oxide the ADF properties are enhanced. The percent of particles smaller than 0.5 mm decreases with increasing weight percent of polyethylene oxide. These results show that by increasing the content of polyethylene oxide the percentage of particles small enough to be abused through means of insufflation is decreased.

Example 2

Immediate release abuse deterrent pills containing acetaminophen or oxycodone HCl were manufactured according to the formulation provided in Table 1.

A 150 g batch of each formulation was processed and formed into abuse deterrent pill by the process described in Example 1. Exemplary extruder operating temperatures and pressures are provided in Table 29.

TABLE 5

Extrusion Temperature and Pressure

|  | Temp | Pressure |
| --- | --- | --- |
| Zone 1 | 63-67° C. |  |
| Zone 2 | 57-61° C. |  |
| Zone 3 | 57-61° C. |  |
| Zone 4 | 58-62° C. |  |
| Zone 5 | 58-62° C. |  |
| Zone 6 | 58-62° C. |  |
| Zone 7 | 58-62° C. |  |
| Zone 8 | 58-62° C. |  |
| Zone 9 | 58-62° C. |  |
| Zone 10 | 58-62° C. |  |
| Die | 68-72° C. |  |
| Actual Melt Pressure |  | 20-100 bar |

All of the abuse deterrent pills were tested for dissolution and abuse deterrence using the tests described in Example 1. All abuse deterrent pills exhibited a greater than 80% of particles having a particle size greater than 0.5 mm in the coffee grinder assay. All abuse deterrent pills also exhibited a more than 75% release within 45 minutes during dissolution testing.

In particular, abuse deterrent pills containing oxycodone HCl were tested for dissolution according to the test described in Example 1. The dissolution results, listed as percent label claim of oxycodone, are shown in Table 6.

TABLE 6

Dissolution Data

| Sample | % Label Claim |
| --- | --- |
| Abuse Deterrent Pill, Test Formulation 1 | |
| 20 Minutes (average of 3 pills) | 54.9 |
| 45 Minutes (average of 3 pills) | 81.3 |
| Abuse Deterrent Pill, Test Formulation 2 | |
| 20 Minutes (average of 3 pills) | 57.8 |
| 45 Minutes (average of 3 pills) | 87.9 |

As shown in Table 6, the release profiles are comparable and both are consistent with immediate release formulations.

The abuse deterrent pills were put on accelerated stability under 40° C./75% RH conditions for 1 and 2 Months. Dissolution testing was repeated. The results are shown in the Table 7.

TABLE 7

Dissolution Data on Stability

| Sample | % Label Claim (1 Mo) | % Label Claim (2 Mo) |
| --- | --- | --- |
| Abuse Deterrent Pill, Test Formulation 1 | | |
| 20 Minutes (average of 6 pills) | 56.39 | 54.24 |
| 45 Minutes (average of 6 pills) | 85.18 | 81.63 |
| Abuse Deterrent Pill, Test Formulation 2 | | |
| 20 Minutes (average of 6 pills) | 44.80 | 51.12 |
| 45 Minutes (average of 6 pills) | 75.75 | 80.24 |

As shown in Table 7, the release profile and the percent label claim for the abuse deterrent pills on stability are comparable to each other and to the original pills. The release profile for the abuse deterrent pills is consistent with immediate release formulations. The abuse deterrent pills exhibited excellent stability under accelerated conditions.

Abuse Deterrent Testing—Coffee Grinder Assay

The abuse deterrent pills containing oxycodone HCl were tested for resistance to pulverizing/grinding using the coffee grinder assay described in Example 1. Three (3) pills were selected and placed in the coffee grinder. The coffee grinder was run for 30 seconds with occasional pulsing. The grinded pills were tested for particle size analysis using a sonic sifter (screen size 35 Mesh). The results are shown in Table 8.

TABLE 8

Pulverizing/Grinding Test (30 seconds)

|  | Gross Wt (mg) | Tare Wt (mg) | Net Wt (mg) | % |
| --- | --- | --- | --- | --- |
| 35 Mesh | 40461.70 | 40208.03 | 253.67 | 84 |
| Pan | 160822.45 | 160822.45 | 49.54 | 16 |
| | | Total | 303.21 | 100 |

The tested was repeated with the coffee grinder run for a longer period (2 minutes). The grinded pills were tested for particle size analysis using a sonic sifter (screen size 35 Mesh). The results are shown in Table 9.

TABLE 9

Pulverizing/Grinding Test (2 minutes)

| | Gross Wt (mg) | Tare Wt (mg) | Net Wt (mg) | % |
|---|---|---|---|---|
| 35 Mesh | 40411.21 | 40209.15 | 202.06 | 73 |
| Pan | 160913.98 | 160839.25 | 74.73 | 27 |
| | | Total | 276.79 | 100 |

As shown in Tables 8 and 9, a majority of the grinded pills (84% and 73%) have a particle size larger than 0.5 mm. These pills are abuse deterrent compliant.

Additional abuse deterrent pills containing oxycodone HCl or hydrocodone bitartrate were tested for resistance to pulverizing/grinding using the coffee grinder test described above. The results are shown in Table 10. A majority of the grinded pills (89%+) has a particle size larger than 0.5 mm. These pills are abuse deterrent compliant.

TABLE 10

Pulverizing/Grinding Test (2 minutes)

| | % particles > 500 microns | % particles < 500 microns |
|---|---|---|
| Test Formulation 3 (oxycodone HCl) | 89 | 11 |
| Test Formulation 4 (hydrocodone bitartrate) | 89 | 11 |

The abuse deterrent pills were also tested for hardness. Hardness testing was performed using a Sotax HT1 hardness testing machine. Two different formulations were tested for hardness, one containing acetaminophen and one containing oxycodone HCl.

For each formulation, three (3) formed pills were tested for hardness. All the hardness tested pills exhibited a hardness of >999N.

Example 3

In order to attain the release profile required by USP standards for immediate release, the use of a disintegrant was tested. Several disintegrants were evaluated including croscarmellose sodium, sodium starch glycolate, cross-linked polyvinylpyrrolidone, sodium bicarbonate/citric acid and alginic acid. These disintegrants work though several methods such as swelling, wicking, and deformation in an aqueous environment to break up a formulation and thus increase surface area to aid in rapid API release.

Experiments utilizing polyethylene oxide 300K Daltons showed no significant improvement in dissolution rates with increased weight percent of croscarmellose sodium (CCS). CCS is water soluble and can form a gel at increasing percentages which may prevent disintegration. Sodium starch glycolate (SSG) was tested and found to rapid swell with minimal gelling effects. SSG was tested alone as well as with 5 Wt % and 10 Wt % sodium bicarbonate/citric acid acting as an effervescent. All combinations produced passing dissolution at 45 minutes. Additional experiments utilizing alginic acid produced similar passing dissolution results at 45 minutes.

Cross-linked polyvinylpyrrolidone was also tested. Cross-linked polyvinylpyrrolidone was tested alone as well as with 5 Wt % and 10 Wt % sodium bicarbonate/citric acid. Cross-linked polyvinylpyrrolidone also produced passing dissolution results. Cross-linked polyvinylpyrrolidone is highly hydrophilic and water insoluble. It acts through a wicking and swelling mechanism. Due to it being water insoluble, it does not form a gel in any concentration. Cross-linked polyvinylpyrrolidone provided better dissolution results regardless of Wt % sodium bicarbonate/citric acid which is believed to be due to its insoluble, non-gel forming nature. Thus, cross-linked polyvinylpyrrolidone was determined to be a preferred disintegrant for this formulation.

Extraction Example

The inclusion of one or more dyes in a drug formulation is one method to render a formulation abuse deterrent. Significant discoloration of an extraction product from a formulation subject to abuse can discourage a potential abuser from using (e.g., injecting or ingesting) the extraction product. A study was conducted to investigate the effect of dyes in the formulations of the present disclosure. Extraction products from whole or cut formulations were visually inspected to determine abuse deterrence following alcohol extraction, and also following subsequent filtration.

The purpose of this study is to perform and summarize the results of an alcohol extraction, filtration, and visual examination of the resulting extraction solution for different formulations. Formulations of CII narcotic drug products can be modified from their intended dosage form in order to receive immediate release of the full dose of the active pharmaceutical ingredient into the body. This is known as making the drug product "abusable." Formulation development has occurred which is intended to reduce the ability of patients to modify the products into this "abusable" form. Extrusion and compress-and-curing are two methods for manufacturing CII drug products. Both methods, when formulated appropriately, possess characteristics which reduce the ability of patients to modify the products into an "abusable" form (when compared to traditional methods).

Twin Screw extrusion can be described as mixing a blended formulation by using shear forces. The co-rotating screws create shear/frictional forces through material contact between the two screws and between the screws and barrel wall. The shear forces work on the material based on its viscosity (inter-particulate friction) to create a homogenous polymer melt. The heated barrels control the melt by maintaining constant temperatures in the various zones of the extruder as well as add additional heat to maintain energy in the process. This happens in a simultaneous continuous process while the material is transferred through the extruder. The polymer melt can then be pushed through a die to form a uniform extrudate. This differs from compress-and-curing which can be described as initially compressing (with force) the blended formulation and then curing (with heat) after the compression in a separate sequential process to produce a finished drug product. CII drug products which utilize each manufacturing method are currently commercially available. In some embodiments, the formulation of the present disclosure is formed by an extrusion process under sufficient shear stresses to impart strength and stability to the formulation. The formulation can be prepared using an extruder wherein shear forces, pressure, and heating are be applied together or separately in different zones of the extruder. In some embodiments, the formulation is prepared by reaching a melt flow temperature of the specific formulation in the extruder to assist in producing a uniform extrudate (i.e., localized uniformity). Compress-and-curing formulations are not similarly prepared.

Three principal methods of modifying CII drug products in order to make them "abusable" exist, namely cutting, grinding, and extraction. Cutting the dosage form can be performed in order to increase the surface area of the product prior to ingesting it in an effort to increase the rate of dissolution into the digestive tract. Cutting can also be used to increase the efficiency of extraction by breaking/removing the aqueous, non-ethanol soluble coating applied to many commercially available drugs. Cutting alone, however, is not sufficient to render a formulation abusable. Readily available tools used for cutting are razor blades and common kitchen scissors. Grinding the dosage form is performed in order to decrease the particle size of the product in an effort to insufflate (snort) for immediate release into the blood vessels of the nasal passages. Additional abuse pathways exist which follow the grinding of the product. A readily available tool used for grinding is a commercially available coffee grinder. Extraction is performed in order to dissolve the active pharmaceutical ingredient of the dosage form into a liquid which can be filtered and subsequently swallowed, injected, or otherwise abused. A readily available tool used for extraction is high potency alcohol (i.e., ≥190 proof (95%)).

Color is one identifying characteristic of commercial drug products. Color can be applied to the dosage form in two ways: dye or coating. High potency alcohol (i.e., ≥190 proof (95%)) is one extraction solvent that can be used by abusers for APIs which are insoluble in water or in order to separate the API from other water soluble excipients. Dyes or coatings can potentially be used to alter the physical appearance of the extracted solution of drug product (i.e., turn the resulting solution a noticeable color).

In this study, 190 proof ethanol was utilized as an extraction solvent. A commercially available coffee filter was used to filter out any particulate matter of several drug products. The resulting solution was analyzed for physical appearance. The difference in physical appearance (if any) between drug products which are dyed or coated was evaluated.

Additionally, a non ADF drug product which utilizes traditional compression manufacturing methods (Roxicodone® 15 mg, manufactured by Mallinckrodt, Inc.) was evaluated for comparison purposes.

Experimental: The samples tested include ADF Oxycodone 5 mg and 30 mg (Immediate Release) and ADF Oxycodone 10 mg and 80 mg (Extended Release) as described in the present disclosure, as well as Roxicodone® 15 mg (Mallinckrodt, Inc.), Opana® ER 5 mg (reformulated) (Endo Health Solutions); Opana® ER 40 mg (reformulated) (Endo Health Solutions); Oxycontin® 10 mg (reformulated) (Purdue Pharma); Oxycontin® 40 mg (reformulated) (Purdue Pharma); Oxycontin® 60 mg (reformulated) (Purdue Pharma); Oxycontin® 80 mg (reformulated) (Purdue Pharma). A summary of all of the samples tested is provided in the table below.

TABLE 11

List of Samples Tested Dosage Units Descriptions

| Sample | Sample Name | Manufac. Process | Manufac. Process Color | API | Release Timeframe |
|---|---|---|---|---|---|
| 1 | Roxicodone ® 15 mg | Compression | Dye | Oxycodone | Immediate |
| 2 | IR 5 mg | Extrusion | Dye | Oxycodone | Immediate |
| 3 | IR 30 mg | Extrusion | Dye | Oxycodone | Immediate |
| 4 | ER 10 mg | Extrusion | Dye | Oxycodone | Extended |
| 5 | ER 80 mg | Extrusion | Dye | Oxycodone | Extended |
| 6 | Opana ® ER 5 mg | Extrusion | Coating | Oxymorphone | Extended |
| 7 | Opana ® ER 40 mg | Extrusion | Coating | Oxymorphone | Extended |
| 8 | Oxycontin ® 10 mg | Compress & Cure | Coating | Oxycodone | Controlled |
| 9 | Oxycontin ® 40 mg | Compress & Cure | Coating | Oxycodone | Controlled |
| 10 | Oxycontin ® 60 mg | Compress & Cure | Coating | Oxycodone | Controlled |
| 11 | Oxycontin ® 80 mg | Compress & Cure | Coating | Oxycodone | Controlled |

The formulations of the samples of the present disclosure tested, i.e., samples 2-5, are provided in the table below.

TABLE 12

Formulations of Samples Tested

| Component | Sample 2 | Sample 3 | Sample 4 | Sample 5 |
|---|---|---|---|---|
| Oxycodone HCl | 5.00% | 30.00% | 5.00% | 33.33% |
| PEO, 100K Daltons | 35.00% | 35.00% | 40.00% | 40.00% |
| Microcrystalline Cellulose PH 101 | 22.25% | 12.25% | | |
| Lactose Monohydrate 316 | 21.00% | 11.65% | | |
| Hypromellose, K100M | 37.50% | 20.00% | | |
| PEG, 8K Daltons | 15.00% | 10.00% | 15.75% | 4.67% |
| Citric Acid | 1.00% | 1.00% | 1.00% | 1.00% |
| Dye | 0.75% | 0.10% | 0.75% | 1.00% |
| Total weight | 100 mg | 100 mg | 200 mg | 240 mg |
| Release characteristics | IR | IR | ER | ER |

In additional embodiments of the present disclosure, the amount of active substance in the formulation can range from about 0.50 Wt % to about 40 Wt %. Particularly, the amount of active substance in the formulation may range from about 1.0 Wt % to about 35 Wt %, or from about 5.0 Wt % to about 33 Wt %. In additional embodiments of the present disclosure, the amount of plasticizer (e.g., PEG) can range from about 0.25 Wt % and about 20 Wt % plasticizer.

For each sample, both whole and cut dosage units were tested. For whole dosage units, two (2) whole dosage units were placed in a 25 mL Erlenmeyer flask containing 10 mL of EtOH. For cut dosage units, all cut pieces of the dosage unit were placed in similar flasks. Cut dosage units were cut into about 8 pieces using diagonal pliers. Each flask was sealed with parafilm and shaken on a platform shaker for at least 10 hours at about 150 rpm. The resulting solution was filtered through a coffee filter to remove any particulate matter. The filtered solution was collected in a 50 mL Nessler color comparison tube. After 30 minutes, each sample tube was visually examined for color (if any), clarity/turbidity, and if any noticeable difference in filtered solution volume exists (i.e., a significant decrease from the original 10 mL EtOH). The results for the whole and cut dosage units are provided in the two tables below.

ing a sample with a dark, significant color, (0—no color; 1—faint; 2—light; 3—medium; 4—brilliant; and 5—dark). Samples with at least light color, including dark coloration, can deter potential abusers from injecting or ingesting the filtered extract (e.g., colors 2 and above, 3 and above, 4 and above, or 5). The table below shows the color number assignments for the syringe filtered cut dosage unit solutions.

TABLE 13

Whole Dosage Unit Extraction Data
Visual Examination-Whole Dosage Units

| Sample | Sample Name | Color Change | Color Observed | Intensity | Notes (clarity/turbidity, volume change, etc.) |
|---|---|---|---|---|---|
| 1 | Roxicodone ® 15 mg | Yes | Yellow | Faint | Clear, no volume change |
| 2 | IR 5 mg | Yes | Yellow | Dark | Clear, no volume change |
| 3 | IR 30 mg | Yes | Blue | Medium | Clear, ~1 mL volume decrease |
| 4 | ER 10 mg | Yes | Blue | Dark | Clear, ~3 mL volume decrease |
| 5 | ER 80 mg | Yes | Green | Dark | Clear, ~4 mL volume decrease |
| 6 | Opana ® ER 5 mg | No | None | None | Clear, no volume change |
| 7 | Opana ® ER 40 mg | Yes | Yellow | Faint | Clear, no volume change |
| 8 | Oxycontin ® 10 mg | Yes | White | Faint | Slightly turbid, no volume change |
| 9 | Oxycontin ® 40 mg | Yes | White | Faint | Slightly turbid, no volume change |
| 10 | Oxycontin ® 60 mg | Yes | Red | Faint | Slightly turbid, no volume change |
| 11 | Oxycontin ® 80 mg | Yes | Blue | Faint | Slightly turbid, no volume change |

TABLE 14

Cut Dosage Unit Extraction Data
Visual Examination-Cut Dosage Units

| Sample | Sample Name | Color Change | Color Observed | Intensity | Notes (clarity/turbidity, volume change, etc.) |
|---|---|---|---|---|---|
| 1 | Roxicodone ® 15 mg | Yes | Yellow | Faint | Clear, no volume change |
| 2 | IR 5 mg | Yes | Yellow | Dark | Clear, no volume change |
| 3 | IR 30 mg | Yes | Blue | Medium | Clear, ~1 mL volume decrease |
| 4 | ER 10 mg | Yes | Blue | Dark | Clear, ~3 mL volume decrease |
| 5 | ER 80 mg | Yes | Green | Dark | Clear, ~4 mL volume decrease |
| 6 | Opana ® ER 5 mg | No | None | None | Clear, ~1 mL volume decrease |
| 7 | Opana ® ER 40 mg | Yes | Yellow | Faint | Clear, ~1 mL volume decrease |
| 8 | Oxycontin ® 10 mg | Yes | White | Faint | Slightly turbid, ~1 mL volume decrease |
| 9 | Oxycontin ® 40 mg | Yes | White | Medium | Turbid, ~1 mL volume decrease |
| 10 | Oxycontin ® 60 mg | Yes | Red | Medium | Turbid, ~2 mL volume decrease |
| 11 | Oxycontin ® 80 mg | Yes | Blue | Faint | Turbid, slight volume change |

During filtration, samples passed through the filter at various rates. For example, samples 1 and 6-11 took approximately 20 seconds for the entire volume to completely pass through the coffee filter. Samples 2 and 3 took approximately 15 minutes for the entire volume to completely pass through the coffee filter. Samples 4 and 5 took approximately 60 minutes for the entire volume to completely pass through the coffee filter. After filtration, samples 2-5 were uniform in color after sitting for approximately 30 minutes, while samples 8-11 had significant sediment at the bottom of the comparison tubes. Samples 1, 6 and 7 had no noticeable sediment but were significantly less colored than the batches of the present disclosure.

Approximately 5 mL of the filtrate from each cut dosage form sample was passed through a 25 mm, 0.2 μm PTFE Titan syringe filter (Scientific Resources, Inc. Cat No. 42225-PC, Lot 709029003054). Each resulting solution was then assigned a number according to a scale of 0-5, with 0 (zero) representing a sample with no color and 5 represent-

TABLE 15

Cut Dosage Unit Color Numbers
Visual Examination-Cut Dosage Units

| Sample Number | Sample Name | Color |
|---|---|---|
| 1 | Roxicodone ® 15 mg | 1 |
| 2 | IR 5 mg | 5 |
| 3 | IR 30 mg | 3 |
| 4 | ER 10 mg | 5 |
| 5 | ER 80 mg | 5 |
| 6 | Opana ® ER 5 mg | 0 |
| 7 | Opana ® ER 40 mg | 1 |
| 8 | Oxycontin ® 10 mg | 0 |
| 9 | Oxycontin ® 40 mg | 0 |
| 10 | Oxycontin ® 60 mg | 0 |
| 11 | Oxycontin ® 80 mg | 0 |

In some embodiments, the formulation of the present disclosure incorporates the dye throughout the entire dosage unit as opposed to incorporating the dye only in a coating. The dye can be water soluble, alcohol soluble or both. The dye can have a solubility in water, alcohol or both that is greater than about 0.01 g/100 mL, about 0.1 g/100 mL, about 1 g/100 mL or about 10 g/100 mL. Traditional drug formulation dyes are not soluble, or significantly soluble, in water, alcohol or both. They are often formulated into the coatings of the drug formulations. In some embodiment, the dyes are water soluble, alcohol soluble or both, and are dyes that are approved for, or considered acceptable, for oral administration. In some instances, the solubility of the dye in alcohol is important because of the potential for compounding effects of, and interactions associated with, consuming both alcohol and the extracted API.

The following table lists the relative solubility of exemplary components of a formulation. A number of different dyes are listed along with their solubility information taken from the various literature sources and tested experimentally (200 proof ethanol and filtered through a 0.22 micrometer PTFE filter).

TABLE 16

General Solubility of Exemplary Components

| Exemplary Components | Water Solubility | Alcohol Solubility (Literature) | Alcohol Solubility (tested) |
|---|---|---|---|
| Oxycodone HCl | Yes | Yes | N/A |
| Polyethylene Oxide | Yes | No | N/A |
| Polyethylene Glycol | Yes | Yes | N/A |
| Hydroxypropylmethylcellulose | Yes | No | N/A |
| Microcrystalline Cellulose | No | No | N/A |
| Lactose Monohydrate | Yes | No | N/A |
| FD&C Blue #1 | Yes | Yes | N/A |
| FD&C Blue #2 | Yes | Yes | Yes |
| FD&C Yellow #5 | Yes | Yes | Yes |
| FD&C Yellow #6 | Yes | Yes | Yes |

TABLE 16-continued

General Solubility of Exemplary Components

| Exemplary Components | Water Solubility | Alcohol Solubility (Literature) | Alcohol Solubility (tested) |
|---|---|---|---|
| FD&C Red #40 | Yes | Yes | Yes |
| Lake Dyes | No | No | N/A |

The sediment observed at the bottom of the comparison tubes of the Oxycontin® batches (samples 8-11) is indicative of a suspension rather than a solution. Typically, suspensions can be centrifuged or filtered to obtain a more clear solution (and in some cases, a colorless solution). Conversely, solutions cannot be further centrifuged or filtered using a common household coffee filter or a readily available syringe filter to obtain a more clear solution because the dye is completely dissolved in the solution. Dyed formulations can provide an additional mechanism of abuse deterrence than coated formulations.

The amount of dye present in the formulation can be an amount that produces an extract or a filtered extract using water, alcohol or a combination of both with a color that is greater than 0, or greater than 1, or greater than 2, or greater than 3 or greater than 4 on the visual scale disclosed, or similar scale. The amount of dye can vary depending on the formulation and components present. In some embodiments, the formulation can contain at least 0.1% dye, at least 0.2% dye, at least 0.3% dye, at least 0.4% dye, at least 0.5% dye, at least 0.6% dye, at least 0.7% dye, at least 0.8% dye, at least 0.9% dye, at least 1.0% dye, at least 1.5% dye, at least 2.0%, or any range of these values (e.g., between about 0.1% and about 1.0% dye).

It was also observed that a volume change occurred (~3-4 mL decrease) for samples 4 and 5 following extended filtration time. Certain excipients (e.g., hydroxypropylmethylcellulose) can cause the resulting solution to become too viscous to fully pass through a coffee filter. Additional abuse deterrence (e.g., extended extraction time and volume loss) can be obtained by formulations including hydroxypropylmethylcellulose, or equivalents.

Additional Exemplary Formulations

Additional exemplary formulations of the present disclosure are provided in the tables below.

TABLE 17

Additional Exemplary Formulations

| Component | 15 | 15 | 20 | 30 | 40 | 60 |
|---|---|---|---|---|---|---|
| Oxycodone HCl | 15.00% | 7.50% | 10.00% | 15.00% | 20.00% | 30.00% |
| PEO, 100K Daltons | 35.00% | 40.00% | 40.00% | 40.00% | 40.00% | 40.00% |
| Microcrystalline Cellulose PH 101 | 18.75% | | | | | |
| Lactose Monohydrate 316 | 17.65% | | | | | |
| Hypromellose, K100M | | 33.00% | 31.00% | 29.00% | 29.00% | 28.00% |
| PEG, 8K Daltons | 12.50% | 17.50% | 17.85% | 14.60% | 9.25% | 0.25% |
| Citric Acid | 1.00% | 1.00% | 1.00% | 1.00% | 1.00% | 1.00% |
| Dye | 0.10% | 1.00% | 0.15% | 0.40% | 0.75% | 0.75% |
| Total weight | 100 mg | 200 mg | 200 mg | 200 mg | 200 mg | 200 mg |
| Release characteristics | IR | ER | ER | ER | ER | ER |

TABLE 18

Additional Exemplary Formulations

| Component | | | | |
|---|---|---|---|---|
| Oxycodone HCl | 4.0-6.0% | 28.0-32.0% | 4.0-6.0% | 32.0-35.0% |
| PEO, 100K Daltons | 33.0-37.0% | 33.0-37.0% | 38.0-42.0% | 38.0-42.0% |
| Microcrystalline Cellulose PH 101 | 21.0-24.0% or 15.0-35.0% | 11.0-14.0% or 10.0-25.0% | | |
| Lactose Monohydrate 316 | 19.0-23.0% or 15.0-35.0% | 10.0-15.0% or 10.0-25.0% | | |
| Hypromellose, K100M | | | 36.0-39.0% | 18.0-22.0% |
| PEG, 8K Daltons | 13.0-17.0% | 8.0-12.0% | 14.0-17.0% | 4.0-6.0% |
| Citric Acid | 0.8-1.2% | 0.8-1.2% | 0.8-1.2% | 0.8-1.2% |
| Dye | 0.6-0.9% or 0.5-1.0% | 0.05-0.2% or 0.05-0.5% | 0.6-0.9% or 0.5-1.0% | 0.8-1.2% or 0.5-1.5% |
| Release characteristics | IR | IR | ER | ER |

TABLE 19

Additional Exemplary Formulations

| Component | | | | | | |
|---|---|---|---|---|---|---|
| Oxycodone HCl | 13.0-17.0% | 6.0-9.0% | 8.0-12.0% | 13.0-17.0% | 18.0-22.0% | 28.0-32.0% |
| PEO, 100K Daltons | 33.0-37.0% | 38.0-42.0% | 38.0-42.0% | 38.0-42.0% | 38.0-42.0% | 38.0-42.0% |
| Microcrystalline Cellulose PH 101 | 17.0-20.0% or 15.0-35.0% | | | | | |
| Lactose Monohydrate 316 | 16.0-19.0% or 15.0-35.0% | | | | | |
| Hypromellose, K100M | | 31.0-35.0% | 29.0-33.0% | 27.0-31.0% | 27.0-31.0% | 26.0-30.0% |
| PEG, 8K Daltons | 11.0-14.0% | 16.0-19.0% | 16.0-19.0% | 13.0-16.0% | 8.0-11.0% | 0.2-0.3% |
| Citric Acid | 0.8-1.2% | 0.8-1.2% | 0.8-1.2% | 0.8-1.2% | 0.8-1.2% | 0.8-1.2% |
| Dye | 0.05-0.2% or 0.05-0.5% | 0.8-1.2% or 0.75-1.25% | 0.1-0.3% or 0.1-0.5% | 0.3-0.5% or 0.3-0.8% | 0.6-0.9% or 0.5-1.0% | 0.6-0.9% or 0.5-1.0% |
| Release characteristics | IR | ER | ER | ER | ER | ER |

Cutting Force Example

Figure 6:
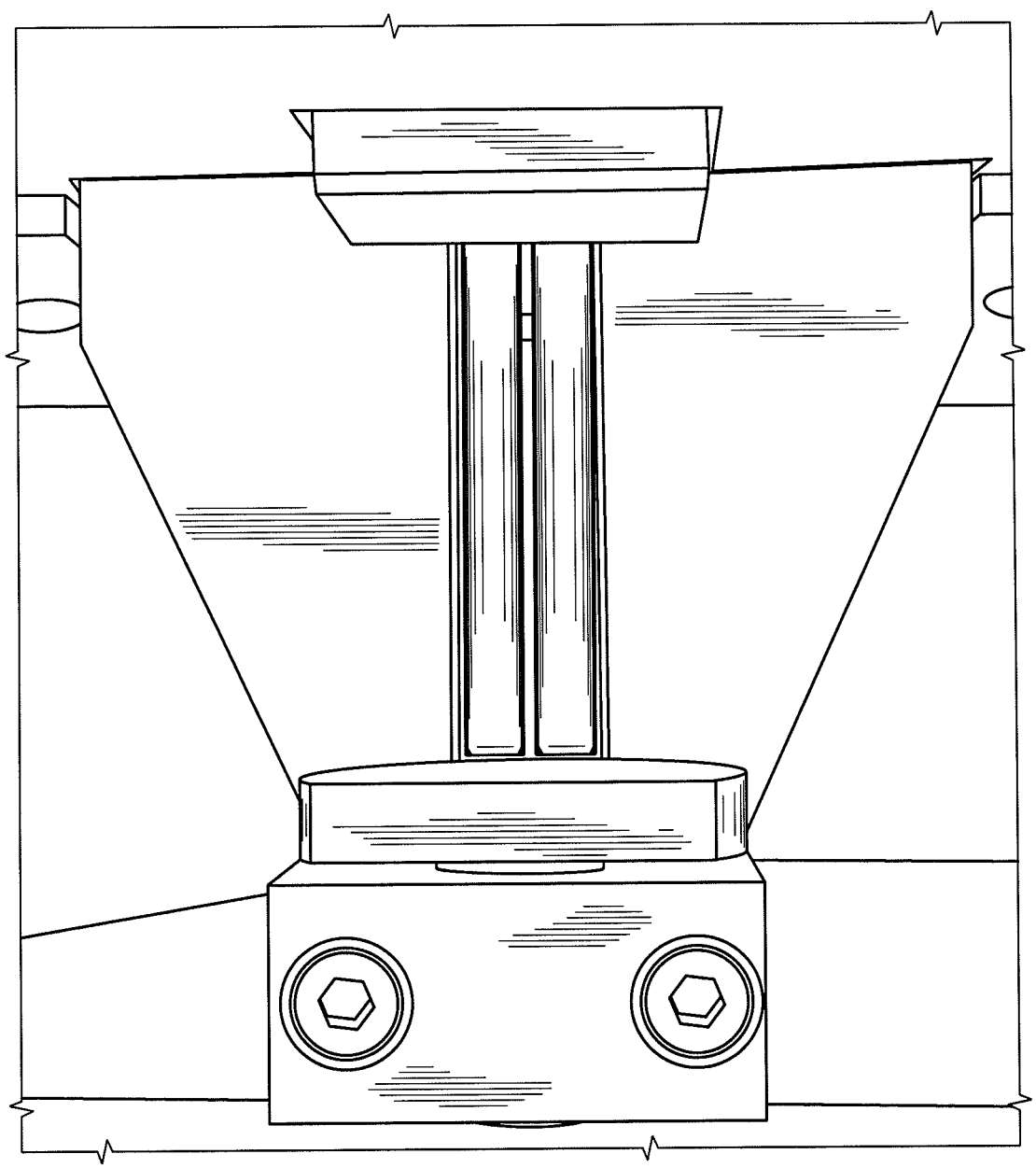
FIG. 6 shows equipment capable of executing traditional "tablet breaking force" analysis.

The existing methodology used to evaluate abuse deterrence in regard to the cutting or breaking of a dosage form is based on the USP's "tablet breaking force" test. This test defines "tablet breaking force" as the force required to cause tablets to fail (i.e., break) in a specific plane. The USP describes the test as follows "[t]he tablets are generally placed between two platens, one of which moves to apply sufficient force to the tablet to cause fracture. The platens should be parallel. Their faces should be polished smooth and precision-ground perpendicularly to the direction of movement. Perpendicularity must be preserved during platen movement, and the mechanism should be free of any bending or torsion displacements as the load is applied. The contact faces must be larger than the area of contact with the tablet." FIG. 6 shows equipment capable of executing traditional "tablet breaking force" analysis.

The USP further explains the applications of tablet breaking force and why it is utilized in the industry. "Tablets must be able to withstand the rigors of handling and transportation experienced in the manufacturing plant, in the drug distribution system, and in the field at the hands of the end users (patients/consumers). Manufacturing processes such as coating, packaging, and printing can involve considerable stresses, which the tablets must be able to withstand. For these reasons, the mechanical strength of tablets is of considerable importance and is routinely measured." The intent of these applications is for traditional formulations which may be subjected to forces which could break the tablets (i.e., vigorous shaking in a tablet bottle). The intent is not to address abuse deterrence potential. Furthermore, this test is only applicable to and instructive to evaluate tablet formulations. The test is not applicable to or instructive to evaluate pill, or other formulations, prepared by extrusion methodologies.

Figure 7:
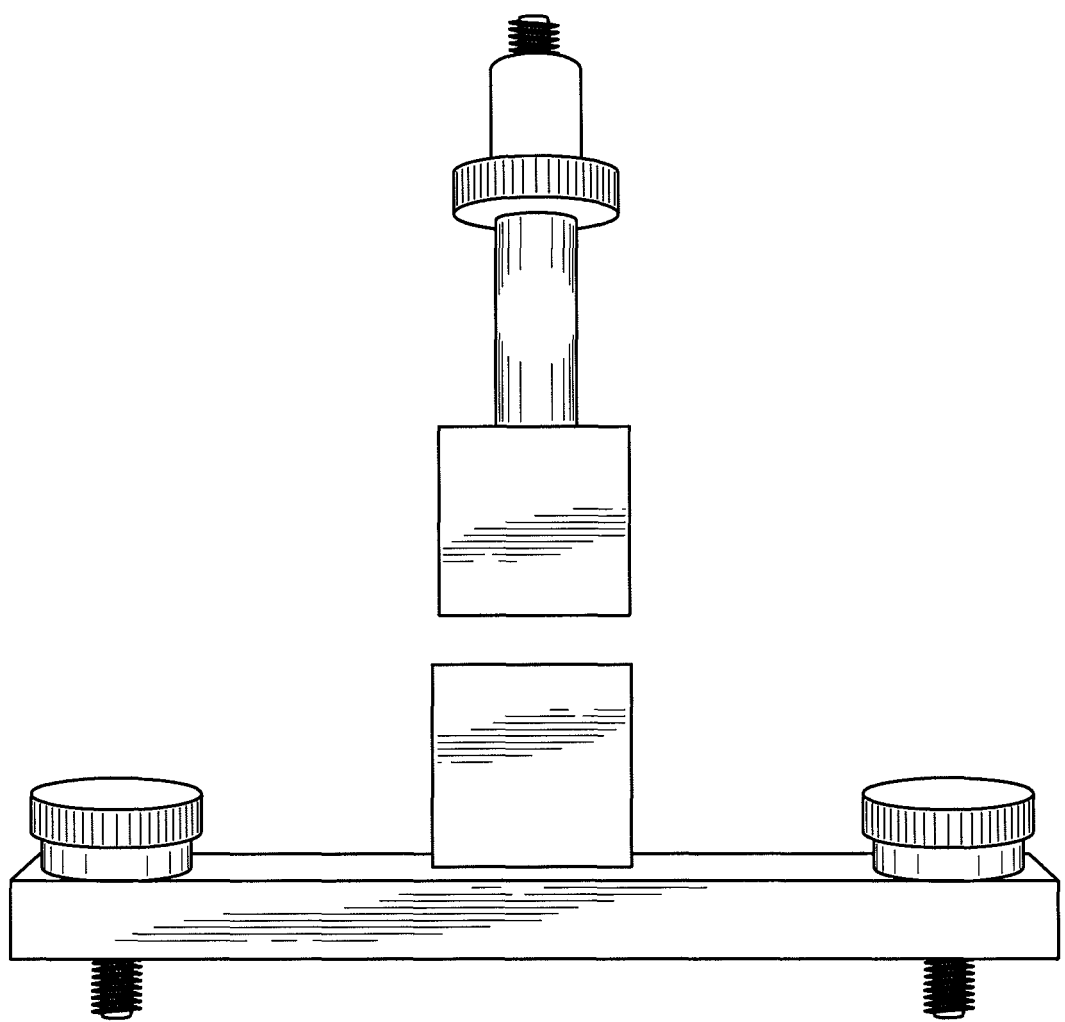
FIG. 7 shows equipment capable of executing a "cutting force" analysis including a top view of a fracture wedge set attachment used to mimic common kitchen scissors.
Figure 8:
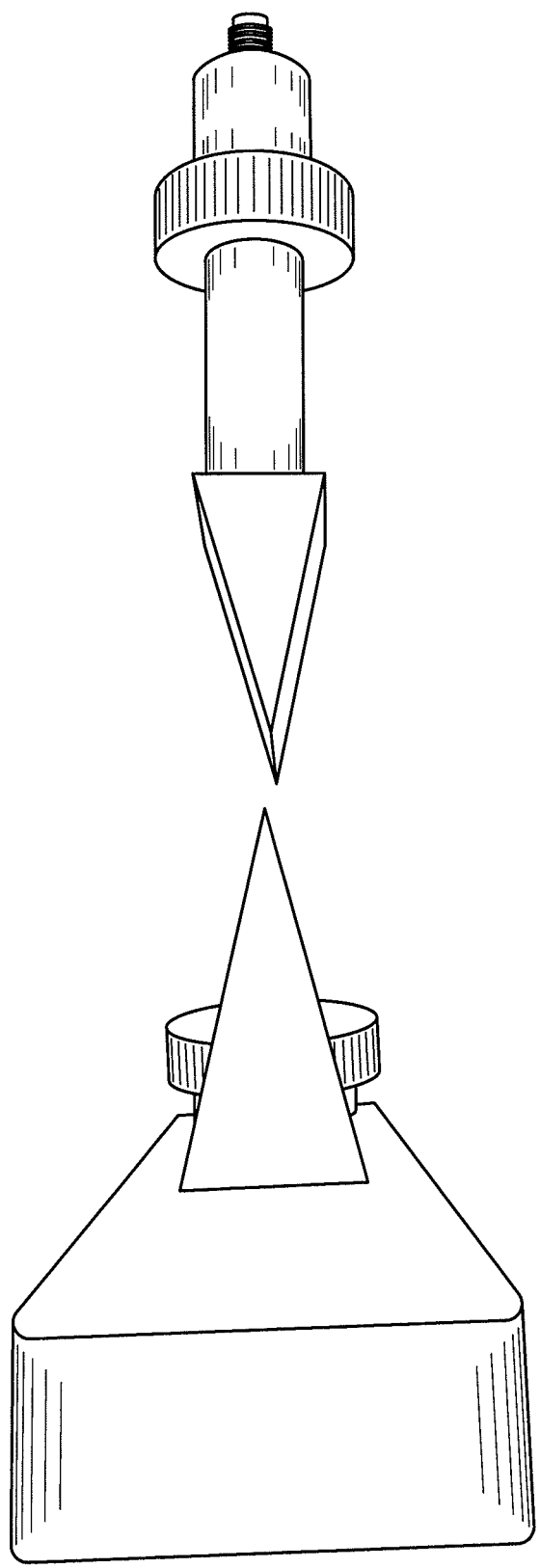
FIG. 8 shows a side view of the fracture wedge set attachment of FIG. 7.

In formulations utilizing excipients such as polyethylene oxide, and using such excipients in an extrusion process, the parameter "tablet breaking force" does not apply. For example, the long molecular chain lengths of the PEO (e.g., 100,000 Daltons-7,000,000 Daltons) cause the drug product (relative to other traditional drug products) to be flattened, but never actually "fail" (i.e., break) when applying "tablet breaking force" in the traditional sense. The traditional application of "tablet breaking force" needs to be modified to evaluate formulations containing malleable excipients (such as PEO) for the "cutting force" of the dosage form, specifically dosage forms which are intended to deter abuse. The modification of the traditional "tablet breaking force" test presented in this study consists of a change from the "platens" utilized to cause the dosage forms to "fail" (i.e., break), namely from contact faces "larger than the area of contact with the tablet" to sharp planes which mimic commonly used tools for abuse. FIGS. 7, 8 and 9 show reference attachments including a fracture wedge set (used to mimic common kitchen scissors, FIGS. 7 and 8 showing different views of the same set) and a razor blade (FIG. 9).

The purpose of this study is to perform and summarize the cutting force needed to cut different formulations of CII narcotic drug products. Texture analysis is the mechanical testing of pharmaceutical products in order to measure their physical properties. A Texture Analyzer XT2i can perform testing of numerous physical properties of pharmaceutical products, including cutting force. The cutting force needed to cut several different formulations of CII narcotic drug products utilizing different attachments on a Texture Analyzer (TE37) was investigated. Multiple tools were utilized to cut drug products with the intent of abuse including two attachments which mimic readily available tools used for abuse (e.g., a razor blade and kitchen scissors). The cutting force for all evaluated drug products were evaluated with each attachment.

Experimental: The samples tested include those samples listed in Table A. The formulations of the samples of the present disclosure tested are listed in Table B. The Texture Analyzer (TE37), Model XT2i HR was operated at the following conditions: Pre Test Speed: 1 mm/s; Test Speed: 0.25 mm/s; Post Test Speed: 10 mm/s; Distance: 99.9% (% Strain); Trigger Type: Auto (Force=0.2N) and Break Detect: Off. A sample size of N=10 was used for each sample per cutting attachment. The cutting force results of the CII narcotic drug products utilizing both cutting attachments (razor blade and fracture wedge set) was determined. FIGS. 10A and 10B show the cutting force data tables for the razor blade and the fracture wedge set.

The individual maximum cutting force needed to cut any tested CII narcotic drug products utilizing the razor blade was 142N (sample 7). The highest average cutting force needed to cut any tested CII narcotic drug products utilizing the razor blade was 131N (sample 7). The individual maximum cutting force needed to cut any tested CII narcotic drug products utilizing the fracture wedge set was 163N (sample 6). The highest average cutting force needed to cut any tested CII narcotic drug products utilizing the fracture wedge set was 156N (sample 6).

All of the tested CII narcotic drug products can indeed be cut, and therefore potentially be abused, with force which is substantially lower than what has been reported using the breaking strength test or equivalent (>500N, See U.S. Pat. No. 8,309,060) utilizing conventional means (i.e., common kitchen scissors or a razor blade). "Flattening" the tablets utilizing forces >500N (with traditional "tablet breaking force" definitions) does not address abuse deterrence potential in the tested CII narcotic drug products.

In one embodiment, the formulation of the present invention exhibits a cutting strength (i.e., force needed to cut the formulation) of greater than about 40 N, about 50 N, about 60 N, about 70 N, about 80 N, about 90 N, about 100 N, about 110 N, about 120 N, or about 130 N, or any range of these values (e.g., between about 40 N and about 120 N), as tested by either the Cutting Force—Razor Blade test or by the Cutting Force—Fracture Wedge Set test, or both.

Samples 4 of 5 of the present disclosure exhibit improved cutting strength compared to the compress-and-cure samples (i.e., samples 8-11). Samples prepared via a compress-and-cure procedure undergo dry mixing of the components only. These components are then compressed into a dosage form, and placing on a drying pan which applies heat to the dosage form. It is believed that compress-and-cure dosage forms are not melted or similarly liquefied to create significant homogeneity within the dosage form as compared to extrusion based procedures. The dosage formulations of the present invention are prepared by extrusion and, therefore, possess significant homogeneity as a result of the extrudate mixing within the extruder under melt flow conditions. The extrudate experiences high shear forces that produce the mechanical energy needed to ensure the required hardness and strength are achieved. The high shear forces can act on select components, for example PEO, to transform them into networks that exhibit increased strength and stability.

Grinding Example

The purpose of this study is to perform and summarize the grinding potential of different formulations of CII narcotic drug products. Texture analysis is the mechanical testing of pharmaceutical products in order to measure their physical properties. The Retsch Knife Mill GRINDOMIX GM200 (TE96) was utilized to mimic a commercially available coffee grinder (Mr. Coffee) in order to grind CII drug products into a particle size that is suitable for intranasal abuse (insufflation). A commercially available coffee grinder was also evaluated for comparison purposes. Particle size analysis was conducted utilizing an ATM L3P Sonic Sifter (TE47), utilizing a 500 micrometer (μm) particle size sieve (35 mesh). For the purposes of this study, any particle less than 500 μm in diameter is considered suitable for intranasal abuse. It is generally accepted as an industry standard that any particle greater than 500 μm in diameter cannot be sufficiently absorbed by the blood vessels in the nasal passages.

The Retsch Knife Mill GRINDOMIX GM200 utilizes a circular blade attachment to mimic commercially available coffee grinders. The GM200 has a top speed of 10,000 revolutions per minute (rpm), while commercially available coffee grinders have a top speed of approximately 20,000 rpm (an approximate two-fold increase in speed when comparing the GM200 to a Mr. Coffee grinder). However, the approximate two-fold increase in blade diameter (118 mm vs. 60 mm, when comparing the GM200 to a Mr. Coffee grinder, respectively) compensates for the approximate two-fold decrease in top speed via the inversely proportional relationship of the two variables. Further, the torque provided by the GM200 is significantly higher than the torque provided by a Mr. Coffee grinder (0.860 Nm (Newton meters) of the GM200 vs. 0.062 Nm of the Mr. Coffee grinder, respectively), which additionally illustrates the ability (or lack thereof) of the Mr. Coffee grinder to modify the drug products into a particle size suitable for intranasal abuse. The study evaluated the difference in particle sizes of several different formulations of CII narcotic drug products following modification (grinding) by the GM200 and Mr. Coffee grinder.

Additionally, a non ADF drug product which utilizes traditional compression manufacturing methods (Roxicodone® 15 mg, manufactured by Mallinckrodt, Inc.) was evaluated for comparison purposes.

Experimental: The samples tested include those samples listed in Table A. The formulations of the samples of the present disclosure tested are listed in Table B. The following test equipment was used: Retsch Knife Mill GRINDOMIX GM200 (TE96), Coffee Grinder (Mr. Coffee), ATM L3P Sonic Sifter (TE47), 500 μm sieve (35 mesh) and a Shimpo Instruments Tachometer (TE31). The following testing conditions were used: Analysis speed: 10,000 rpm (GM200), 20,000 rpm (Mr. Coffee); Analysis time: 30 seconds; Sieve Size: 500 μm (35 mesh); Analysis time: 2 minutes (no pulse). Each sample was prepared in triplicate (N=3).

For each sample, three (3) dosage units were weighed and tested. The following conditions were used with the TE96: a 30 second analysis time and a speed of 10,000 rpm. Both parameters were set prior to each analysis. The composite sample was transferred to a tared weigh boat and the weight of the sample was recorded. The following equation was used to calculate the % sample loss:

$$\text{Sample Loss } (\%) = 100 - \left(\frac{\text{Analyzed Sample (mg)}}{\text{Sample Weight (mg)}} \times 100\right)$$

The weight of the 35 mesh sieve and sample pan was recorded. The testing apparatus was assembled with the 35 mesh sieve above the sample pan. The composite sample was transferred to the testing apparatus and analyzed utilizing the following parameters: 2 minute analysis time and no pulse. The analyzed 35 mesh sieve and sample pan were weighed. The % material remaining on the 35 mesh sieve (≥500 μm) and in the sample pan (≤500 μm) was calculated using the following equation:

$$\text{Percent on Sieve (\%)} = \frac{\text{Weight of Sample on Sieve (mg)}}{\text{Total Weight of Sample on Sieve (mg)}} \times 100$$

The procedure was repeated for the Mr. Coffee grinder in place of the TE96. The Mr. Coffee grinder has 1 operating speed (~20,000 rpm). The particle size analysis and grinding results are shown in FIGS. 11A, 11B, and 12A-12F.

Figure 14:
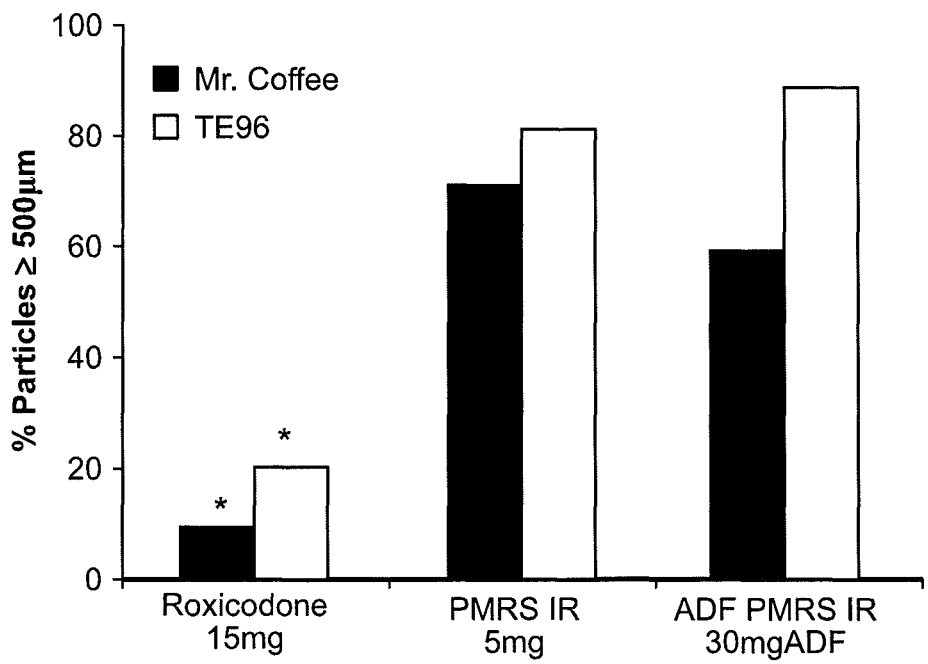
FIG. 14 shows a representation of particle size results (%≥500 μm) when comparing the tested Immediate Release (IR) Roxicodone® batch vs. the formulations of the present disclosure (e.g., IR batches) utilizing both TE96 and the Mr. Coffee grinder.

FIG. 14 shows a representation of particle size results (%≥500 μm) when comparing the tested Immediate Release (IR) Roxicodone® batch vs. the formulations of the present disclosure (e.g., IR batches) utilizing both TE96 and the Mr. Coffee grinder.

Figure 15:
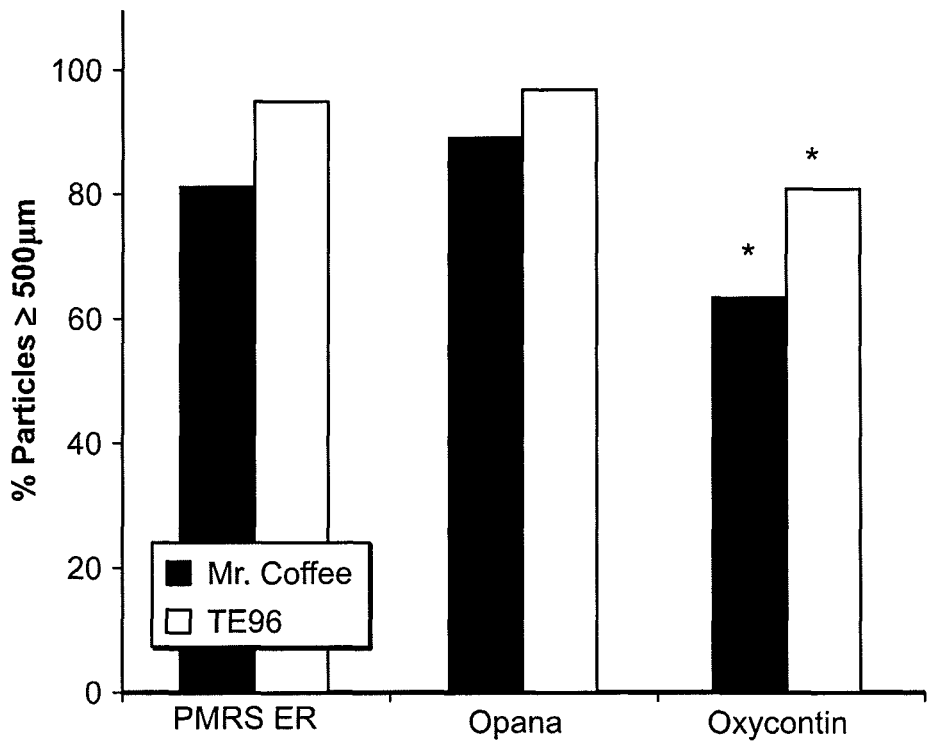
FIG. 15 shows a representation of particle size results (%≥500 μm) when comparing the tested Extended Release (ER) CII narcotic drug products between manufacturers.

FIG. 15 shows a representation of particle size results (%≥500 μm) when comparing the tested Extended Release (ER) CII narcotic drug products between manufacturers.

The Roxicodone® batch provides statistically different (lower) amounts of particles ≥500 μm than the formulations of the present disclosure (e.g., IR samples) following grinding and particle size analysis. Statistical significance was tested against a 95% confidence interval or a p-value of less than 0.05. Combined Oxycontin® batches provide statistically different (lower) amounts of particles ≥500 μm than combined formulations of the present disclosure (e.g., ER samples and combined Opana® batches following grinding and particle size analysis as described in the protocol.

The results were combined per manufacturer, i.e. the present disclosure, Opana® ER batch results, and Oxycontin® results, and analyzed as groups. The combined Opana® batches provide statistically similar amounts of particles ≥500 μm as the combined formulations of the present disclosure (e.g., ER samples) following grinding and particle size analysis.

Example 4

Abuse deterrent formulations were prepared containing both a dye and an alcohol purity decreasing agent. Table 20 shows an exemplary formulation.

TABLE 20

Exemplary Abuse Deterrent Formulation Ranges

| Components | Wt % | Wt % | Wt % |
|---|---|---|---|
| Active | 3.0-7.0 | 13.0-17.0 | 28.0-32.00 |
| Matrix | 33.0-37.0 | 33.0-37.0 | 33.0-37.0 |
| Plasticizer | 20.0-25.0 | 15.0-20.0 | 8.0-12.0 |
| Filler | 20.0-25.0 | 15.0-20.0 | 8.0-12.0 |
| Purity Decreasing Agent | 8.0-12.0 | 8.0-12.0 | 8.0-12.0 |
| Preservative | 0.5-2.0 | 0.5-2.0 | 0.5-2.0 |
| Dye | 2.0-6.0 | 2.0-6.0 | 2.0-6.0 |

TABLE 21

Exemplary Abuse Deterrent Formulation for 100 mg IR pill

| | 100 mg IR Pill | | |
|---|---|---|---|
| Components | 5 Wt % | 15 Wt % | 30 Wt % |
| Oxycodone Hydrochloride (active) | 5.0 | 15.0 | 30.0 |
| Sentry PolyOX WSR N-10 LEO, NF (matrix, e.g., PEO) | 35.0 | 35.0 | 35.0 |
| Carbowax Sentry Polyethylene Glycol 8000 Powder, NF (plasticizer) | 22.5 | 17.5 | 10.0 |
| Lactose Monohydrate 316L FastFlo (filler) | 22.5 | 17.5 | 10.0 |
| Calcium Acetate, USP (purity decreasing agent) | 10.0 | 10.0 | 10.0 |
| Citric Acid, Anhydrous Fine Ganular, USP (preservative) | 1.0 | 1.0 | 1.0 |
| Coloron Red Dye Blend (dye) | 4.0 | 4.0 | 4.0 |

The exemplary formulation in Example 4 was tested for dissolution, purity before and after extraction, and evaluated for the effectiveness of the dye. The dissolution and dye tests are described above in the preceding examples. The extraction test is described below. FIG. 13 shows the test results. The formulation passed dissolution testing. The formulation showed a decrease in purity after extraction in alcohol. It is noted that the formulation showed significant color after filtration with using about 4 wt % dye. Prior to filtering, the solutions were colored as a result of the dye being present in the formulation. In general, filtering the solution with a syringe filter did not substantially reduce the color of the filtrate. For nylon filters, however, a substantial reduction in color was observed. It is believed that nylon has an affinity to the dye used in the formulation. As a result, in some embodiments, a sufficient amount of dye is added to saturate any filter (e.g., a nylon filter) used to filter the solution and also to allow the filtrate to be colored (e.g., at least 1 wt % dye, at least 2 wt % dye, at least 3% dye, etc.)."

Extraction Procedure for ADF IR Extruded Pills

The extraction procedure involves testing the resultant purity of an extract using alcohol and/or water as the extraction solvent. Here, four whole ADF 30 mg IR pills were placed in a 125 mL Erlenmeyer flask. 40.0 mL of 190-proof ethanol (95%) was pipetted into the flask. The flask was sealed and allowed to shake overnight on a platform shaker (concentration of stock solution=3 mg/mL oxycodone HCl).

This procedure was repeated utilizing water as the extraction solvent.

After approximately 12 hours, both flasks were removed from the platform shaker. A portion was filtered through a 0.45 μm nylon syringe filter into a 10 mL glass beaker. 5.0 mL of this solution was pipetted into a 150 mL beaker and heated on a hot plate at ~100° C. (theoretically 15 mg of oxycodone HCl powder in solution). The heat was continuously added until each solution evaporated. Both beakers were allowed to cool to room temperature and then scraped with a metal spatula. The resulting powder was weighed and subsequently prepared for chromatographic analysis.

Each sample was weight corrected and analyzed for assay purity of oxycodone HCl.

The assay purity is the percentage of oxycodone HCl in the extracted powder. As the assay purity of oxycodone HCl decreases the amount of extracted powder necessary to achieve higher oxycodone HCl content increases. Additionally, as the assay purity of oxycodone HCl decreases, the excipient load present in the extracted powder increases. Therefore, it can be concluded that drug products which provide, upon ethanol or water extraction, a lower assay purity of oxycodone HCl in extracted powder are abuse deterrent. This deterrence is evident in the following ways: cost effectiveness (i.e., the need for more powder to produce an equivalent amount of oxycodone HCl); time effectiveness (i.e., a powder of lower purity containing oxycodone HCl which cannot be separated from the excipients without complex, time-consuming chemistry procedures); and the potential for introducing a higher excipient load into the body.

While this disclosure has been particularly shown and described with reference to example embodiments thereof, it will be understood by those skilled in the art that various changes in form and details may be made therein without departing from the scope of the invention encompassed by the appended claims.

We claim:

1. An oral, immediate release, abuse deterrent dosage form comprising:
   (i) 0.1 wt. % to 30.0 wt. % of an active substance susceptible to abuse;
   (ii) a matrix agent, wherein the matrix agent is 45 wt. % to 55 wt. % polyethylene oxide (PEO) having an average molecular weight between 50K and 150K Daltons;
   (iii) 15 wt. % to 30 wt. % of a plasticizer, wherein the plasticizer has an average molecular weight between 1K Daltons and 15K Daltons, wherein the plasticizer is a polyalkylene glycol;
   (iv) 0 wt. % to 40 wt. % of a filler,
   (v) 0 wt. % to 2.0 wt. % of an antioxidant, and,
   (vi) 0 wt. % to 20.0 wt. % of a dye,
   wherein the active substance susceptible to abuse is selected from the group consisting of: alfentanil, allylprodine, alphaprodine, amphetamine, anileridine, benzylmorphine, bezitramide, buprenorphine, butorphanol, clonitazene, codeine, cyclazocine, desomorphine, dextroamphetamine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, tramadol, and pharmaceutically acceptable salts and/or mixtures thereof;
   wherein the active substance susceptible to abuse has an immediate release profile wherein greater than or equal to 75 wt. % of the active substance is released from the dosage form at 45 minutes following a dissolution test in deaerated water, wherein the dosage form includes a physical barrier to reduce abuse, wherein the physical barrier is having at least 50 wt. % of particles with a particle size greater than 0.5 mm following physical or mechanical manipulation of the dosage form, wherein said physical or mechanical manipulation comprises grinding in a MR. COFFEE® model number IDS55 coffee grinder or equivalent at 20,000 rpm and for 30-60 seconds;
   wherein the dosage form is a formed, uniform extrudate having a uniform blend of active, matrix agent and plasticizer, and is directly formed from an extrusion process, and wherein said dosage form excludes disintegrant that promotes disintegration of the dosage form and dissolution of the active substance.

2. The oral, immediate release, abuse deterrent pill of claim 1, wherein the active substance is Oxycodone or Hydrocodone.

3. The oral, immediate release, abuse deterrent pill of claim 1, wherein the physical barrier reduces abuse by pulverizing and swallowing, pulverizing and snorting, or pulverizing and injecting.

4. The oral, immediate release, abuse deterrent pill of claim 1, comprising 20 wt. % to 30 wt. % of said filler.

5. The oral, immediate release, abuse deterrent pill of claim 1, further comprising 0.1 wt. % to 2.0 wt. % of one or more preservatives.

6. The oral, immediate release, abuse deterrent pill of claim 1, further comprising a FD&C dye.

7. The oral, immediate release, abuse deterrent pill of claim 1, wherein less than or equal to 60 wt. % of the active substance is released from the dosage form at 20 minutes following a dissolution test in deaerated water.

8. The oral, immediate release, abuse deterrent pill of claim 1, which is a 100 mg pill.

9. A method of treating pain comprising administering to an individual in need thereof a therapeutically effective amount of the oral, immediate release, abuse deterrent dosage form of claim 1.

10. A process for the production of an oral, immediate release, abuse deterrent dosage form containing at least one active substance susceptible to abuse, said process comprising:
   (i) processing a uniform blend of at least one active substance susceptible to abuse, a matrix agent, a plasticizer, and optionally a filler, an antioxidant, and a dye, by hot melt extrusion using an extruder to make an extrudate; and
   (ii) forming the extrudate using a forming unit into the dosage form,
   wherein the dosage form excludes disintegrant that promotes disintegration of the dosage form and dissolution of the active substance, said dosage form comprises:
   (a) 0.1 wt. % to 30.0 wt. % of the active substance susceptible to abuse;
   (b) 45 wt. % to 55 wt. % of the matrix agent which is polyethylene oxide (PEO) having an average molecular weight between 50K Daltons and 150K Daltons;
   (c) 15 wt. % to 30 wt. % of the plasticizer which is polyalkylene glycol having an average molecular weight between 1K Daltons and 15K Daltons;
   (d) 0 wt. % to 40 wt. % of a filler;
   (e) 0 wt. % to 2.0 wt. % of an antioxidant, and,
   (f) 0 wt. % to 20.0 wt. % of a dye,
   wherein the active substance susceptible to abuse is selected from the group consisting of: alfentanil, allylprodine, alphaprodine, amphetamine, anileridine, benzylmorphine, bezitramide, buprenorphine, butorphanol, clonitazene, codeine, cyclazocine, desomorphine, dextroamphetamine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, tramadol, and pharmaceutically acceptable salts and/or mixtures thereof;

wherein greater than or equal to 75 wt. % of the active substance is released from the dosage form at 45 minutes following a dissolution test in deaerated water, wherein the dosage form includes a physical barrier to reduce abuse, wherein the physical barrier is having at least 50 wt. % of particles with a particle size greater than 0.5 mm following physical or mechanical manipulation of the dosage form, wherein said physical or mechanical manipulation comprises grinding in a MR. COFFEE® model number IDS55 coffee grinder or equivalent at 20,000 rpm and for 30-60 seconds.

11. The process for the production of an oral, immediate release, abuse deterrent dosage form of claim 10, wherein the forming unit is a unit capable of forming the dosage form without prior cutting of the extrudate.

12. The process for the production of an oral, immediate release, abuse deterrent dosage form of claim 11, wherein the unit capable of forming the dosage form is a calendar, a rotary or a chain forming machine.

13. The process for the production of an oral, immediate release, abuse deterrent dosage form of claim 10, wherein the processing of the uniform blend is performed at a processing temperature and a processing pressure such that the matrix agent and plasticizer soften and the at least one active substance susceptible to abuse does not substantially degrade.

14. The process for the production of an oral, immediate release, abuse deterrent dosage form of claim 13, wherein at least one temperature zone of the extruder has a processing temperature equal to or below 75° C.

15. The process for the production of an oral, immediate release, abuse deterrent dosage form of claim 13, wherein at least one pressure zone of the extruder has a processing pressure equal to or above 5 Bar.

16. The process for the production of an oral, immediate release, abuse deterrent dosage form of claim 10, further comprising transferring the extrudate to the forming unit using a transfer unit capable of controlling the temperature, pressure, environment, and/or shape of the extrudate.

17. The process for the production of an oral, immediate release, abuse deterrent dosage form of claim 10, further comprising monitoring a mixture of the at least one active substance susceptible to abuse, the matrix agent and the plasticizer during blending using a process analytical technique to determine when a uniform blend is achieved.

18. The process for the production of an oral, immediate release, abuse deterrent dosage form of claim 10, further comprising determining the quality, volume and weight of the dosage form using an optical inspection technique.

19. A process for the production of an oral, immediate release, abuse deterrent dosage form, said process comprising processing an analytically determined uniform blend of at least one active substance susceptible to abuse, a matrix agent and a plasticizer by hot melt extrusion using an extruder to make an extrudate and forming the dosage form, wherein said dosage form excludes disintegrant that promotes disintegration of the dosage form and dissolution of the active substance, said dosage form comprises:
(a) 0.1 wt. % to 30.0 wt. % of the active substance susceptible to abuse;
(b) 45 wt. % to 55 wt. % of the matrix agent which is polyethylene oxide (PEO) having an average molecular weight between 50K Daltons and 150K Daltons;
(c) 15 wt. % to 30 wt. % of the plasticizer which is polyalkylene glycol having an average molecular weight between 1K Daltons and 15K Daltons;
(d) 0 wt. % to 40 wt. % of a filler;
(e) 0 wt. % to 2.0 wt. % of an antioxidant, and,
(f) 0 wt. % to 20.0 wt. % of a dye
wherein the active substance susceptible to abuse is selected from the group consisting of: alfentanil, allylprodine, alphaprodine, amphetamine, anileridine, benzylmorphine, bezitramide, buprenorphine, butorphanol, clonitazene, codeine, cyclazocine, desomorphine, dextroamphetamine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, tramadol, and pharmaceutically acceptable salts and/or mixtures thereof.

20. A process for the production of an oral, immediate release, abuse deterrent dosage form containing at least one active substance susceptible to abuse comprising:
(i) combining the at least one active substance susceptible to abuse, a matrix agent and a plasticizer in a hopper to form a mixture;
(ii) blending the mixture in the hopper until a uniform blend is achieved;
(iii) monitoring the mixture during blending using a process analytical technique to determine when a uniform blend is achieved;
(iv) feeding the uniform blend into an extruder;
(v) processing the uniform blend by hot melt extrusion in the extruder to make an extrudate;
(vi) transferring the extrudate to a forming unit using a transfer unit capable of controlling the temperature, pressure, environment or shape of the extrudate;
(vii) forming the extrudate using the forming unit into the dosage form; and
(viii) determining the quality, volume and weight of the dosage form using an optical inspection technique,
wherein said dosage form excludes disintegrant that promotes disintegration of the dosage form and dissolution of the active substance, said dosage form comprises:
(a) 0.1 wt. % to 30.0 wt. % of the active substance susceptible to abuse;
(b) 45 wt. % to 55 wt. % of the matrix agent which is polyethylene oxide (PEO) having an average molecular weight between 50K Daltons and 150K Daltons;
(c) 15 wt. % to 30 wt. % of the plasticizer which is polyalkylene glycol having an average molecular weight between 1K Daltons and 15K Daltons;
(d) 0 wt. % to 40 wt. % of a filler;
(e) 0 wt. % to 2.0 wt. % of an antioxidant, and,
(f) 0 wt. % to 20.0 wt. % of a dye
wherein the active substance susceptible to abuse is selected from the group consisting of: alfentanil, allylprodine, alphaprodine, amphetamine, anileridine, benzylmorphine, bezitramide, buprenorphine, butorphanol, clonitazene, codeine, cyclazocine, desomorphine, dextroamphetamine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, tramadol, and pharmaceutically acceptable salts and/or mixtures thereof.

\* \* \* \* \*